(12) United States Patent
da Veiga Beltrame et al.

(10) Patent No.: US 12,286,621 B2
(45) Date of Patent: Apr. 29, 2025

(54) EFFICIENT COMBINATORIAL BEAD BARCODING

(71) Applicant: California Institute of Technology, Pasadena, CA (US)

(72) Inventors: Eduardo da Veiga Beltrame, Pasadena, CA (US); Jase Gehring, Pasadena, CA (US); Akshay Tambe, Hayward, CA (US); Lior S. Pachter, Pasadena, CA (US); Taleen Dilanyan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 197 days.

(21) Appl. No.: 16/586,592

(22) Filed: Sep. 27, 2019

(65) Prior Publication Data

US 2020/0102556 A1  Apr. 2, 2020

Related U.S. Application Data

(60) Provisional application No. 62/738,127, filed on Sep. 28, 2018.

(51) Int. Cl.
| | | |
|---|---|---|
| *C12N 15/10* | (2006.01) | |
| *C12N 15/11* | (2006.01) | |
| *C12N 15/66* | (2006.01) | |
| *C40B 20/04* | (2006.01) | |
| *C40B 50/14* | (2006.01) | |
| *C40B 70/00* | (2006.01) | |

(52) U.S. Cl.
CPC ..... *C12N 15/1065* (2013.01); *C12N 15/1096* (2013.01); *C12N 15/11* (2013.01); *C40B 20/04* (2013.01); *C40B 50/14* (2013.01); *C40B 70/00* (2013.01)

(58) Field of Classification Search
CPC .......... C12N 15/1065; C12N 15/1096; C12N 15/11; C12N 15/66; C40B 20/04; C40B 50/14; C40B 70/00; C40B 40/06; C12Q 2533/101; C12Q 2563/179
See application file for complete search history.

(56) References Cited

U.S. PATENT DOCUMENTS

| 9,080,169 B2 | 7/2015 | Krauss et al. |
| 2002/0034747 A1 | 3/2002 | Bruchez et al. |
| 2014/0155274 A1* | 6/2014 | Xie ............... C12Q 1/6874 |
| | | 506/2 |
| 2014/0378349 A1 | 12/2014 | Hindson et al. |
| 2015/0005200 A1 | 1/2015 | Hindson et al. |
| 2019/0106733 A1* | 4/2019 | Kishi et al. ......... C12Q 1/6811 |
| 2020/0362398 A1* | 11/2020 | Kishi et al. ......... C12Q 1/6841 |

FOREIGN PATENT DOCUMENTS

| WO | WO2017120531 | 7/2017 |
| WO | WO2017143006 | 8/2017 |

OTHER PUBLICATIONS

Hollenstein "DNA Synthesis by Primer Exchange Reaction Cascades" Chembiochem Mar. 2, 2018;19(5):422-424 doi: 10.1002/cbic.201700639. Epub Jan. 24, 2018 (Year: 2018).*
Cao et al., "Comprehensive single-cell transcriptional profiling of a multicellular organism," Science 2017, 357, 661-667.
Hansen, "Use of Solubilizable Acrylamide Disulfide Gels for Isolation of DNA Fragments Suitable for Sequence Analysis," Analytical Biochemistry 1981, 116(1), 146-151.
International Search Report and Written Opinion dated Mar. 20, 2020 in PCT Patent Application No. PCT/US2019/053566.
Kishi et al., "Programmable autonomous synthesis of single-stranded DNA," Nature Chemistry 2018, 10, 155-164.
Klein et al., "Droplet Barcoding for Single-Cell Transcriptomics Applied to Embryonic Stem Cells," Cell 2015, 161, 1187-1201.
Macosko et al., "Highly Parallel Genome-wide Expression Profiling of Individual Cells Using Nanoliter Droplets," Cell 2015, 161, 1202-1214.
Peacock et al., "Resolution of Multiple Ribonucleic Acid Species by Polyacrylamide Gel Electrophoresis," Biochemistry 1967, 6(6), 1818-1827.
Rosenberg et al., "Single-cell profiling of the developing mouse brain and spinal cord with split-pool barcoding," Science 2018, 360, 176-182.
Scillia et al., "Programmable polymer-DNA hydrogels with dual input and multiscale responses," Biomater. Sci. 2014, 2, 203-211.
Zilionis et al., "Single-cell barcoding and sequencing using droplet microfluidics," Nature Protocols 2017, 12(1), 44-73.
International Preliminary Report on Patentability dated Mar. 23, 2021 in PCT Patent Application No. PCT/US2019/053566.

* cited by examiner

*Primary Examiner* — Sahana S Kaup
(74) *Attorney, Agent, or Firm* — Dickinson Wright PLLC

(57) ABSTRACT

Disclosed herein include methods, compositions, and systems for extending particle-associated oligonucleotides. In some embodiments, the methods of extending particle-associated oligonucleotides enable efficient methods of preparing a library of barcoded beads. It is also provided, in some embodiments, hydrogel beads degradable upon application of a chemical stimulus that comprise releasably attached oligonucleotides.

18 Claims, 9 Drawing Sheets

Specification includes a Sequence Listing.

5' HHHHH YYYYYYYY GGGCCTTTTGGCCC XXXXXXXX DDDDD AGATCGGAA TTTTTTTT 3'
   306   310        314  316      312      308    304       318

302 → (SEQ ID NO: 44)

FIG. 3A

Acrydite-modified Input Primer
5' /5Acryd/TTT TTT T/ideoxyU/C TAC ACG ACG CTC TTC CGA TCT 3' (SEQ ID NO: 45)

First Hairpin Molecule
5' ACCTC CAAACCTCA GGGCCTTTTGGCCC TGAGGTTTG GAGGT AGATCGGAA TTTTTTTT 3' (SEQ ID NO: 1)

Second Hairpin Molecule
5' ACCTC CTTTCTCTT GGGCCTTTTGGCCC AAGAGAAAG GAGGT TGAGGTTTG TTTTTTTT 3' (SEQ ID NO: 11)

Third Hairpin Molecule
5' ACCTC CTAACACTC GGGCCTTTTGGCCC GAGTGTTAG GAGGT AAGAGAAAG TTTTTTTT 3' (SEQ ID NO: 21)

Fourth Hairpin Molecule
5' ACCTC CTTTAAACT GGGCCTTTTGGCCC AGTTTAAAG GAGGT GAGTGTTAG TTTTTTTT 3' (SEQ ID NO: 31)

Capping Oligonucleotide
5' TCGACGACGAGCGCGGCGATATCATCATCCAT NNNNNNNNN TTTAACCTATAGTTTAAAG 3' (SEQ ID NO: 46)

Barcoded Bead Oligonucleotide
5' /5Acryd/TTTTTTT/ideoxyU/CTACACGACGCTCTTCCGATCT-HHHHH-ACTCCAAAC-HHHHH-TTCTCTTTC-HHHHH-CTCACAATC-HHHHH-CTTTAAACTATAGTAAA-NNNNNNNNN-ATGGATGATGATATCGCCGCGCTCGTCGTCGA 3' (SEQ ID NO: 47)

FIG. 3B

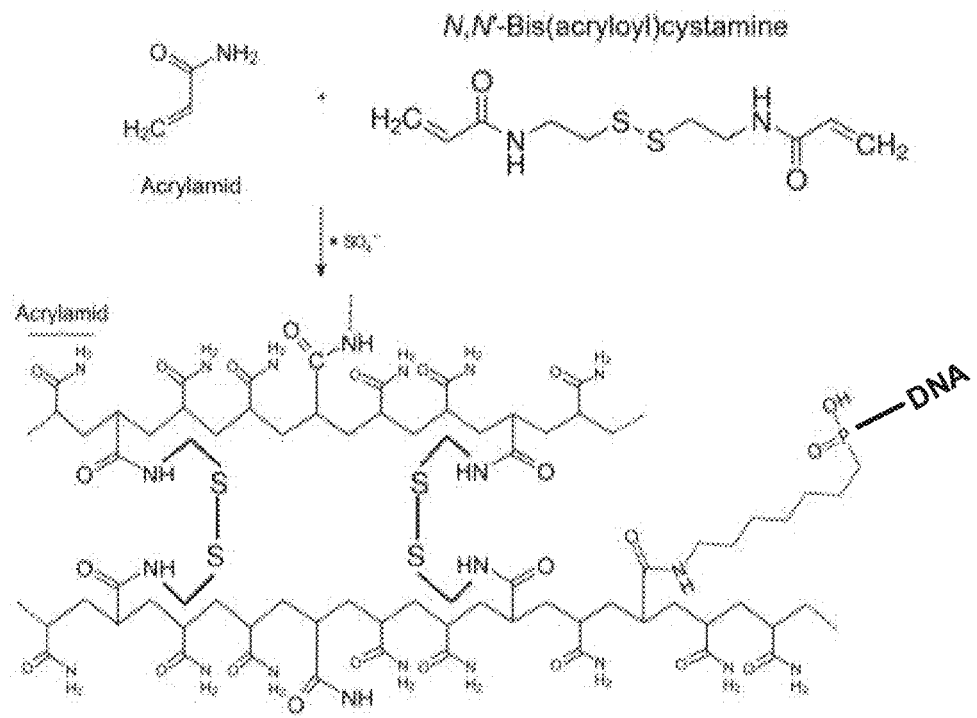
FIG. 5A
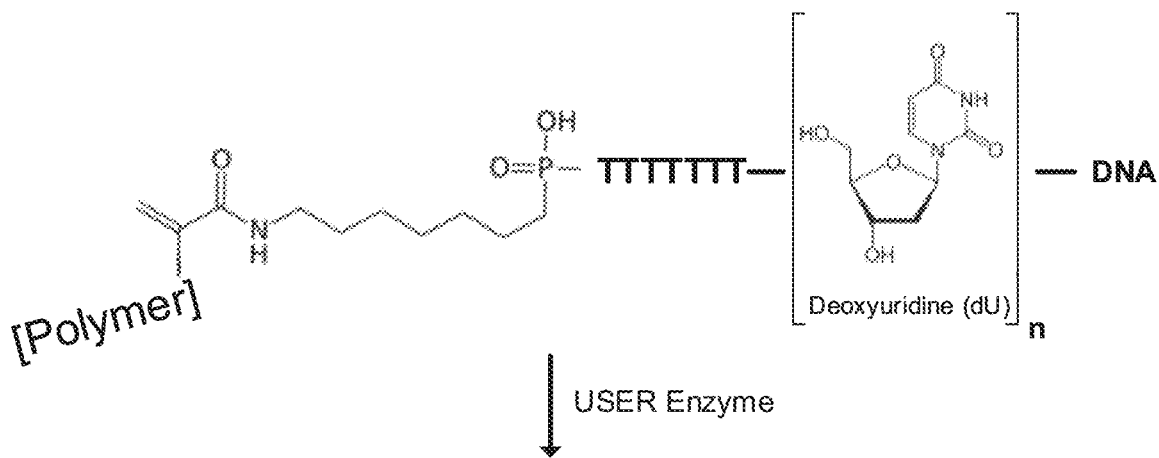
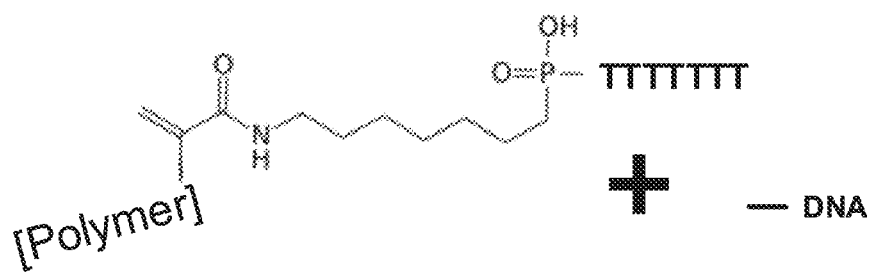
FIG. 5B

SEQUENCE LISTING

```
<160> NUMBER OF SEQ ID NOS: 47

<210> SEQ ID NO 1
<211> LENGTH: 59
<212> TYPE: DNA
<213> ORGANISM: Artificial Sequence
<220> FEATURE:
<223> OTHER INFORMATION: H1-1-v3

<400> SEQUENCE: 1
acctccaaac ctcagggcct tttggccctg aggtttggag gtagatcgga atttttttt      59

<210> SEQ ID NO 2
<211> LENGTH: 59
<212> TYPE: DNA
<213> ORGANISM: Artificial Sequence
<220> FEATURE:
<223> OTHER INFORMATION: H1-2-v3

<400> SEQUENCE: 2
actttcaaac ctcagggcct tttggccctg aggtttgaaa gtagatcgga atttttttt      59
```

```
<210> SEQ ID NO 3
<211> LENGTH: 59
<212> TYPE: DNA
<213> ORGANISM: Artificial Sequence
<220> FEATURE:
<223> OTHER INFORMATION: H1-3-v3

<400> SEQUENCE: 3
aacatcaaac ctcagggcct tttggccctg aggtttgatg ttagatcgga attttttt          59

<210> SEQ ID NO 4
<211> LENGTH: 59
<212> TYPE: DNA
<213> ORGANISM: Artificial Sequence
<220> FEATURE:
<223> OTHER INFORMATION: H1-4-v3

<400> SEQUENCE: 4
aactccaaac ctcagggcct tttggccctg aggtttggag ttagatcgga attttttt          59

<210> SEQ ID NO 5
<211> LENGTH: 59
<212> TYPE: DNA
<213> ORGANISM: Artificial Sequence
<220> FEATURE:
<223> OTHER INFORMATION: H1-5-v3

<400> SEQUENCE: 5
actatcaaac ctcagggcct tttggccctg aggtttgata gtagatcgga attttttt          59

<210> SEQ ID NO 6
<211> LENGTH: 59
<212> TYPE: DNA
<213> ORGANISM: Artificial Sequence
<220> FEATURE:
<223> OTHER INFORMATION: H1-6-v3

<400> SEQUENCE: 6
aattccaaac ctcagggcct tttggccctg aggtttggaa ttagatcgga attttttt          59

<210> SEQ ID NO 7
<211> LENGTH: 59
<212> TYPE: DNA
<213> ORGANISM: Artificial Sequence
<220> FEATURE:
<223> OTHER INFORMATION: H1-7-v3

<400> SEQUENCE: 7
aatctcaaac ctcagggcct tttggccctg aggtttgaga ttagatcgga attttttt          59

<210> SEQ ID NO 8
<211> LENGTH: 59
<212> TYPE: DNA
<213> ORGANISM: Artificial Sequence
<220> FEATURE:
<223> OTHER INFORMATION: H1-8-v3

<400> SEQUENCE: 8
aaacacaaac ctcagggcct tttggccctg aggtttgtgt ttagatcgga attttttt          59

<210> SEQ ID NO 9
<211> LENGTH: 59
<212> TYPE: DNA
<213> ORGANISM: Artificial Sequence
<220> FEATURE:
<223> OTHER INFORMATION: H1-9-v3
```

<400> SEQUENCE: 9
aacttcaaac ctcagggcct tttggccctg aggtttgaag ttagatcgga atttttttt    59

<210> SEQ ID NO 10
<211> LENGTH: 59
<212> TYPE: DNA
<213> ORGANISM: Artificial Sequence
<220> FEATURE:
<223> OTHER INFORMATION: H1-10-v3

<400> SEQUENCE: 10
accctcaaac ctcagggcct tttggccctg aggtttgagg gtagatcgga atttttttt    59

<210> SEQ ID NO 11
<211> LENGTH: 59
<212> TYPE: DNA
<213> ORGANISM: Artificial Sequence
<220> FEATURE:
<223> OTHER INFORMATION: H2-1-v3

<400> SEQUENCE: 11
acctcctttc tcttgggcct tttggcccaa gagaaaggag gttgaggttt gttttttttt   59

<210> SEQ ID NO 12
<211> LENGTH: 59
<212> TYPE: DNA
<213> ORGANISM: Artificial Sequence
<220> FEATURE:
<223> OTHER INFORMATION: H2-2-v3

<400> SEQUENCE: 12
actttctttc tcttgggcct tttggcccaa gagaaagaaa gttgaggttt gttttttttt   59

<210> SEQ ID NO 13
<211> LENGTH: 59
<212> TYPE: DNA
<213> ORGANISM: Artificial Sequence
<220> FEATURE:
<223> OTHER INFORMATION: H2-3-v3

<400> SEQUENCE: 13
aacatctttc tcttgggcct tttgcccaa gagaaagatg tttgaggttt gttttttttt    59

<210> SEQ ID NO 14
<211> LENGTH: 59
<212> TYPE: DNA
<213> ORGANISM: Artificial Sequence
<220> FEATURE:
<223> OTHER INFORMATION: H2-4-v3

<400> SEQUENCE: 14
aactcctttc tcttgggcct tttggcccaa gagaaaggag tttgaggttt gttttttttt   59

<210> SEQ ID NO 15
<211> LENGTH: 59
<212> TYPE: DNA
<213> ORGANISM: Artificial Sequence
<220> FEATURE:
<223> OTHER INFORMATION: H2-5-v3

<400> SEQUENCE: 15
actatctttc tcttgggcct tttggcccaa gagaaagata gttgaggttt gttttttttt   59

<210> SEQ ID NO 16

```
<211> LENGTH: 59
<212> TYPE: DNA
<213> ORGANISM: Artificial Sequence
<220> FEATURE:
<223> OTHER INFORMATION: H2-6-v3

<400> SEQUENCE: 16
aattcctttc tcttgggcct tttggcccaa gagaaaggaa tttgaggttt gttttttt        59

<210> SEQ ID NO 17
<211> LENGTH: 59
<212> TYPE: DNA
<213> ORGANISM: Artificial Sequence
<220> FEATURE:
<223> OTHER INFORMATION: H2-7-v3

<400> SEQUENCE: 17
aatctctttc tcttgggcct tttggcccaa gagaaagaga tttgaggttt gttttttt        59

<210> SEQ ID NO 18
<211> LENGTH: 59
<212> TYPE: DNA
<213> ORGANISM: Artificial Sequence
<220> FEATURE:
<223> OTHER INFORMATION: H2-8-v3

<400> SEQUENCE: 18
aaacactttc tcttgggcct tttggcccaa gagaaagtgt tttgaggttt gttttttt        59

<210> SEQ ID NO 19
<211> LENGTH: 59
<212> TYPE: DNA
<213> ORGANISM: Artificial Sequence
<220> FEATURE:
<223> OTHER INFORMATION: H2-9-v3

<400> SEQUENCE: 19
aacttctttc tcttgggcct tttggcccaa gagaaagaag tttgaggttt gttttttt        59

<210> SEQ ID NO 20
<211> LENGTH: 59
<212> TYPE: DNA
<213> ORGANISM: Artificial Sequence
<220> FEATURE:
<223> OTHER INFORMATION: H2-10-v3

<400> SEQUENCE: 20
accctctttc tcttgggcct tttggcccaa gagaaagagg gttgaggttt gttttttt        59

<210> SEQ ID NO 21
<211> LENGTH: 59
<212> TYPE: DNA
<213> ORGANISM: Artificial Sequence
<220> FEATURE:
<223> OTHER INFORMATION: H3-1-v3

<400> SEQUENCE: 21
acctcctaac actcgggcct tttggcccga gtgttaggag gtaagagaaa gttttttt        59

<210> SEQ ID NO 22
<211> LENGTH: 59
<212> TYPE: DNA
<213> ORGANISM: Artificial Sequence
<220> FEATURE:
<223> OTHER INFORMATION: H3-2-v3

<400> SEQUENCE: 22
```
actttctaac actcgggcct tttggcccga gtgttagaaa gtaagagaaa gttttttt       59

<210> SEQ ID NO 23
<211> LENGTH: 59
<212> TYPE: DNA
<213> ORGANISM: Artificial Sequence
<220> FEATURE:
<223> OTHER INFORMATION: H3-3-v3

<400> SEQUENCE: 23
aacatctaac actcgggcct tttggcccga gtgttagatg ttaagagaaa gttttttt       59

<210> SEQ ID NO 24
<211> LENGTH: 59
<212> TYPE: DNA
<213> ORGANISM: Artificial Sequence
<220> FEATURE:
<223> OTHER INFORMATION: H3-4-v3

<400> SEQUENCE: 24
aactcctaac actcgggcct tttggcccga gtgttaggag ttaagagaaa gttttttt       59

<210> SEQ ID NO 25
<211> LENGTH: 59
<212> TYPE: DNA
<213> ORGANISM: Artificial Sequence
<220> FEATURE:
<223> OTHER INFORMATION: H3-5-v3

<400> SEQUENCE: 25
actatctaac actcgggcct tttggcccga gtgttagata gtaagagaaa gttttttt       59

<210> SEQ ID NO 26
<211> LENGTH: 59
<212> TYPE: DNA
<213> ORGANISM: Artificial Sequence
<220> FEATURE:
<223> OTHER INFORMATION: H3-6-v3

<400> SEQUENCE: 26
aattcctaac actcgggcct tttggcccga gtgttaggaa ttaagagaaa gttttttt       59

<210> SEQ ID NO 27
<211> LENGTH: 59
<212> TYPE: DNA
<213> ORGANISM: Artificial Sequence
<220> FEATURE:
<223> OTHER INFORMATION: H3-7-v3

<400> SEQUENCE: 27
aatctctaac actcgggcct tttggcccga gtgttagaga ttaagagaaa gttttttt       59

<210> SEQ ID NO 28
<211> LENGTH: 59
<212> TYPE: DNA
<213> ORGANISM: Artificial Sequence
<220> FEATURE:
<223> OTHER INFORMATION: H3-8-v3

<400> SEQUENCE: 28
aaacactaac actcgggcct tttggcccga gtgttagtgt ttaagagaaa gttttttt       59

<210> SEQ ID NO 29
<211> LENGTH: 59
<212> TYPE: DNA

<213> ORGANISM: Artificial Sequence
<220> FEATURE:
<223> OTHER INFORMATION: H3-9-v3

<400> SEQUENCE: 29
aacttctaac actcgggcct tttggcccga gtgttagaag ttaagagaaa gttttttt    59

<210> SEQ ID NO 30
<211> LENGTH: 59
<212> TYPE: DNA
<213> ORGANISM: Artificial Sequence
<220> FEATURE:
<223> OTHER INFORMATION: H3-10-v3

<400> SEQUENCE: 30
accctctaac actcgggcct tttggcccga gtgttagagg gtaagagaaa gttttttt    59

<210> SEQ ID NO 31
<211> LENGTH: 59
<212> TYPE: DNA
<213> ORGANISM: Artificial Sequence
<220> FEATURE:
<223> OTHER INFORMATION: H4-1-v3

<400> SEQUENCE: 31 acctcctta aactgggcct tttggcccag tttaaaggag gtgagtgtta gttttttt    59

<210> SEQ ID NO 32
<211> LENGTH: 59
<212> TYPE: DNA
<213> ORGANISM: Artificial Sequence
<220> FEATURE:
<223> OTHER INFORMATION: H4-2-v3

<400> SEQUENCE: 32
actttcttta aactgggcct tttggcccag tttaaagaaa gtgagtgtta gttttttt    59

<210> SEQ ID NO 33
<211> LENGTH: 59
<212> TYPE: DNA
<213> ORGANISM: Artificial Sequence
<220> FEATURE:
<223> OTHER INFORMATION: H4-3-v3

<400> SEQUENCE: 33
aacatcttta aactgggcct tttggcccag tttaaagatg ttgagtgtta gttttttt    59

<210> SEQ ID NO 34
<211> LENGTH: 59
<212> TYPE: DNA
<213> ORGANISM: Artificial Sequence
<220> FEATURE:
<223> OTHER INFORMATION: H4-4-v3

<400> SEQUENCE: 34 aactcctta aactgggcct tttggcccag tttaaaggag ttgagtgtta gttttttt    59

<210> SEQ ID NO 35
<211> LENGTH: 59
<212> TYPE: DNA
<213> ORGANISM: Artificial Sequence
<220> FEATURE:
<223> OTHER INFORMATION: H4-5-v3

<400> SEQUENCE: 35
actatcttta aactgggcct tttggcccag tttaaagata gtgagtgtta gttttttt    59

<210> SEQ ID NO 36
<211> LENGTH: 59
<212> TYPE: DNA
<213> ORGANISM: Artificial Sequence
<220> FEATURE:
<223> OTHER INFORMATION: H4-6-v3

<400> SEQUENCE: 36
aattccttta aactgggcct tttggcccag tttaaaggaa ttgagtgtta gttttttttt    59

<210> SEQ ID NO 37
<211> LENGTH: 59
<212> TYPE: DNA
<213> ORGANISM: Artificial Sequence
<220> FEATURE:
<223> OTHER INFORMATION: H4-7-v3

<400> SEQUENCE: 37
aatctcttta aactgggcct tttggcccag tttaaagaga ttgagtgtta gttttttttt    59

<210> SEQ ID NO 38
<211> LENGTH: 59
<212> TYPE: DNA
<213> ORGANISM: Artificial Sequence
<220> FEATURE:
<223> OTHER INFORMATION: H4-8-v3

<400> SEQUENCE: 38
aaacacttta aactgggcct tttggcccag tttaaagtgt ttgagtgtta gttttttttt    59

<210> SEQ ID NO 39
<211> LENGTH: 59
<212> TYPE: DNA
<213> ORGANISM: Artificial Sequence
<220> FEATURE:
<223> OTHER INFORMATION: H4-9-v3

<400> SEQUENCE: 39
aacttcttta aactgggcct tttggcccag tttaaagaag ttgagtgtta gttttttttt    59

<210> SEQ ID NO 40
<211> LENGTH: 59
<212> TYPE: DNA
<213> ORGANISM: Artificial Sequence
<220> FEATURE:
<223> OTHER INFORMATION: H4-10-v3

<400> SEQUENCE: 40
accctcttta aactgggcct tttggcccag tttaaagagg gtgagtgtta gttttttttt    59

<210> SEQ ID NO 41
<211> LENGTH: 56
<212> TYPE: DNA
<213> ORGANISM: Artificial Sequence
<220> FEATURE:
<223> OTHER INFORMATION: ACTPE2 primer

<400> SEQUENCE: 41
gtgactggag ttcagacgtg tgctcttccg atcttcgacg acgagcgcgg cgatat    56

<210> SEQ ID NO 42
<211> LENGTH: 58
<212> TYPE: DNA
<213> ORGANISM: Artificial Sequence
<220> FEATURE:

```
<223> OTHER INFORMATION: 58-R1P5 primer

<400> SEQUENCE: 42
aatgatacgg cgaccaccga gatctacact ctttccctac acgacgctct tccgatct          58

<210> SEQ ID NO 43
<211> LENGTH: 53
<212> TYPE: DNA
<213> ORGANISM: Artificial Sequence
<220> FEATURE:
<223> OTHER INFORMATION: R2P7B1 primer

<400> SEQUENCE: 43
caagcagaag acggcatacg agataagatt acgtgactgg agttcagacg tgt              53

<210> SEQ ID NO 44
<211> LENGTH: 14
<212> TYPE: DNA
<213> ORGANISM: Artificial Sequence
<220> FEATURE:
<223> OTHER INFORMATION: Exemplary coupling segment

<400> SEQUENCE: 44
gggccttttg gccc                                                          14

<210> SEQ ID NO 45
<211> LENGTH: 29
<212> TYPE: DNA
<213> ORGANISM: Artificial Sequence
<220> FEATURE:
<223> OTHER INFORMATION: Input primer
<220> FEATURE:
<221> NAME/KEY: misc_feature
<222> LOCATION: (1)..(1)
<223> OTHER INFORMATION: 5' acrydite

<400> SEQUENCE: 45
tttttttcta cacgacgctc ttccgatct                                          29

<210> SEQ ID NO 46
<211> LENGTH: 60
<212> TYPE: DNA
<213> ORGANISM: Artificial Sequence
<220> FEATURE:
<223> OTHER INFORMATION: Exemplary capping oligonucleotide
<220> FEATURE:
<221> NAME/KEY: misc_feature
<222> LOCATION: (33)..(42)
<223> OTHER INFORMATION: n is a, c, g, or t

<400> SEQUENCE: 46
tcgacgacga gcgcggcgat atcatcatcc atnnnnnnnn nntttaccta tagtttaaag        60

<210> SEQ ID NO 47
<211> LENGTH: 137
<212> TYPE: DNA
<213> ORGANISM: Artificial Sequence
<220> FEATURE:
<223> OTHER INFORMATION: Exemplary barcoded and capped bead
      oligonucleotide
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (8)..(8)
<223> OTHER INFORMATION: n is deoxyuridine
<220> FEATURE:
```

```
<221> NAME/KEY: misc_feature
<222> LOCATION: (96)..(105)
<223> OTHER INFORMATION: n is a, c, g, or t

<400> SEQUENCE: 47 ttttttnct acacgacgct cttccgatct hhhhhactcc aaachhhhht tctctttchh    60
hhhctcacaa tchhhhhctt taaactatag gtaaannnnn nnnnnatgga tgatgatatc  120
gccgcgctcg tcgtcga                                                 137
```

EFFICIENT COMBINATORIAL BEAD BARCODING

RELATED APPLICATIONS

This application claims the benefit under 35 U.S.C. § 119(e) of U.S. Provisional Application No. 62/738,127, filed Sep. 28, 2018, the content of this related application is incorporated herein by reference in its entirety for all purposes.

REFERENCE TO SEQUENCE LISTING

The present application is being filed along with a Sequence Listing in electronic format. The Sequence Listing is provided as a file entitled Sequence_Listing_30KJ302412US, created Sep. 27, 2019, which is 12 kilobytes in size. The information in the electronic format of the Sequence Listing is incorporated herein by reference in its entirety.

BACKGROUND

Field

The present disclosure relates generally to the field of barcoding microparticles.

Description of the Related Art

The production of barcoded particles (e.g., DNA-barcoded hydrogel beads) is of interest for many biotechnology applications, such as nucleic acid sequencing. However, the manufacturing of barcoded particles is challenging due to a number of technical obstacles. In particular, extension of oligonucleotides on beads in a manner that is efficient and cost-effective is one of the key challenges in manufacturing barcoded beads. Among the aforementioned technical obstacles is a requirement for high numbers of input DNA oligonucleotide barcodes for use with current DNA extension methods, as well as the need for washing beads between steps to prevent non-specific reactions from occurring. These requirements lead to considerable expense in labor and reagents. Furthermore, current methods for manufacturing DNA-barcoded microparticles may only allow for specific DNA barcodes to be attached to microparticles, or for specific types of microparticles to be used. There is a need for efficient methods of manufacturing barcoded particles.

SUMMARY

Disclosed herein include methods of extending particle-associated oligonucleotides. In some embodiments, the method comprises: (a) providing a particle comprising a plurality of oligonucleotides each comprising an input primer; (b) contacting the particle with a first hairpin molecule, wherein the first hairpin molecule comprises: (i) an unpaired first 3' toehold domain complementary to the input primer, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first payload segment, and complements thereof, and (iii) a first hairpin loop domain; and (c) extending the input primer hybridized to the first 3' toehold domain through the first paired stem domain of the first hairpin molecule, thereby displacing the 5' subdomain of the first hairpin molecule and forming a first extended oligonucleotide comprising the input primer, the first payload segment and the first coupling segment.

The method can comprise: (d) contacting the particle with a second hairpin molecule, wherein the second hairpin molecule comprises: (i) an unpaired second 3' toehold domain complementary to the first coupling segment, (ii) a second paired stem domain formed by intramolecular nucleotide base pairing between a 3' subdomain of the second hairpin molecule and a 5' subdomain of the second hairpin molecule, wherein the second paired stem domain comprises a second coupling segment, a second payload segment, and complements thereof, and (iii) a second hairpin loop domain; and (e) extending the first coupling segment of the first extended oligonucleotide hybridized to the second 3' toehold domain through the second paired stem domain of the second hairpin molecule, thereby displacing the 5' subdomain of the second hairpin molecule and forming a second extended oligonucleotide comprising the first coupling segment, the second payload segment and the second coupling segment.

The method can comprise: (f) contacting the particle with a third hairpin molecule, wherein the third hairpin molecule comprises: (i) an unpaired third 3' toehold domain complementary to the second coupling segment, (ii) a third paired stem domain formed by intramolecular nucleotide base pairing between a 3' subdomain of the third hairpin molecule and a 5' subdomain of the third hairpin molecule, wherein the third paired stem domain comprises a third coupling segment, a third payload segment, and complements thereof, and (iii) a third hairpin loop domain; and (g) extending the second coupling segment of the second extended oligonucleotide hybridized to the third 3' toehold domain through the third paired stem domain of the third hairpin molecule, thereby displacing the 5' subdomain of the third hairpin molecule and forming a third extended oligonucleotide comprising the second coupling segment, the third payload segment and the third coupling segment.

The method can comprise: (h) contacting the particle with a fourth hairpin molecule, wherein the fourth hairpin molecule comprises: (i) an unpaired fourth 3' toehold domain complementary to the third coupling segment, (ii) a fourth paired stem domain formed by intramolecular nucleotide base pairing between a 3' subdomain of the fourth hairpin molecule and a 5' subdomain of the fourth hairpin molecule, wherein the fourth paired stem domain comprises a fourth coupling segment, a fourth payload segment, and complements thereof, and (iii) a fourth hairpin loop domain; and (i) extending the third coupling segment of the third extended oligonucleotide hybridized to the fourth 3' toehold domain through the fourth paired stem domain of the fourth hairpin molecule, thereby displacing the 5' subdomain of the fourth hairpin molecule and forming a fourth extended oligonucleotide comprising the third coupling segment, the fourth payload segment and the fourth coupling segment.

The method can comprise: (j) contacting the particle with a fifth hairpin molecule, wherein the fifth hairpin molecule comprises: (i) an unpaired fifth 3' toehold domain complementary to the fourth coupling segment, (ii) a fifth paired stem domain formed by intramolecular nucleotide base pairing between a 3' subdomain of the fifth hairpin molecule and a 5' subdomain of the fifth hairpin molecule, wherein the fifth paired stem domain comprises a fifth coupling segment, a fifth payload segment, and complements thereof, and (iii) a fifth hairpin loop domain; and (k) extending the fourth coupling segment of the fourth extended oligonucleotide hybridized to the fifth 3' toehold domain through the fifth paired stem domain of the fifth hairpin molecule, thereby displacing the 5' subdomain of the fifth hairpin molecule and forming a fifth extended oligonucleotide comprising the fourth coupling segment, the fifth payload segment and the fifth coupling segment.

The method can comprise: (l) contacting the particle with a sixth hairpin molecule, wherein the sixth hairpin molecule comprises: (i) an unpaired sixth 3' toehold domain complementary to the fifth coupling segment, (ii) a sixth paired stem domain formed by intramolecular nucleotide base pairing between a 3' subdomain of the sixth hairpin molecule and a 5' subdomain of the sixth hairpin molecule, wherein the sixth paired stem domain comprises a sixth coupling segment, a sixth payload segment, and complements thereof, and (iii) a sixth hairpin loop domain; and (m) extending the fifth coupling segment of the fifth extended oligonucleotide hybridized to the sixth 3' toehold domain through the sixth paired stem domain of the sixth hairpin molecule, thereby displacing the 5' subdomain of the sixth hairpin molecule and forming a sixth extended oligonucleotide comprising the fifth coupling segment, the sixth payload segment and the sixth coupling segment.

The method can comprise: (n) contacting the particle with a seventh hairpin molecule, wherein the seventh hairpin molecule comprises: (i) an unpaired seventh 3' toehold domain complementary to the sixth coupling segment, (ii) a seventh paired stem domain formed by intramolecular nucleotide base pairing between a 3' subdomain of the seventh hairpin molecule and a 5' subdomain of the seventh hairpin molecule, wherein the seventh paired stem domain comprises a seventh coupling segment, a seventh payload segment, and complements thereof, and (iii) a seventh hairpin loop domain; and (o) extending the sixth coupling segment of the sixth extended oligonucleotide hybridized to the seventh 3' toehold domain through the seventh paired stem domain of the seventh hairpin molecule, thereby displacing the 5' subdomain of the seventh hairpin molecule and forming a seventh extended oligonucleotide comprising the sixth coupling segment, the seventh payload segment and the seventh coupling segment.

The method can comprise: (p) contacting the particle with an eighth hairpin molecule, wherein the eighth hairpin molecule comprises: (i) an unpaired eighth 3' toehold domain complementary to the seventh coupling segment, (ii) an eighth paired stem domain formed by intramolecular nucleotide base pairing between a 3' subdomain of the eighth hairpin molecule and a 5' subdomain of the eighth hairpin molecule, wherein the eighth paired stem domain comprises an eighth coupling segment, an eighth payload segment, and complements thereof, and (iii) an eighth hairpin loop domain; and (q) extending the seventh coupling segment of the seventh extended oligonucleotide hybridized to the eighth 3' toehold domain through the eighth paired stem domain of the eighth hairpin molecule, thereby displacing the 5' subdomain of the eighth hairpin molecule and forming an eighth extended oligonucleotide comprising the seventh coupling segment, the eighth payload segment and the eighth coupling segment.

The method can comprise repeating the following steps n times: contacting the particle with a (n+1)th hairpin molecule, wherein the (n+1)th hairpin molecule comprises: (i) an unpaired (n+1)th 3' toehold domain complementary to the nth coupling segment, (ii) a (n+1)th paired stem domain formed by intramolecular nucleotide base pairing between a 3' subdomain of the (n+1)th hairpin molecule and a 5' subdomain of the (n+1)th hairpin molecule, wherein the (n+1)th paired stem domain comprises a (n+1)th coupling segment, a (n+1)th payload segment, and complements thereof, and (iii) a (n+1)th hairpin loop domain; and extending the nth coupling segment of the nth extended oligonucleotide hybridized to the (n+1)th 3' toehold domain through the (n+1)th paired stem domain of the (n+1)th hairpin molecule, thereby displacing the 5' subdomain of the (n+1)th hairpin molecule and forming a (n+1)th extended oligonucleotide comprising the nth coupling segment, the (n+1)th payload segment and the (n+1)th coupling segment. In some embodiments, n is an integer between about 1 and about 8. The method can further comprising a capping reaction, comprising: contacting a capping oligonucleotide with the (n+1)th extended oligonucleotide, wherein the capping oligonucleotide is a single-stranded molecule comprising a 3' region capable of annealing to the 3' end of the first extended oligonucleotide, the second extended oligonucleotide, or the third extended oligonucleotide; and extending the (n+1)th extended oligonucleotide hybridized with the capping oligonucleotide, thereby generating a capped oligonucleotide.

In some embodiments, the first payload segment comprises a first barcode segment. In some embodiments, the second payload segment comprises a second barcode segment. In some embodiments, the third payload segment comprises a third barcode segment. In some embodiments, the first barcode segment is selected from a first set of barcode segments, wherein the second barcode segment is selected from a second set of barcode segments, and wherein the third barcode segment is selected from a third set of barcode segments. In some embodiments, the first payload segment, second payload segment, and/or third payload segment comprise a unique molecular identifier (UMI), a primer sequence, a primer annealing sequence, an attachment sequence, a sequencing primer sequence, or any combination thereof. In some embodiments, the second extended oligonucleotide comprises the input primer, the first payload segment, the first coupling segment, the second payload segment, and the second coupling segment. In some embodiments, the third extended oligonucleotide comprises the input primer, the first payload segment, the first coupling segment, the second payload segment, the second coupling segment, the third payload segment, and the third coupling segment.

In some embodiments, more than 80% of the first extended oligonucleotides, the second extended oligonucleotides, and/or the third extended oligonucleotides comprise a first payload segment. In some embodiments, more than 95% of the first extended oligonucleotides, the second extended oligonucleotides, and/or the third extended oligonucleotides comprise a first payload segment. In some embodiments, more than 99% of the first extended oligonucleotides the second extended oligonucleotides, and/or the third extended oligonucleotides comprise a first payload segment. In some embodiments, the extension of particle-associated oligonucleotides requires at least ten-fold less input nucleic acid as compared to a ligation-based method of extending particle-associated oligonucleotides. In some embodiments, the extension of particle-associated oligonucleotides requires at least hundred-fold less input nucleic acid as compared to a ligation-based method of extending particle-associated oligonucleotides. In some embodiments, one or more of steps (b), (c), (d), (e), (f) and (g) is performed under condition(s) that result in annealing, nucleic acid polymerization, and strand displacement. In some embodiments, the first coupling segment, second coupling segment, and third coupling segment are different. In some embodiments, the particle is not washed between steps.

In some embodiments, the method can comprise a capping reaction. In some embodiments, the capping reaction comprises: contacting a capping oligonucleotide with the first extended oligonucleotide, the second extended oligonucleotide, the third extended oligonucleotide, the fourth extended oligonucleotide, the fifth extended oligonucleotide, the sixth extended oligonucleotide, the seventh extended oligonucleotide, and/or the eighth extended oligonucleotide, wherein the capping oligonucleotide is a single-stranded molecule comprising a 3' region capable of annealing to the 3' end of the first extended oligonucleotide, the second extended oligonucleotide, or the third extended oligonucleotide; and extending the first extended oligonucleotide, the second extended oligonucleotide, and/or the third extended oligonucleotide hybridized with the capping oligonucleotide, thereby generating a capped oligonucleotide.

The method can comprise contacting the particle with a single strand-specific exonuclease. In some embodiments, the plurality of oligonucleotides is non-covalently attached to the particle. In some embodiments, the plurality of oligonucleotides is covalently attached to the particle. In some embodiments, the plurality of oligonucleotides is covalently attached to the particle via a moiety comprising a labile bond. In some embodiments, said plurality of oligonucleotides are covalently attached to said particle via a moiety comprising a non-labile bond. In some embodiments, the labile bond comprises a thermally cleavable bond, a disulfide bond, a UV-sensitive bond, or any combination thereof. In some embodiments, the labile bond comprises an ester linkage, a vicinal diol linkage, a Diels-Alder linkage, a sulfone linkage, a silyl ester linkage, a glycosidic linkage, a peptide linkage, a phosphodiester linkage, or any combination thereof. In some embodiments, the particle comprises silica, glass, acrylamide, polyacrylamide, polypropylene, latex, nylon, plastic, ceramic, polystyrene, silicon, agarose, a cellulosic material, a metal, polydimethylsiloxane (PDMS), or any combination thereof. In some embodiments, the particle comprises a bead. In some embodiments, the bead comprises a plurality of beads is a disruptable bead.

Disclosed herein include methods of preparing a library of barcoded beads. In some embodiments, the method comprises: (a) providing a plurality of separate first bead populations, wherein each bead comprises a plurality of oligonucleotides each comprising an input primer; (b) contacting each separate first bead population with a first hairpin molecule, wherein the first hairpin molecule comprises: (i) an unpaired first 3' toehold domain complementary to the input primer, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; (c) extending the input primer hybridized to the first 3' toehold domain through the first paired stem domain of the first hairpin molecule, thereby displacing the 5' subdomain of the first hairpin molecule and forming a first extended oligonucleotide, wherein the first extended oligonucleotide of each separate first bead population comprises a different first barcode segment; (d) pooling the separate first bead populations to generate a first pooled bead population; (e) separating the first pooled bead population into a plurality of separate second bead populations; (f) contacting each separate second bead population with a second hairpin molecule, wherein the second hairpin molecule comprises: (i) an unpaired second 3' toehold domain complementary to the first coupling segment, (ii) a second paired stem domain formed by intramolecular nucleotide base pairing between a 3' subdomain of the second hairpin molecule and a 5' subdomain of the second hairpin molecule, wherein the second paired stem domain comprises a second coupling segment, a second barcode segment, and complements thereof, and (iii) a second hairpin loop domain; (g) extending the first coupling segment of the first extended oligonucleotide hybridized to the second 3' toehold domain through the second paired stem domain of the second hairpin molecule, thereby displacing the 5' subdomain of the second hairpin molecule and forming a second extended oligonucleotide, wherein the second extended oligonucleotide of each separate second bead population comprises a different second barcode segment; and (h) pooling the separate second bead populations to generate a second pooled bead population comprising a library of barcoded beads.

The method can further comprise repeating the following steps n times: separating the (n+1)th pooled bead population into a plurality of separate (n+2)th bead populations; contacting each separate (n+2)th bead population with a (n+2)th hairpin molecule, wherein the (n+2)th hairpin molecule comprises: (i) an unpaired (n+2)th 3' toehold domain complementary to the (n+1)th coupling segment, (ii) a (n+2)th paired stem domain formed by intramolecular nucleotide base pairing between a 3' subdomain of the (n+2)th hairpin molecule and a 5' subdomain of the (n+2)th hairpin molecule, wherein the (n+2)th paired stem domain comprises a (n+2)th coupling segment, a (n+2)th barcode segment, and complements thereof, and (iii) a (n+2)th hairpin loop domain; extending the (n+1)th coupling segment of the (n+1)th extended oligonucleotide hybridized to the (n+2)th 3' toehold domain through the (n+2)th paired stem domain of the (n+2)th hairpin molecule, thereby displacing the 5' subdomain of the (n+2)th hairpin molecule and forming a (n+2)th extended oligonucleotide, wherein the (n+2)th extended oligonucleotide of each separate (n+2)th bead population comprises a different (n+2)th barcode segment; and pooling the separate (n+2)th bead populations to generate a (n+2)th pooled bead population. In some embodiments, n is an integer between about 1 and about 8. The method can further comprise a capping reaction, comprising: contacting a capping oligonucleotide with the (n+2)th extended oligonucleotide, wherein the capping oligonucleotide is a single-stranded molecule comprising a 3' region capable of annealing to the 3' end of the (n+2)th extended oligonucleotide; and extending the (n+2)th extended oligonucleotide hybridized with the capping oligonucleotide, thereby generating a capped oligonucleotide, thereby generating a population of capped beads.

In some embodiments, the 5' subdomain of the first hairpin molecule comprises the first coupling segment and the first barcode segment. In some embodiments, the contacting steps and extending steps are performed in the presence of a polymerase having strand displacement activity and deoxyribonucleotide triphosphates (dNTPs). In some embodiments, the polymerase having strand displacement activity comprises phi29 DNA polymerase, Bst DNA polymerase, Bsu DNA polymerase, Klenow Fragment DNA polymerase, or any combination thereof. In some embodiments, the beads are not washed between steps.

In some embodiments, step (c) further comprises: displacing the first extended oligonucleotide from the first hairpin molecule through intramolecular nucleotide base pairing between the 3' subdomain of first hairpin molecule and the 5' subdomain of first hairpin molecule. In some embodiments, step (g) further comprises: displacing the second extended oligonucleotide from the second hairpin molecule through intramolecular nucleotide base pairing between the 3' subdomain of the second hairpin molecule and the 5' subdomain of the second hairpin molecule. In some embodiments, separating the first pooled bead population into a plurality of separate second bead populations comprises partitioning the first pooled bead population to a plurality of partitions. In some embodiments, the plurality of partitions comprises wells, microwells, tubes, vials, microcapsules, droplets, or any combination thereof. In some embodiments, the first extended oligonucleotide comprises the input primer, the first barcode segment, and the first coupling segment. In some embodiments, the second extended oligonucleotide comprises the input primer, the first barcode segment, the first coupling segment, the second barcode segment, and the second coupling segment.

In some embodiments, more than 80% of the second extended oligonucleotides comprise a first barcode segment and a second barcode segment. In some embodiments, more than 95% of the second extended oligonucleotides comprise a first barcode segment and a second barcode segment. In some embodiments, more than 99% of the second extended oligonucleotides comprise a first barcode segment and a second barcode segment. In some embodiments, a single first hairpin molecule can catalyze the extension of two or more different oligonucleotides. In some embodiments, a single first hairpin molecule can catalyze the extension of ten or more different oligonucleotides. In some embodiments, the ratio of the oligonucleotide to the first hairpin molecule at step (b) is at least 10:1. In some embodiments, the ratio of the oligonucleotide to the first hairpin molecule at step (b) is at least 100:1.

In some embodiments, the generation of the library of barcoded beads requires at least ten-fold less input nucleic acid as compared to a ligation-based method of bead barcoding. In some embodiments, the generation of the barcoded bead library requires at least hundred-fold less input nucleic acid as compared to a ligation-based method of bead barcoding. In some embodiments, steps (b), (c), (f) and/or (g) are performed under conditions that result in annealing, nucleic acid polymerization, and strand displacement. In some embodiments, the contacting steps and extending steps are performed isothermally. In some embodiments, the contacting steps and extending steps are performed at about 37° C. In some embodiments, the contacting steps and extending steps are performed isothermally or performed at greater than about 37° C., 50° C., or 60° C. In some embodiments, the contacting steps and extending steps comprise thermocycling. Thermocycling can comprise periodically adjusting the temperature of the contacting steps and/or extending steps. Thermocycling can be performed at about 37° C. to at about 60° C. In some embodiments, the first hairpin molecule and/or second hairpin molecule further comprises a 3' poly(dT) region, a dideoxy(T) (ddT), a nucleoside not capable of being 3' extended by a DNA polymerase, or any combination thereof. In some embodiments, the first hairpin molecule and/or second hairpin molecule further comprises an inverted-dT at its 3' end.

In some embodiments, the first hairpin molecule and/or second hairpin molecule further comprises a polymerase stopper, wherein the polymerase stopper terminates polymerization. In some embodiments, the polymerase stopper is located in the paired stem domain. In some embodiments, the polymerase stopper is located in the hairpin loop domain or between the paired stem domain and the hairpin loop domain. In some embodiments, the polymerase stopper comprises a cytosine 5' of the toehold domain, wherein each coupling segment and each barcode segment are comprised of adenine, thymine and cytosine, and wherein the deoxyribonucleotide triphosphates (dNTPs) comprise adenine, thymine and cytosine. In some embodiments, the polymerase stopper comprises a guanine 5' of the toehold domain, wherein each coupling segment and each barcode segment are comprised of adenine, thymine and guanine, and wherein the deoxyribonucleotide triphosphates (dNTPs) comprise adenine, thymine and guanine. In some embodiments, the polymerase stopper comprises a cytosine 5' of the toehold domain, wherein each coupling segment and each payload segment are comprised of adenine, thymine and cytosine, and wherein the deoxyribonucleotide triphosphates (dNTPs) comprise adenine, thymine and cytosine. In some embodiments, the polymerase stopper comprises a guanine 5' of the toehold domain, wherein each coupling segment and each payload segment are comprised of adenine, thymine and guanine, and wherein the deoxyribonucleotide triphosphates (dNTPs) comprise adenine, thymine and guanine. In some embodiments, the polymerase stopper comprises triethylene glycol (TEG), 18-atom hexaethylene glycol, adenylation, azide, digoxigenin, cholesteryl-TEG, 3-cyanovinylcarbazole (CNVK), iso-dG, iso-dC, an abasic site, a stable abasic site (e.g., 1',2'-dideoxy), a chemically trapped abasic site, or any combination thereof. The abasic site can comprise an apurinic site, an apyrimidinic site, or both. The abasic site can be generated by an alkylating agent or an oxidizing agent. The chemically trapped abasic site can comprise an abasic site reacted with alkoxyamine or sodium borohydride.

The method can comprise: (i) separating the second pooled bead population into a plurality of separate third bead populations; (j) contacting each separate third bead population with a third hairpin molecule, wherein the third hairpin molecule comprises: (i) an unpaired third 3' toehold domain complementary to the second coupling segment, (ii) a third paired stem domain formed by intramolecular nucleotide base pairing between a 3' subdomain of the third hairpin molecule and a 5' subdomain of the third hairpin molecule, wherein the third paired stem domain comprises a third coupling segment, a third barcode segment, and complements thereof, and (iii) a third hairpin loop domain; (k) extending the second coupling segment of the second extended oligonucleotide hybridized to the third 3' toehold domain through the third paired stem domain of the third hairpin molecule, thereby displacing the 5' subdomain of the third hairpin molecule and forming a third extended oligonucleotide, wherein the third extended oligonucleotide of each separate third bead population comprises a different third barcode segment; and (l) pooling the separate third bead populations to generate a third pooled bead population.

The method can comprise: (m) separating the third pooled bead population into a plurality of separate fourth bead populations; (n) contacting each separate fourth bead population with a fourth hairpin molecule, wherein the fourth hairpin molecule comprises: (i) an unpaired fourth 3' toehold domain complementary to the third coupling segment, (ii) a fourth paired stem domain formed by intramolecular nucleotide base pairing between a 3' subdomain of the fourth hairpin molecule and a 5' subdomain of the fourth hairpin molecule, wherein the fourth paired stem domain comprises a fourth coupling segment, a fourth barcode segment, and complements thereof, and (iii) a fourth hairpin loop domain; (o) extending the third coupling segment of the third extended oligonucleotide hybridized to the fourth 3' toehold domain through the fourth paired stem domain of the fourth hairpin molecule, thereby displacing the 5' subdomain of the fourth hairpin molecule and forming a fourth extended oligonucleotide, wherein the fourth extended oligonucleotide of each separate fourth bead population comprises a different fourth barcode segment; and (p) pooling the separate fourth bead populations to generate a fourth pooled bead population comprising a library of barcoded beads.

The method can comprise: (q) separating the fourth pooled bead population into a plurality of separate fifth bead populations; (r) contacting each separate fifth bead population with a fifth hairpin molecule, wherein the fifth hairpin molecule comprises: (i) an unpaired fifth 3' toehold domain complementary to the fourth coupling segment, (ii) a fifth paired stem domain formed by intramolecular nucleotide base pairing between a 3' subdomain of the fifth hairpin molecule and a 5' subdomain of the fifth hairpin molecule, wherein the fifth paired stem domain comprises a fifth coupling segment, a fifth barcode segment, and complements thereof, and (iii) a fifth hairpin loop domain; (s) extending the fourth coupling segment of the fourth extended oligonucleotide hybridized to the fifth 3' toehold domain through the fifth paired stem domain of the fifth hairpin molecule, thereby displacing the 5' subdomain of the fifth hairpin molecule and forming a fifth extended oligonucleotide, wherein the fifth extended oligonucleotide of each separate fifth bead population comprises a different fifth barcode segment; and (t) pooling the separate fifth bead populations to generate a fifth pooled bead population comprising a library of barcoded beads.

The method can comprise: (u) separating the fifth pooled bead population into a plurality of separate sixth bead populations; (v) contacting each separate sixth bead population with a sixth hairpin molecule, wherein the sixth hairpin molecule comprises: (i) an unpaired sixth 3' toehold domain complementary to the fifth coupling segment, (ii) a sixth paired stem domain formed by intramolecular nucleotide base pairing between a 3' subdomain of the sixth hairpin molecule and a 5' subdomain of the sixth hairpin molecule, wherein the sixth paired stem domain comprises a sixth coupling segment, a sixth barcode segment, and complements thereof, and (iii) a sixth hairpin loop domain; (w) extending the fifth coupling segment of the fifth extended oligonucleotide hybridized to the sixth 3' toehold domain through the sixth paired stem domain of the sixth hairpin molecule, thereby displacing the 5' subdomain of the sixth hairpin molecule and forming a sixth extended oligonucleotide, wherein the sixth extended oligonucleotide of each separate sixth bead population comprises a different sixth barcode segment; and (x) pooling the separate sixth bead populations to generate a sixth pooled bead population comprising a library of barcoded beads.

The method can comprise: (y) separating the sixth pooled bead population into a plurality of separate seventh bead populations; (z) contacting each separate seventh bead population with a seventh hairpin molecule, wherein the seventh hairpin molecule comprises: (i) an unpaired seventh 3' toehold domain complementary to the sixth coupling segment, (ii) a seventh paired stem domain formed by intramolecular nucleotide base pairing between a 3' subdomain of the seventh hairpin molecule and a 5' subdomain of the seventh hairpin molecule, wherein the seventh paired stem domain comprises a seventh coupling segment, a seventh barcode segment, and complements thereof, and (iii) a seventh hairpin loop domain; (aa) extending the sixth coupling segment of the sixth extended oligonucleotide hybridized to the seventh 3' toehold domain through the seventh paired stem domain of the seventh hairpin molecule, thereby displacing the 5' subdomain of the seventh hairpin molecule and forming a seventh extended oligonucleotide, wherein the seventh extended oligonucleotide of each separate seventh bead population comprises a different seventh barcode segment; and (bb) pooling the separate seventh bead populations to generate a seventh pooled bead population comprising a library of barcoded beads.

The method can comprise: (cc) separating the seventh pooled bead population into a plurality of separate eighth bead populations; (dd) contacting each separate eighth bead population with an eighth hairpin molecule, wherein the eighth hairpin molecule comprises: (i) an unpaired eighth 3' toehold domain complementary to the seventh coupling segment, (ii) an eighth paired stem domain formed by intramolecular nucleotide base pairing between a 3' subdomain of the eighth hairpin molecule and a 5' subdomain of the eighth hairpin molecule, wherein the eighth paired stem domain comprises an eighth coupling segment, an eighth barcode segment, and complements thereof, and (iii) an eighth hairpin loop domain; (ee) extending the seventh coupling segment of the seventh extended oligonucleotide hybridized to the eighth 3' toehold domain through the eighth paired stem domain of the eighth hairpin molecule, thereby displacing the 5' subdomain of the eighth hairpin molecule and forming an eighth extended oligonucleotide, wherein the eighth extended oligonucleotide of each separate eighth bead population comprises a different eighth barcode segment; and (ff) pooling the separate eighth bead populations to generate an eighth pooled bead population comprising a library of barcoded beads.

In some embodiments, each separate first bead population is contacted with a first hairpin molecule comprising a different first barcode segment, and wherein each separate second bead population is contacted with a second hairpin molecule comprising a different second barcode segment. In some embodiments, each separate third bead population is contacted with a third hairpin molecule comprising a different third barcode segment, and wherein each separate fourth bead population is contacted with a fourth hairpin molecule comprising a different fourth barcode segment. In some embodiments, the first barcode segment is selected from a first set of barcode segments, wherein the second barcode segment is selected from a second set of barcode segments. In some embodiments, the first set of barcode segments and the second set of barcode segments are identical. In some embodiments, the first set of barcode segments and the second set of barcode segments are different. In some embodiments, the third barcode segment is selected from a third set of barcode segments, and wherein the fourth barcode segment is selected from a fourth set of barcode segments. In some embodiments, the first set of barcode segments, the second set of barcode segments, the third set of barcode segments, and/or the fourth set of barcode segments are identical. In some embodiments, the first set of barcode segments, the second set of barcode segments, the third set of barcode segments, and/or the fourth set of barcode segments are different. In some embodiments, the first set of barcode segments, the second set of barcode segments, the third set of barcode segments, and/or the fourth set of barcode segments have identical lengths. In some embodiments, the first set of barcode segments, the second set of barcode segments, the third set of barcode segments, and/or the fourth set of barcode segments have different lengths. In some embodiments, a barcode segment comprises about 1 nucleotide to about 50 nucleotides. In some embodiments, a barcode segment comprises about 5 nucleotides.

In some embodiments, the oligonucleotide comprises a barcode comprising the first barcode segment, the second barcode segment, the third barcode segment, and/or the fourth barcode segment. In some embodiments, there are m separate first bead populations, wherein there are n separate second bead populations, and wherein the second pooled bead population is capable of comprising m*n unique barcodes. In some embodiments, there are o separate third bead populations, and wherein the third pooled bead population is capable of comprising m*n*o unique barcodes. In some embodiments, there are p separate fourth bead populations, and wherein the fourth pooled bead population is capable of comprising m*n*o*p unique barcodes. In some embodiments, the plurality of oligonucleotides of the same bead comprise the same barcode, and wherein oligonucleotides on different beads comprise different barcodes. In some embodiments, the plurality of oligonucleotides of the same bead comprise identical first barcode segments and identical second barcode segments. In some embodiments, the plurality of oligonucleotides of the same bead comprise identical first barcode segments, identical second barcode segments, identical third barcode segments, and identical fourth barcode segments. In some embodiments, two beads do not comprise the same combination of first barcode segments, second barcode segments, third barcode segments, and/or fourth barcode segments.

In some embodiments, each first hairpin molecule comprises an identical first coupling segment, and wherein each second hairpin molecule comprises an identical second coupling segment. In some embodiments, each third hairpin molecule comprises an identical third coupling segment, and wherein each fourth hairpin molecule comprises an identical fourth coupling segment. In some embodiments, the first coupling segment, second coupling segment, third coupling segment, and/or fourth coupling segment are different. In some embodiments, a coupling segment comprises about 1 nucleotide to about 50 nucleotides. In some embodiments, a coupling segment comprises about 9 nucleotides.

In some embodiments, the method can comprise a capping reaction. In some embodiments, the capping reaction comprises: contacting a capping oligonucleotide with the first extended oligonucleotide, the second extended oligonucleotide, the third extended oligonucleotide, the fourth extended oligonucleotide, the fifth extended oligonucleotide, the sixth extended oligonucleotide, the seventh extended oligonucleotide, and/or the eighth extended oligonucleotide, wherein the capping oligonucleotide is a single-stranded molecule comprising a 3' region capable of annealing to the 3' end of the first extended oligonucleotide, the second extended oligonucleotide, the third extended oligonucleotide, or the fourth extended oligonucleotide; and extending the first extended oligonucleotide, the second extended oligonucleotide, the third extended oligonucleotide, and/or the fourth extended oligonucleotide hybridized with the capping oligonucleotide, thereby generating a capped oligonucleotide, thereby generating a population of capped beads. In some embodiments, the capping oligonucleotide comprises one or more of a unique molecular identifier (UMI), a primer sequence, a primer annealing sequence, an attachment sequence, a sequencing primer sequence, or any combination thereof. In some embodiments, the capped oligonucleotide is double-stranded. In some embodiments, the method comprises contacting the population of capped beads with a single strand-specific exonuclease. In some embodiments, the single strand-specific exonuclease is Exonuclease I.

In some embodiments, the beads comprise magnetic beads, glass beads, cellulose beads, epichlorohydrin-cross-linked-dextran beads, polyacrylamide beads, agarose beads, polystyrene beads, gel-based beads, or any combination thereof. In some embodiments, the beads comprise hydrogel beads. In some embodiments, the second pooled bead population, the third pooled bead population, and/or the fourth pooled bead population comprise at least 1,000 beads. In some embodiments, each bead comprises at least 1,000 oligonucleotides. In some embodiments, the oligonucleotide comprises single-stranded DNA.

Disclosed herein include compositions for use in nucleic acid barcoding. In some embodiments, the composition comprises: a first hairpin molecule, comprising (i) a first 3' toehold domain, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; and a gel bead releasably attached to a plurality of oligonucleotides each comprising an input primer hybridized to the 3' toehold domain of a first hairpin molecule, wherein the input primer is complementary to the 3' toehold domain of the first hairpin molecule.

Disclosed herein include compositions for use in nucleic acid barcoding. In some embodiments, the composition comprises: a first hairpin molecule, comprising (i) a first 3' toehold domain, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; and a plurality of gel beads releasably attached to a plurality of oligonucleotides each comprising an input primer hybridized to the 3' toehold domain of a first hairpin molecule, wherein the input primer is complementary to the 3' toehold domain of the first hairpin molecule.

In some embodiments, the oligonucleotides are releasable upon application of a stimulus, In some embodiments, the gel beads are degradable upon application of a chemical stimulus. In some embodiments, the gel bead comprises chemically reducible cross-linkers. In some embodiments, the chemically reducible cross-linkers comprise disulfide linkages. In some embodiments, the chemical stimulus comprises a reducing agent. In some embodiments, the reducing agent comprises dithiothreitol (DTT) and/or tris(2-carboxyethyl)phosphine (TCEP). In some embodiments, the gel bead does not comprise a photo-cleavable linker. In some embodiments, the oligonucleotides are attached to the gel bead by an acrydite moiety. In some embodiments, the oligonucleotides comprise single-stranded DNA. In some embodiments, the oligonucleotides comprise double-stranded DNA. In some embodiments, the oligonucleotides comprise deoxyuridine. In some embodiments, the stimulus comprises USER (Uracil-Specific Excision Reagent) enzyme.

In some embodiments, the plurality of gel beads is formed upon polymerization of molecular precursors within a plurality of droplets. In some embodiments, the molecular precursors comprise acrylamide and N,N'-Bis(acryloyl)cystamine (BAC). In some embodiments, the molecular precursors comprise acrylamide and bisacrylamide. In some embodiments, the molecular precursors comprise acrydite-modified oligonucleotides. In some embodiments, the plurality of gel beads comprises at least 1,000 gel beads. In some embodiments, the plurality of gel beads have substantially uniform cross-sectional dimensions. In some embodiments, the plurality of gel beads has a coefficient of variation in cross-sectional dimension of less than 30%. In some embodiments, a gel bead has a cross-sectional dimension between about 10 micrometers and about 100 micrometers. In some embodiments, a gel bead has a cross-sectional dimension between about 0.1 micrometers and about 10 micrometers.

In some embodiments, the oligonucleotides comprise an immobilization sequence. In some embodiments, the immobilization sequence is P5. In some embodiments, the 5' subdomain of the first hairpin molecule comprises the first coupling segment and the first barcode segment. In some embodiments, the first hairpin molecule further comprises a 3' poly(dT) region. In some embodiments, the first hairpin molecule further comprises an inverted-dT at its 3' end. In some embodiments, the first hairpin molecule further comprises a polymerase stopper, wherein the polymerase stopper terminates polymerization. In some embodiments, the polymerase stopper is located in the paired stem domain. In some embodiments, the polymerase stopper is located in the hairpin loop domain or between the paired stem domain and the hairpin loop domain. In some embodiments, the polymerase stopper comprises a cytosine 5' of the toehold domain, wherein each coupling segment and each barcode segment are comprised of adenine, thymine and cytosine. In some embodiments, the polymerase stopper comprises a guanine 5' of the toehold domain, wherein each coupling segment and each barcode segment are comprised of adenine, thymine and guanine.

In some embodiments, a barcode segment comprises about 1 nucleotide to about 50 nucleotides. In some embodiments, a barcode segment comprises about 5 nucleotides. In some embodiments, at least two oligonucleotides are hybridized to first hairpin molecules comprising different first barcode segments, wherein said at least two oligonucleotides hybridized to first hairpin molecules comprising different first barcode segments are located in separate partitions. In some embodiments, the separate partitions comprise wells, microwells, tubes, vials, microcapsules, droplets, or any combination thereof. In some embodiments, a coupling segment comprises about 1 nucleotide to about 50 nucleotides. In some embodiments, a coupling segment comprises about 9 nucleotides. In some embodiments, at least 100,000 oligonucleotides are releasably attached to a gel bead. In some embodiments, each of the at least 100,000 oligonucleotides comprises an identical bead barcode sequence. In some embodiments, the identical bead barcode sequence is different across different gel beads. In some embodiments, the oligonucleotides comprise unique identifiers that are different across said oligonucleotides.

BRIEF DESCRIPTION OF THE DRAWINGS

FIGS. 3A-3B depict non-limiting exemplary nucleic acids employed in the methods provided herein.

FIG. 5A is a schematic illustration showing a non-limiting exemplary embodiment of a hydrogel bead composition prepared with acrylamide, N,N-bis(acryloyl)cystamine, and acrydite-modified DNA.

FIG. 5B is a schematic illustration showing a non-limiting exemplary embodiment of USER enzyme-mediated cleavage of a particle-associated oligonucleotide comprising deoxyuridine.

DETAILED DESCRIPTION

Figure 1A:
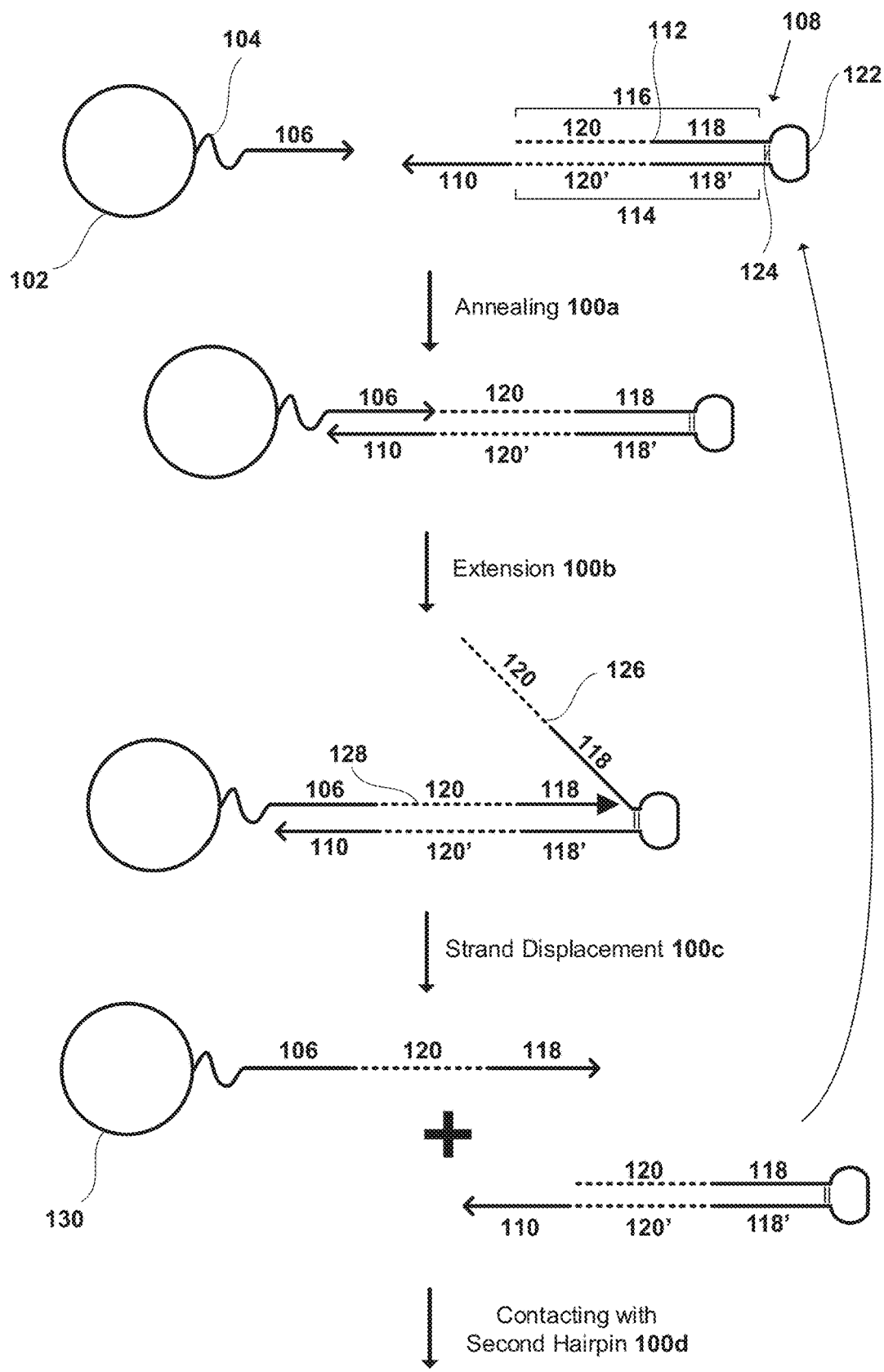
FIGS. 1A-1B are schematic illustrations of a non-limiting exemplary workflow for extending particle-associated oligonucleotides.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include methods of extending particle-associated oligonucleotides. In some embodiments, the method comprises: (a) providing a particle comprising a plurality of oligonucleotides each comprising an input primer; (b) contacting the particle with a first hairpin molecule, wherein the first hairpin molecule comprises: (i) an unpaired first 3' toehold domain complementary to the input primer, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first payload segment, and complements thereof, and (iii) a first hairpin loop domain; and (c) extending the input primer hybridized to the first 3' toehold domain through the first paired stem domain of the first hairpin molecule, thereby displacing the 5' subdomain of the first hairpin molecule and forming a first extended oligonucleotide comprising the input primer, the first payload segment and the first coupling segment.

Disclosed herein include methods of preparing a library of barcoded beads. In some embodiments, the method comprises: (a) providing a plurality of separate first bead populations, wherein each bead comprises a plurality of oligonucleotides each comprising an input primer; (b) contacting each separate first bead population with a first hairpin molecule, wherein the first hairpin molecule comprises: (i) an unpaired first 3' toehold domain complementary to the input primer, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; (c) extending the input primer hybridized to the first 3' toehold domain through the first paired stem domain of the first hairpin molecule, thereby displacing the 5' subdomain of the first hairpin molecule and forming a first extended oligonucleotide, wherein the first extended oligonucleotide of each separate first bead population comprises a different first barcode segment; (d) pooling the separate first bead populations to generate a first pooled bead population; (e) separating the first pooled bead population into a plurality of separate second bead populations; (f) contacting each separate second bead population with a second hairpin molecule, wherein the second hairpin molecule comprises: (i) an unpaired second 3' toehold domain complementary to the first coupling segment, (ii) a second paired stem domain formed by intramolecular nucleotide base pairing between a 3' subdomain of the second hairpin molecule and a 5' subdomain of the second hairpin molecule, wherein the second paired stem domain comprises a second coupling segment, a second barcode segment, and complements thereof, and (iii) a second hairpin loop domain; (g) extending the first coupling segment of the first extended oligonucleotide hybridized to the second 3' toehold domain through the second paired stem domain of the second hairpin molecule, thereby displacing the 5' subdomain of the second hairpin molecule and forming a second extended oligonucleotide, wherein the second extended oligonucleotide of each separate second bead population comprises a different second barcode segment; and (h) pooling the separate second bead populations to generate a second pooled bead population comprising a library of barcoded beads.

Disclosed herein include compositions for use in nucleic acid barcoding. In some embodiments, the composition comprises: a first hairpin molecule, comprising (i) a first 3' toehold domain, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; and a gel bead releasably attached to a plurality of oligonucleotides each comprising an input primer hybridized to the 3' toehold domain of a first hairpin molecule, wherein the input primer is complementary to the 3' toehold domain of the first hairpin molecule.

Disclosed herein include compositions for use in nucleic acid barcoding. In some embodiments, the composition comprises: a first hairpin molecule, comprising (i) a first 3' toehold domain, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; and a plurality of gel beads releasably attached to a plurality of oligonucleotides each comprising an input primer hybridized to the 3' toehold domain of a first hairpin molecule, wherein the input primer is complementary to the 3' toehold domain of the first hairpin molecule.

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

Efficient Combinatorial Bead Barcoding

The production of barcoded particles (e.g., DNA-barcoded microparticles) is of interest for many biotechnology applications. A DNA barcode is a sequence of DNA bases, and in applications it is useful to have DNA barcodes attached to microparticles in a way that ensures each particle receives many copies of the same DNA sequence, yet no two particles share the same sequence. In recent years such DNA-barcoded microparticles have enabled important advances in genomics. However, the manufacturing of DNA-barcoded microparticles is challenging due to a number of technical obstacles. For example, extension of barcodes on hydrogel beads in a manner that is efficient and cheap is one of the key challenges in manufacturing barcoded beads. Among the aforementioned technical obstacles is a requirement for high numbers of DNA barcodes for use with current DNA extension methods, and the need for washing beads between steps to prevent non-specific reactions from occurring. These requirements lead to considerable expense in labor and reagents. Furthermore, current methods for manufacturing DNA barcoded microparticles may only allow for specific DNA barcodes to be attached to microparticles, or for specific types of microparticles to be used. Thus, available methods of current DNA extension reactions employed for the purpose of combinatorially barcoding beads suffer from the following issues: (1) a high amount of DNA barcodes are necessary, at least 1:1 to the DNA being extended, which means that most libraries for obtaining >1M barcodes end up costing at least $10,000, and this becomes a recurring expense as the DNA is consumed during bead production; (2) the beads need to be washed between steps to prevent non-specific reactions from occurring, which in addition to labor costs, also significantly increases cost as enzymes and other reagents need to be re-added between each step; and (3) efficiency issues—because split pool relies in a concatenation of reactions, high efficiency is very important, otherwise a significant fraction of the beads will have incomplete barcodes at the end of the process.

There are provided, in some embodiments, methods, systems, and compositions which solve the above-mentioned problems in the art. Provided herein are novel methods for producing DNA barcoded microparticles employing a modified version of the "Primer Extension Reaction" (PER) method disclosed in Kishi et al. ("Programmable autonomous synthesis of single-stranded DNA." Nature chemistry 10.2 (2018): 155). Provided herein are methods employing PER-catalyzed extension of oligonucleotides to barcode particles. Kishi discloses uses for their reaction primarily focused in molecular computing. The PER method disclosed by Kishi suffers from various limitations, as it does not work in a combinatorial fashion but rather extends oligonucleotides in a fixed programmed manner. Provided herein, in some embodiments, is a novel version of PER wherein the hairpin molecule comprises additional components (relative to Kishi) which enable compatibility with split-pool methodology, enable combinatorial synthesis, and thereby the enable the particle barcoding methods and compositions provided herein. Provided herein is the first demonstration of split-pool barcoding using PER. In some embodiments, PER-catalyzed oligonucleotide extension uses over a hundred times less DNA as compared to previous primer extension reactions, requires no washing between steps, and is highly efficient and specific. The results provided herein show that the compositions and methods provided herein successfully employ PER-catalyzed reactions to barcode particles (e.g. HB) extremely efficiently, with great reduction in labor and time as compared to other methods. In some embodiments, these methods result in at least a ten-fold reduction in cost. As compared to the barcoding methods employed by Klein et al ("Droplet barcoding for single-cell transcriptomics applied to embryonic stem cells." Cell 161.5 (2015): 1187-1201.) the disclosed methods can use over a hundred times less DNA, require no washing between steps, and are highly efficient and specific.

Figure 4:
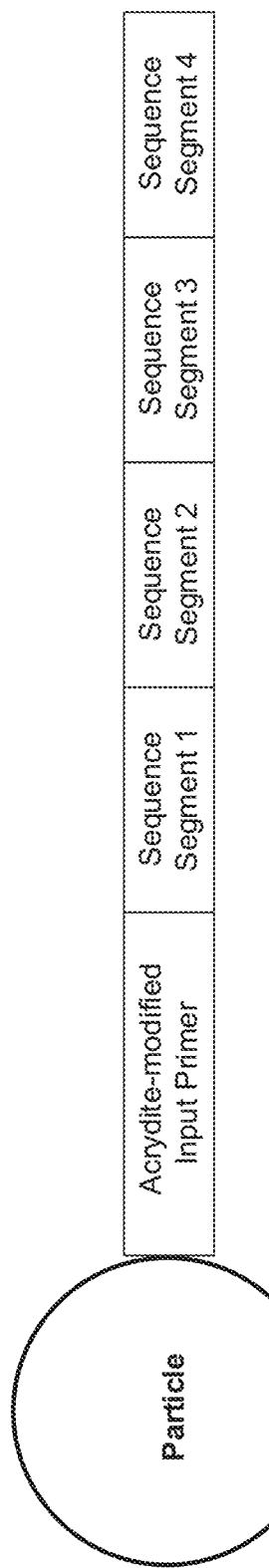
FIG. 4 is a schematic illustration showing a non-limiting exemplary embodiment of a particle-associated oligonucleotide prepared according to the methods provided herein.

There are provided, in some embodiments, methods of extending particle-associated oligonucleotides. Methods of extending particle-associated oligonucleotides can employ PER-catalyzed extension (e.g., employing an input primer and a first hairpin molecule as depicted in FIG. 1). There are provided, in some embodiments, methods of preparing a library of barcoded beads. Methods of preparing a library of barcoded beads can employ a PER-catalyzed extension of particle-associated oligonucleotides and/or split-pooling approaches (e.g., employing an input primer, a first hairpin molecule, and split-pooling as depicted in FIG. 2). FIG. 4 is a schematic illustration showing a non-limiting exemplary embodiment of a particle-associated oligonucleotide prepared according to the methods provided herein. The particle can be a redox-cleavable, DNA barcoded hydrogel microsphere. Particles (e.g. beads) prepared according to the methods provided herein can comprise a plurality (e.g., billions) of oligonucleotides. In some embodiments, oligonucleotides of one bead can be identical to one another. In some embodiments, no two beads share the same oligonucleotide sequence. The particle can comprise a gel bead (e.g., a hydrogel bead, hydrogel microspheres, "HB"). The plurality of oligonucleotides can be releasably attached to the gel bead. The gel beads can comprise disulfide linkages that can be degradable upon application of a chemical stimulus (e.g, a reducing agent). The oligonucleotides can be single-stranded or double-stranded. The single stranded DNA can be attached to the hydrogel bead by an acrydite moiety which is crosslinked with the hydrogel. The oligonucleotides can comprise deoxyuridine and said oligonucleotides can be releasable upon application of a stimulus (e.g., USER enzyme). The particle (e.g. bead)-associated oligonucleotide can comprise an acrydite-modified input primer, a first sequence segment, a second sequence segment, a third sequence segment, and a fourth sequence segment. In some embodiments, sequence segment comprises a payload segment (e.g., a barcode segment) and a coupling segment. For example, the first sequence segment can comprise a first payload segment (e.g., a first barcode segment) and a first coupling segment, the second sequence segment can comprise a second payload segment (e.g., a second barcode segment) and a second coupling segment, the third sequence segment can comprise a third payload segment (e.g., a third barcode segment) and a third coupling segment, and/or the fourth sequence segment can comprise a fourth payload segment (e.g., a fourth barcode segment) and a fourth coupling segment. A combination of barcode segments (e.g., a first barcode segment, a second barcode segment, and a third barcode segment) can collectively form a barcode. Each of said barcode segments can be combinatorially added during successive split-pool reactions. In some embodiments, the oligonucleotide comprises a barcode. In some embodiments, the barcode is a bead barcode. In some embodiments, a particle (e.g., bead) comprises a plurality of oligonucleotides, and each of said oligonucleotides comprise an identical barcode (e.g. bead barcode). There are provided, in some embodiments, methods of making a population (e.g., a library) of barcoded beads. In some embodiments, the oligonucleotides associated with two beads of the population of beads (e.g., a library of barcode beads) comprise different bead barcodes. In some embodiments, bead barcodes are unique to each bead within the population of beads. In some embodiments, each bead is coated with DNA that has the same barcode segment combination, but no two beads have the same barcode. In some embodiment, each bead oligonucleotide comprises the same capping sequence. In some embodiments, the oligonucleotides further comprise a unique molecular identifier (UMI). In some such embodiments, the UMI is different across said oligonucleotides.

The methods, compositions and systems described herein are particularly useful for attaching barcodes, and particularly barcode nucleic acid sequences, to sample materials and components of those sample materials. The methods, compositions, devices, and kits of this disclosure may be used with any suitable sample or species. A sample (e.g., sample material, component of a sample material, fragment of a sample material, etc.) or species can be, for example, any substance used in sample processing, such as a reagent or an analyte.

The methods and compositions provided herein can be employed for sample processing, particularly for nucleic acid analysis applications, generally, and nucleic acid sequencing applications, in particular. Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue. In some embodiments, the DNA-barcoded microparticles provided herein can be used to enable single-cell gene expression measurements. In some embodiments, the DNA-barcoded microparticles provided herein can be employed in barcoding cells.

The methods and compositions of this disclosure may be useful for a variety of different molecular biology applications including, but not limited to, nucleic acid sequencing, protein sequencing, nucleic acid quantification, sequencing optimization, detecting gene expression, quantifying gene expression, epigenetic applications, and single-cell analysis of genomic or expressed markers. Moreover, the methods and compositions of this disclosure have numerous medical applications including identification, detection, diagnosis, treatment, staging of, or risk prediction of various genetic and non-genetic diseases and disorders including cancer.

PER-Catalyzed Extension of Particle-Associated Oligonucleotides

Figure 1B:
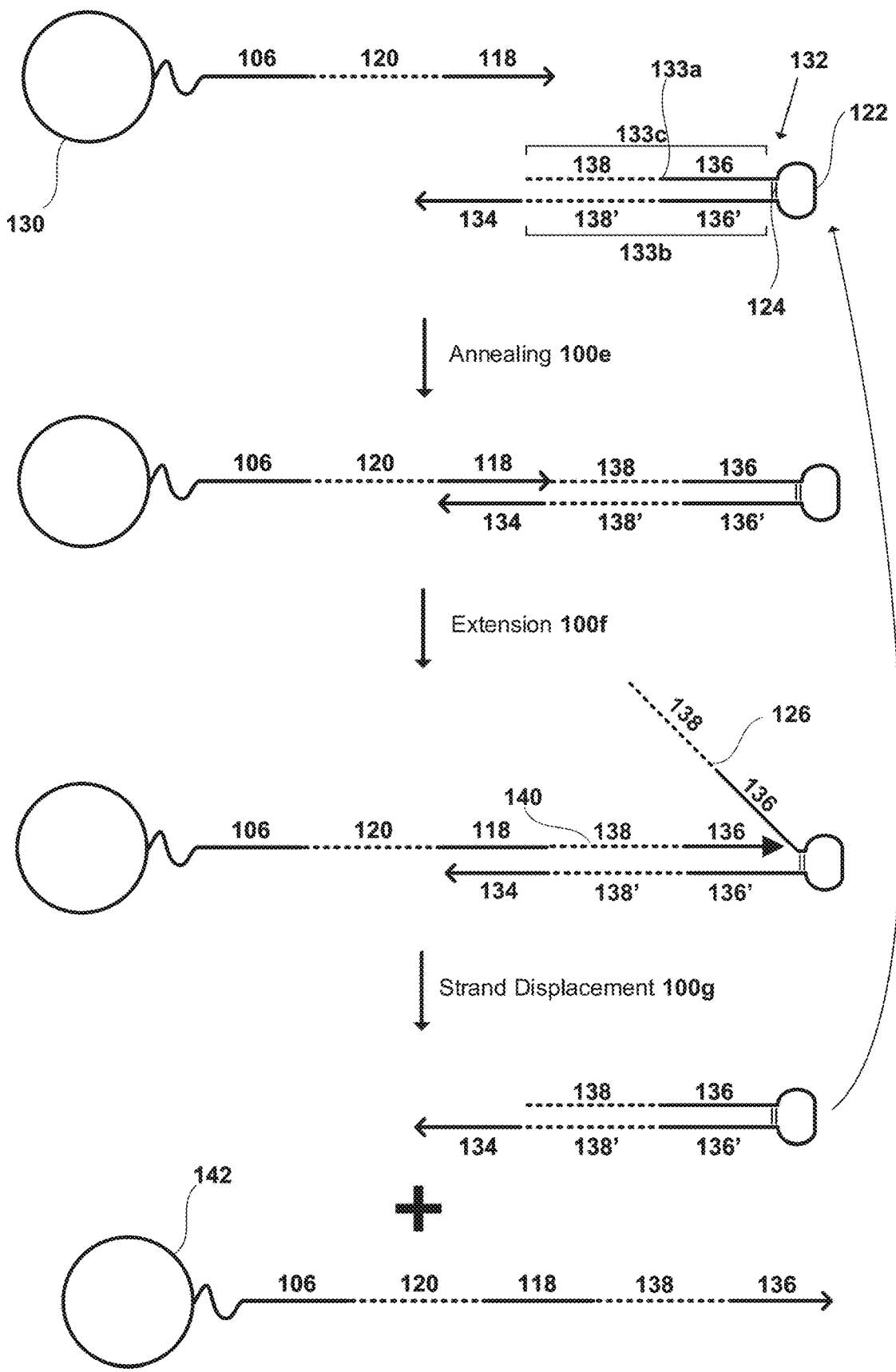

The present disclosure provides, in some embodiments, PER-catalyzed oligonucleotide extension reactions that employ catalytic nucleic acid molecules ("catalytic PER molecules"), such as hairpin molecules, for the isothermal synthesis of single-stranded DNA (ssDNA). FIGS. 1A-1B are schematic illustrations of a non-limiting exemplary workflow for extending particle-associated oligonucleotides according to the methods provided herein. Methods of extending particle-associated oligonucleotides can employ PER-catalyzed extension. The workflow can comprise providing a particle (e.g., bead) 102 comprising a plurality of particle-associated oligonucleotides 104. The oligonucleotides can comprise an input primer 106. The workflow can comprise providing a first hairpin molecule 108. First hairpin molecule 108 can comprise an unpaired first 3' toehold domain 110 complementary to input primer 106. First hairpin molecule 108 can comprise a first paired stem domain 112 formed by intramolecular nucleotide base pairing between a 3' subdomain 114 of the first hairpin molecule 108 and a 5' subdomain 116 of the first hairpin molecule 108. First paired stem domain 112 can comprise first coupling segment 118 and first coupling segment complement 118'. First paired stem domain 112 can comprise first payload segment 120 and first payload segment complement 120'. In some embodiments, the first payload segment 120 comprises a first barcode segment. First hairpin molecule 108 can comprise a linkage domain (e.g. hairpin loop domain 122) and a polymerase stopper 124.

The workflow can comprise contacting the particle (e.g., bead) 102 and first hairpin molecule 108. In some embodiments, the first 3' toehold domain 110 hybridizes to input primer 106 (step 100a). In some embodiments, one or more steps of the workflow (e.g., contacting and extending steps) are performed under condition(s) that result in annealing, nucleic acid polymerization, and strand displacement. In some embodiments, one or more steps of the workflow (e.g., contacting and extending steps) are performed in the presence of a polymerase having strand displacement activity (e.g., phi29 DNA polymerase, Bst DNA polymerase, Bsu DNA polymerase, large fragment, or any combination thereof) and deoxyribonucleotide triphosphates (dNTPs). In some embodiments, the workflow comprises extending the input primer 106 hybridized to the first 3' toehold domain 110 through the first paired stem domain 112 of the first hairpin molecule 108 (step 100b), thereby generating a displaced 5' subdomain 126 and forming a first extended oligonucleotide 128. The first extended oligonucleotide 128 can comprise input primer 106, the first payload segment 120 and the first coupling segment 118. In some embodiments branch migration displaces first extended oligonucleotide 128 (step 100c), thereby generating first hairpin molecule 108 and first barcoded particle 130. In some embodiments first hairpin molecule 108 can subsequently catalyze additional extension reactions.

The workflow can comprise contacting first barcoded particle 130 with and a second hairpin molecule 132 (step 100d). Second hairpin molecule 132 can comprise an unpaired second 3' toehold domain 134 complementary to first coupling segment 118. Second hairpin molecule 132 can comprise a second paired stem domain 133a formed by intramolecular nucleotide base pairing between a 3' subdomain 133b of second hairpin molecule 132 and a 5' subdomain 133c of the second hairpin molecule 132. Second paired stem domain 133a can comprise second coupling segment 136 and second coupling segment complement 136'. Second paired stem domain 133a can comprise second payload segment 138 and second payload segment complement 138'. In some embodiments, the second payload segment 138 comprises a second barcode segment. Second hairpin molecule 132 can comprise a linkage domain (e.g. hairpin loop domain 122) and a polymerase stopper 124.

In some embodiments, the second 3' toehold domain 134 hybridizes to first coupling segment 118 (step 100e). In some embodiments, the workflow comprises extending first coupling segment 118 hybridized to the second 3' toehold domain 134 through the second paired stem domain 133a of the second hairpin molecule 132 (step 100f), thereby generating a displaced 5' subdomain 126 and forming a second extended oligonucleotide 140. The second extended oligonucleotide 140 can comprise input primer 106, the first payload segment 120, the first coupling segment 118, second payload segment 138, and second coupling segment 136. In some embodiments branch migration displaces second extended oligonucleotide 140 (step 100g), thereby generating second hairpin molecule 132 and second barcoded particle 142. In some embodiments second hairpin molecule 132 can subsequently catalyze additional PER-catalyzed extension reactions.

In some embodiments the workflow is performed isothermally. In some embodiments, the workflow does not comprise washing steps. The second barcoded particle 142 can undergo additional PER-catalyzed extensions (e.g., employing a third hairpin molecule comprising an unpaired 3' toehold domain complementary to the second coupling segment). The workflow can further comprise the second barcoded particle undergoing a capping reaction with a capping oligonucleotide as described herein, thereby incorporating the sequence of the capping oligonucleotide into the particle-associated oligonucleotide. The workflow can further comprise treatment of the barcoded particle with a single-strand specific exonuclease (e.g., exonuclease I). The workflow can further comprise a step denaturing the particle-associated oligonucleotides, generating a single-stranded particle-associated oligonucleotides.

There are provided, in some embodiments, methods of extending particle-associated oligonucleotides. In some embodiments, the method comprises: (a) providing a particle comprising a plurality of oligonucleotides each comprising an input primer; (b) contacting the particle with a first hairpin molecule, wherein the first hairpin molecule comprises: (i) an unpaired first 3' toehold domain complementary to the input primer, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first payload segment, and complements thereof, and (iii) a first hairpin loop domain; and (c) extending the input primer hybridized to the first 3' toehold domain through the first paired stem domain of the first hairpin molecule, thereby displacing the 5' subdomain of the first hairpin molecule and forming a first extended oligonucleotide comprising the input primer, the first payload segment and the first coupling segment. The method can comprise: (d) contacting the particle with a second hairpin molecule, wherein the second hairpin molecule comprises: (i) an unpaired second 3' toehold domain complementary to the first coupling segment, (ii) a second paired stem domain formed by intramolecular nucleotide base pairing between a 3' subdomain of the second hairpin molecule and a 5' subdomain of the second hairpin molecule, wherein the second paired stem domain comprises a second coupling segment, a second payload segment, and complements thereof, and (iii) a second hairpin loop domain; and (e) extending the first coupling segment of the first extended oligonucleotide hybridized to the second 3' toehold domain through the second paired stem domain of the second hairpin molecule, thereby displacing the 5' subdomain of the second hairpin molecule and forming a second extended oligonucleotide comprising the first coupling segment, the second payload segment and the second coupling segment. The method can comprise: (f) contacting the particle with a third hairpin molecule, wherein the third hairpin molecule comprises: (i) an unpaired third 3' toehold domain complementary to the second coupling segment, (ii) a third paired stem domain formed by intramolecular nucleotide base pairing between a 3' subdomain of the third hairpin molecule and a 5' subdomain of the third hairpin molecule, wherein the third paired stem domain comprises a third coupling segment, a third payload segment, and complements thereof, and (iii) a third hairpin loop domain; and (g) extending the second coupling segment of the second extended oligonucleotide hybridized to the third 3' toehold domain through the third paired stem domain of the third hairpin molecule, thereby displacing the 5' subdomain of the third hairpin molecule and forming a third extended oligonucleotide comprising the second coupling segment, the third payload segment and the third coupling segment.

The method can comprise repeating the following steps n times: contacting the particle with a (n+1)th hairpin molecule, wherein the (n+1)th hairpin molecule comprises: (i) an unpaired (n+1)th 3' toehold domain complementary to the nth coupling segment, (ii) a (n+1)th paired stem domain formed by intramolecular nucleotide base pairing between a 3' subdomain of the (n+1)th hairpin molecule and a 5' subdomain of the (n+1)th hairpin molecule, wherein the (n+1)th paired stem domain comprises a (n+1)th coupling segment, a (n+1)th payload segment, and complements thereof, and (iii) a (n+1)th hairpin loop domain; and extending the nth coupling segment of the nth extended oligonucleotide hybridized to the (n+1)th 3' toehold domain through the (n+1)th paired stem domain of the (n+1)th hairpin molecule, thereby displacing the 5' subdomain of the (n+1)th hairpin molecule and forming a (n+1)th extended oligonucleotide comprising the nth coupling segment, the (n+1)th payload segment and the (n+1)th coupling segment. In some embodiments, n is an integer between about 1 and about 8. The method can further comprising a capping reaction, comprising: contacting a capping oligonucleotide with the (n+1)th extended oligonucleotide, wherein the capping oligonucleotide is a single-stranded molecule comprising a 3' region capable of annealing to the 3' end of the first extended oligonucleotide, the second extended oligonucleotide, or the third extended oligonucleotide; and extending the (n+1)th extended oligonucleotide hybridized with the capping oligonucleotide, thereby generating a capped oligonucleotide.

The first payload segment can comprise a first barcode segment. The second payload segment can comprise a second barcode segment. The third payload segment can comprise a third barcode segment. The first barcode segment can be selected from a first set of barcode segments. The second barcode segment can be selected from a second set of barcode segments. The third barcode segment can be selected from a third set of barcode segments. The first payload segment, second payload segment, and/or third payload segment can comprise a unique molecular identifier (UMI), a primer sequence, a primer annealing sequence, an attachment sequence, a sequencing primer sequence, or any combination thereof. The second extended oligonucleotide can comprise the input primer, the first payload segment, the first coupling segment, the second payload segment, and the second coupling segment. The third extended oligonucleotide can comprise the input primer, the first payload segment, the first coupling segment, the second payload segment, the second coupling segment, the third payload segment, and the third coupling segment. In some embodiments, one or more of steps (b), (c), (d), (e), (f) and (g) are performed under condition(s) that result in annealing, nucleic acid polymerization, and strand displacement. In some embodiments, the first coupling segment, second coupling segment, and third coupling segment can be different. In some embodiments, the particle is not washed between steps. The contacting steps and extending steps can be performed at about 37° C. The first hairpin molecule and/or second hairpin molecule can comprise a 3' poly(dT) region. The first hairpin molecule and/or second hairpin molecule can comprise an inverted-dT at its 3' end. The first hairpin molecule and/or second hairpin molecule can comprise a dideoxy(T) (ddT), a nucleoside not capable of being 3' extended by a DNA polymerase, or any combination thereof.

In some embodiments, the method can comprise a capping reaction. In some embodiments, the capping reaction comprises: contacting a capping oligonucleotide with the first extended oligonucleotide, the second extended oligonucleotide, and/or the third extended oligonucleotide, wherein the capping oligonucleotide is a single-stranded molecule comprising a 3' region capable of annealing to the 3' end of the first extended oligonucleotide, the second extended oligonucleotide, or the third extended oligonucleotide; and extending the first extended oligonucleotide, the second extended oligonucleotide, and/or the third extended oligonucleotide hybridized with the capping oligonucleotide, thereby generating a capped oligonucleotide. The method can comprise contacting the particle with a single strand-specific exonuclease. The capping oligonucleotide can comprise one or more of a unique molecular identifier (UMI), a primer sequence, a primer annealing sequence, an attachment sequence, a sequencing primer sequence, or any combination thereof. The capped oligonucleotide can be single-stranded or double-stranded. The method can comprise contacting the population of capped beads with a single strand-specific exonuclease (e.g., Exonuclease I). The beads can comprise magnetic beads, glass beads, cellulose beads, epichlorohydrin-cross-linked-dextran beads, polyacrylamide beads, agarose beads, polystyrene beads, gel-based beads, or any combination thereof. The beads can comprise hydrogel beads. The second pooled bead population, the third pooled bead population, and/or the fourth pooled bead population can comprise at least 1,000 beads. In some embodiments, each bead comprises at least 1,000 oligonucleotides.

In some embodiments, the percentage of the first extended oligonucleotides, the second extended oligonucleotides, and/or the third extended oligonucleotides comprising a first payload segment can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the first extended oligonucleotides, the second extended oligonucleotides, and/or the third extended oligonucleotides comprising a first payload segment can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some embodiments, more than 80% of the first extended oligonucleotides, the second extended oligonucleotides, and/or the third extended oligonucleotides comprise a first payload segment. In some embodiments, more than 95% of the first extended oligonucleotides, the second extended oligonucleotides, and/or the third extended oligonucleotides comprise a first payload segment. In some embodiments, more than 99% of the first extended oligonucleotides the second extended oligonucleotides, and/or the third extended oligonucleotides comprise a first payload segment.

In some embodiments, the extension of particle-associated oligonucleotides as provided herein requires at least 1, 2, 3, 4, 5, 6, 7, 8, 9, 10, 11, 12, 13, 14, 15, 16, 17, 18, 19, or 20 fold less input nucleic acid as compared to a ligation-based method of extending particle-associated oligonucleotides. In some embodiments, the extension of particle-associated oligonucleotides requires at least ten-fold less input nucleic acid as compared to a ligation-based method of extending particle-associated oligonucleotides. In some embodiments, the extension of particle-associated oligonucleotides requires at least hundred-fold less input nucleic acid as compared to a ligation-based method of extending particle-associated oligonucleotides.

In some embodiments, the extension of particle-associated oligonucleotides as provided herein requires at least 1, 2, 3, 4, 5, 6, 7, 8, 9, 10, 11, 12, 13, 14, 15, 16, 17, 18, 19, or 20 fold less input nucleic acid as compared to a non-PER extension-based method of extending particle-associated oligonucleotides. In some embodiments, the extension of particle-associated oligonucleotides requires at least ten-fold less input nucleic acid as compared to a non-PER extension-based method of extending particle-associated oligonucleotides. In some embodiments, the extension of particle-associated oligonucleotides requires at least hundred-fold less input nucleic acid as compared to a non-PER extension-based method of extending particle-associated oligonucleotides.

The coupling segment can have different lengths in different implementations. A coupling segment can comprise about 1 nucleotide to about 50 nucleotides. In some embodiments, a coupling segment comprises about 9 nucleotides. In some embodiments, a coupling segment is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, an coupling segment is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

The payload segment (e.g., barcode segment) can have different lengths in different implementations. In some embodiments, a payload segment (e.g., a barcode segment) can comprise about 1 nucleotide to about 50 nucleotides. In some embodiments, a barcode segment can comprise about 5 nucleotides. In some embodiments, a payload segment (e.g., barcode segment) is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, a payload segment (e.g., barcode segment) is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

FIGS. 3A-3B depict non-limiting exemplary nucleic acids employed in the methods provided herein. FIG. 3A depicts an exemplary structure of a hairpin molecule provided herein. The hairpin molecule 302 can comprise barcode segment 306 excluding G ("HHHHH"), a complement of the barcode segment 308 excluding C ("DDDDD"), an unpaired 3' toehold domain 304 complementary to an input primer or another coupling segment (e.g., "AGATCGGAA"), a coupling segment 310 ("YYYYYYYYY") and a coupling segment complement 312 ("XXXXXXXXX"). The hairpin molecule 302 can comprise a linkage domain (e.g., a hairpin loop domain 314; "TTTT"), a polymerase stopper 316, and a 3' poly(dT) region 318. FIG. 3B depicts an exemplary acrydite-modified input primer (SEQ ID NO: 45), an exemplary first hairpin molecule (SEQ ID NO: 1), an exemplary second hairpin molecule (SEQ ID NO: 11), an exemplary third hairpin molecule (SEQ ID NO: 21), an exemplary fourth hairpin molecule (SEQ ID NO: 31), and an exemplary capping oligonucleotide (SEQ ID NO: 46) which are predicted to produce barcoded bead oligonucleotide (SEQ ID NO: 47) when employed in the methods provided herein. The acrydite-modified input primer can comprise a poly T spacer with the acrydite modification. The capping oligonucleotide can comprise a 10 bp UMI (Unique Molecular Identifier, a sequence of random bases, "NNNNNNNNNN") or other arbitrary sequences.

In some embodiments, a "domain" refers to a discrete, contiguous sequence of nucleotides or nucleotide base pairs, depending on whether the domain is unpaired (single-stranded nucleotides) or paired (double-stranded nucleotide base pairs), respectively. In some embodiments, a domain is described as having multiple subdomains for the purpose of defining intramolecular (within the same molecular species) and intermolecular (between two separate molecular species) complementarity. One domain (or one subdomain) is "complementary to" another domain if one domain contains nucleotides that base pair (hybridize/bind through Watson-Crick nucleotide base pairing) with nucleotides of the other domain such that the two domains form a paired (double-stranded) or partially-paired molecular species/structure. Complementary domains need not be perfectly (100%) complementary to form a paired structure, although perfect complementarity is provided, in some embodiments. Thus, a sequence that is "complementary" to a particular domain binds to that domain, for example, for a time sufficient to initiate polymerization in the presence of polymerase.

It is contemplated that any one of the catalytic PER molecules (e.g., hairpin molecules) provided herein may comprise a "linkage domain" located at the end of the molecule opposite to the toehold domain. The linkage domain may be a hairpin loop (loop domain) or the linkage domain may include complementary nucleotides covalently crosslinked to each other (e.g., at least 1, 2, 3, 4, 5, 6, 7, 8, 9, or 10 covalently crosslinked nucleotide base pairs). In some embodiments, a linkage domain is simply a stable paired domain, for example, having a length of at least 10 nucleotides (e.g., such that the domain remains paired throughout the reactions disclosed herein).

The length of a catalytic PER molecule (e.g., hairpin molecule) may vary. In some embodiments, a catalytic PER molecule has a length of 25-300 nucleotides. For example, a catalytic PER molecule may have a length of 25-250, 25-200, 25-150, 25-100, 25-50, 50-300, 50-250, 50-200, 50-150 or 50-100 nucleotides. In some embodiments, a catalytic PER molecule has a length of 30-50, 40-60, 50-70, 60-80, 70-90, 80-100, 100-125, 100-150 or 100-200 nucleotides. In some embodiments, a catalytic PER molecule has a length of 35, 36, 37, 38, 39, 40, 41, 42, 43, 44, 45, 46, 47, 48, 49. 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A catalytic PER molecule, in some embodiments, is longer than 300 nucleotides, or shorter than 25 nucleotides.

A "toehold domain" refers to an unpaired sequence of nucleotides located at the 3' end of the catalytic PER molecule (e.g., hairpin molecule) and is complementary to (and binds to) a nucleotide sequence of an input primer or another coupling segment. The length of a toehold domain may vary. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

A "stem domain" (e.g., "paired domain") of a catalytic PER molecule refers to a paired sequence of nucleotides (e.g., Watson-Crick nucleobase pairing) located 5' from (and, in some embodiments, directly adjacent to) the unpaired toehold domain of a catalytic PER molecule (e.g., hairpin molecule). The paired domain of a catalytic PER molecule can be formed by nucleotide base pairing between a displacement strand and a template strand containing a toehold domain. The paired stem domain of a catalytic hairpin molecule can be formed by intramolecular base pairing (base pairing between nucleotides within the same molecule) of two subdomains of a catalytic hairpin molecule: e.g., an internal/central subdomain located 5' from the toehold domain bound (hybridized) to a subdomain located at the 5' end of the catalytic hairpin. The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

While a paired domain is generally formed by intramolecular base pairing of two subdomains of a catalytic PER molecule, it is contemplated that this paired domain may contain at least one mismatch pair (e.g., pairing of A with C or G, or pairing of T with C or G). In some embodiments, the stem domain has 1-5 mismatch nucleotide base pairs. For example, a paired domain may be have 1, 2, 3, 4 or 5 mismatch nucleotide base pairs.

In some embodiments, extension of an input primer or coupling segment (bound to a toehold domain) by a displacing polymerase is terminated by the presence of a molecule or modification in the catalytic PER molecule that terminates polymerization. Thus, in some embodiments, catalytic PER molecules of the present disclosure comprise a molecule or modification that terminates polymerization. A molecule or modification that terminates polymerization ("polymerase stopper") is typically located in a paired domain (e.g., stem domain) of a catalytic PER molecule such that polymerization terminates extension of the primer through the paired domain. For catalytic PER molecules arranged in the form of a hairpin, a molecule or modification that terminates polymerization may be located between the paired stem domain and the loop domain. In some embodiments, the molecule that terminate polymerization (e.g., polymerase stopper) is a synthetic non-DNA linker, for example, a triethylene glycol spacer, such as the Int Spacer 9 (iSp9) or Spacer 18 (Integrated DNA Technologies (IDT)). It is contemplated that any non-native linker that terminates polymerization by a polymerase may be used as provided herein. Other non-limiting examples of such molecules and modifications include a three-carbon linkage (/iSpC3/) (IDT), ACRYDITE (IDT), adenylation, azide, digoxigenin (NHS ester), cholesteryl-TEG (IDT), I-LINKER (IDT), and 3-cyanovinylcarbazole (CNVK) and variants thereof. Typically, but not always, short linkers (e.g., iSp9) lead to faster reaction times.

In some embodiments, the molecule that terminates polymerization ("polymerase stopper") is a single or paired non-natural nucleotide sequence, such as iso-dG and iso-dC (IDT), which are chemical variants of cytosine and guanine, respectively. Iso-dC will base pair (hydrogen bond) with Iso-dG but not with dG Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position. In some embodiments, the polymerase stopper comprises an abasic site, a stable abasic site (e.g., 1',2'-dideoxy), a chemically trapped abasic site, or any combination thereof. The abasic site can comprise an apurinic site, an apyrimidinic site, or both. The abasic site can be generated by an alkylating agent or an oxidizing agent. The chemically trapped abasic site can comprise an abasic site reacted with alkoxyamine or sodium borohydride.

In some embodiments, the efficiency of performance of a "polymerase stopper" modification is improved by lowering dNTP concentrations (e.g., from 200 µM) in a reaction to 100 µM, 10 µM, 1 µM, or less.

Inclusion of a molecule or modification that terminates polymerization ("polymerase stopper") can create a "bulge" in a double-stranded domain of catalytic PER molecule (e.g., a stem domain for hairpin structures), because the molecule or modification is not paired. Thus, in some embodiments, catalytic PER molecules are designed to include, opposite the molecule or modification, a single nucleotide (e.g., thymine), at least two of same nucleotide (e.g., a thymine dimer (TT) or trimer (TTT)), or a non-natural modification). In some embodiments, PER-catalyzed oligonucleotide extension by a polymerase along a template (e.g., 3' subdomain of a hairpin molecule) continues until the polymerase hits the "polymerase stopper" points (a molecule that terminates polymerization). DNA base monomers (dNTPs) are supplied in the system for the polymerase to add to the newly synthesized part. The stopping points can be encoded by one of the following two ways, for example. A non-nucleotide chemical spacer (e.g., triethylene glycol spacer) may be added as a stopper, or a subset of bases may be used in a system and the excluded base used as the stopper. Other molecules that terminate polymerization are described elsewhere herein. For example, if a three-letter code with A, T, and C in the template is used, their complement base monomers, A, T, and G, are supplied in the system, and G's are embedded at the end of the template. The polymerase cannot extend the new strand because the system does not have the complement base monomer, C. When the polymerase finishes the synthesis of the new domain and reaches the stopper point, it leaves (dissociates from) the template. Then, since the newly synthesized domain shares the same sequence as the template, it can undergo a random walk branch migration process. If the original template displaces the newly synthesized domain, a new primer for the next reaction is exposed. The polymerase stopper can comprise a cytosine 5' of the toehold domain, each coupling segment and each payload segment (e.g., barcode segment) can be comprised of adenine, thymine and cytosine, and the deoxyribonucleotide triphosphates (dNTPs) employed in the PER-catalyzed oligonucleotide extension can comprise adenine, thymine and cytosine. The polymerase stopper can comprise a guanine 5' of the toehold domain, each coupling segment and each payload segment (e.g., barcode segment) can be comprised of adenine, thymine and guanine, and the deoxyribonucleotide triphosphates (dNTPs) employed in the PER-catalyzed oligonucleotide extension can comprise adenine, thymine and guanine.

A "loop domain" of a catalytic hairpin refers to a primarily unpaired sequence of nucleotides that form a loop-like structure at the end (adjacent to) of the stem domain. The length of a loop domain may vary. In some embodiments, a loop domain has a length 3-200 nucleotides. For example, a loop domain may have a length of 3-175, 3-150, 3-125, 3-100, 3-75, 3-50, 3-25, 4-175, 4-150, 4-125, 4-100, 4-75, 4-50, 4-25, 5-175, 5-150, 5-125, 5-100, 5-75, 5-50 or 5-25 nucleotides. In some embodiments, a loop domain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a loop domain has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49 or 50 nucleotides. A loop domain, in some embodiments, is longer than 300 nucleotides.

In some embodiments, a catalytic PER molecule does not contain a hairpin loop domain. Catalytic PER molecules that do not have a hairpin loop (are not formed by a contiguous stretch of nucleotides) are described, in some embodiments, as being a duplex that includes "displacement strand" paired with (hybridized/bound to) a "template strand." For example, a catalytic PER molecule may simply be a duplex comprising a 3' unpaired toehold domain adjacent to a paired domain, similar to a stem domain (without the adjacent loop domain). Catalytic PER molecules that do not include a loop domain may be stabilized at the end opposite the 3' toehold domain through crosslinking or nucleotide base complementarity between a stretch (e.g., 10 or more) nucleotide base pairs. Such duplex molecules can operate in a manner similar to their hairpin counterparts.

In some embodiments, the nucleotide sequence that binds to the toehold domain of a catalytic PER molecule (e.g., an input primer or a coupling segment) has a length of 10-50 nucleotides. For example, an input primer or a coupling segment may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, an input primer or a coupling segment has a length of 10, 15, 20, 25, 30, 35, 40, 45 or 50 nucleotides. In some embodiments, an input primer or a coupling segment has a length of 15, 16, 17, 18, 19, 20, 21, 22, 23, 24 or 25 nucleotides. An input primer or a coupling segment, in some embodiments, is longer than 50 nucleotides, or shorter than 10 nucleotides. It should be understood that the full length of a an input primer or a coupling segment depends, at least in part, on the number and length of appended (polymerized) sequences, which can depend on the number and length of catalytic PER molecules present in a reaction.

PER-catalyzed oligonucleotide extensions can require the use of a polymerase. In some embodiments, the polymerase is a DNA polymerase (DNAP), such as a DNA polymerase having DNA strand displacement activity (a strand displacement polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: IX reaction buffer (e.g., 50 mM Tris-HCl, 10 mM MgCl2, 10 mM (NH4)2S04, 4 mM DTT) supplement with purified bovine serum albumin (BSA), pH 7.5, incubated at 30° C. In some embodiments, the polymerase is Bst DNA polymerase, large fragment. In such embodiments, the reaction conditions may be as follows: IX reaction buffer (e.g., 20 mM Tris-HCl, 10 mM (NH4)2S04, 10 mM KCl, 2 mM MgS04, 0.1% TRITON® X-100), pH 8.8, incubated at 65° C. In some embodiments, the polymerase is Bsu DNA polymerase. In such embodiments, the reaction conditions may be as follows: IX reaction buffer {e.g. 50 mM NaCl, 10 mM Tris-HCl, 10 mM MgCl2, 1 mM DTT), pH 7.9, incubated at 37° C.

The concentration of primer, catalytic PER molecules and dNTPs in methods provided herein may be varied depending, for example, on the particular application and kinetics required for that particular application.

The concentration of the input primer (e.g., particle associated oligonucleotide) in a PER-catalyzed oligonucleotide extension may be, for example, 10 nM to 1000 nM. In some embodiments, the input primer concentration in a PER-catalyzed oligonucleotide extension is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the input primer concentration in PER-catalyzed oligonucleotide extension is 100-200, 100-300, 100-400, 100-500, 100-600, 100-70, 100-800, 100-900 or 100-1000 nM. In some embodiments, the input primer concentration in a PER-catalyzed oligonucleotide extension is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the input primer concentration in a PER-catalyzed oligonucleotide extension is 100, 200, 300, 400, 500, 600, 700, 800, 900 or 1000 nM. The concentration of input primer in a PER-catalyzed oligonucleotide extension may be less than 10 nM or greater than 1000 nM.

The concentration of catalytic PER molecules (e.g., hairpin molecules) in a PER-catalyzed oligonucleotide extension provided herein may be, for example, 5 nM to 1000 nM. In some embodiments, the catalytic PER molecule concentration in a PER-catalyzed oligonucleotide extension is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the catalytic PER molecule concentration in a PER-catalyzed oligonucleotide extension is 10-200, 10-300, 10-400, 10-500, 10-600, 10-70, 10-800, 10-900 or 10-100 nM. In some embodiments, the catalytic PER molecule concentration in a PER-catalyzed oligonucleotide extension is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the catalytic PER molecule concentration in a PER-catalyzed oligonucleotide extension is 10, 20, 30, 40, 50, 60, 70, 80, 90 or 100 nM. The concentration of catalytic PER molecule in a PER-catalyzed oligonucleotide extension may be less than 5 nM or greater than 1000 nM.

The ratio of input primer (e.g., particle associated oligonucleotide) to catalytic PER molecule in PER-catalyzed oligonucleotide extension may be 2:1 to 100:1. In some embodiments, the ratio of input primer to catalytic PER molecule is 2:1, 3:1, 4:1, 5:1, 6:1, :1, 8:1, 9:1, 10:1, 11:1, 12:1, 13:1, 14:1, 15:1, 16:1, 17:1, 18:1, 19:1 or 20:1. In some embodiments, the ratio of input primer to catalytic PER molecule is 30:1, 40:1, 50:1, 60:1, 70:1, 80:1 or 90:1.

The number of different catalytic PER molecules in a PER-catalyzed oligonucleotide extension is non-limiting. In some embodiments the PER-catalyzed oligonucleotide extension is multiplexed. A multiplexed PER-catalyzed oligonucleotide extension may comprise $1-10^{10}$ different catalytic PER molecules (each with a specific toehold domain and/or coupling segment sequence, for example). In some embodiments, a multiplexed PER-catalyzed oligonucleotide extension comprises 1-10, $1-10^2$, $1-10^3$, $1-10^4$, $1-10^5$, $1-10^6$, $1-10^7$, $1-10^8$, $1-10^9$, $1-10^{10}$, or more, different catalytic PER molecules. In some embodiments, a multiplexed PER-catalyzed oligonucleotide extension comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different catalytic PER molecules. In some embodiments, a multiplexed PER-catalyzed oligonucleotide extension comprises 1, 2, 3, 4, 5, 6, 7, 8, 9, 10, 11, 12, 13, 14, 15, 16, 17, 28, 19, 20, 21, 22, 23, 24 or 25 different catalytic PER molecules. Catalytic PER molecules are different from each other if their toehold domains and/or coupling segments differ from each other, for example.

The kinetics of a PER-catalyzed oligonucleotide extension may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a PER-catalyzed oligonucleotide extension is performed may vary from, for example, 4° C. to 65° C. (e.g., 4° C., 25° C., 37° C., 42° C. or 65° C.). In some embodiments, the temperature at which a PER-catalyzed oligonucleotide extension is performed is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a PER-catalyzed oligonucleotide extension is performed at room temperature, while in other embodiments, a PER-catalyzed oligonucleotide extension is performed at 37° C.

A PER-catalyzed oligonucleotide extension may be performed (incubated) for 30 minutes (min) to 24 hours (hr). In some embodiments, a PER-catalyzed oligonucleotide extension is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr, or 24 hr.

The kinetics of a PER-catalyzed oligonucleotide extension, in some embodiments, depends heavily on the concentration of dNTPs in a reaction. The concentration of dNTPs in a PER-catalyzed oligonucleotide extension may be, for example, 2-1000 µM. In some embodiments, the dNTP concentration in a PER-catalyzed oligonucleotide extension is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2- 140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a PER-catalyzed oligonucleotide extension may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a PER-catalyzed oligonucleotide extension is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, PER systems may use hot start/clean amp dNTPs, phosphorothioate dNTPs, or fluorescent dNTPs. Other dNTP variants may be used. Because some modified dNTPs are less favorable than normal (unmodified) DNA-DNA binding, the hairpin back displacement process may be increased with their usage. Similarly, a hairpin comprised of a different type of nucleic acid (e.g., LNA, RNA or interspersed modified bases such as methyl dC or super T IDT modifications) may be used in some embodiments to increase the speed of a PER by forming stronger bonds than the synthesized primer with respect to the catalytic PER molecule.

In some embodiments, the catalytic PER molecules provided herein (e.g., hairpin molecules) comprises a backbone other than a phosphodiester backbone. For example, a hairpin molecule, in some embodiments, may comprise phosphoramide, phosphorothioate, phosphorodithioate, O-methylphophoroamidite linkages, peptide nucleic acids or a combination of any two or more of the foregoing linkages. A catalytic PER molecule may be single-stranded (ss) or double-stranded (ds), as specified, or a catalytic PER molecule may contain portions of both single-stranded and double-stranded sequence. In some embodiments, a catalytic PER molecule contains portions of triple-stranded sequence, or other non-Watson-Crick base pairing such as G-quartets, G-quadruplexes, and i-motifs. An catalytic PER molecule may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocyto sine and isoguanine.

Methods of Preparing a Library of Barcoded Beads

Figure 2A:
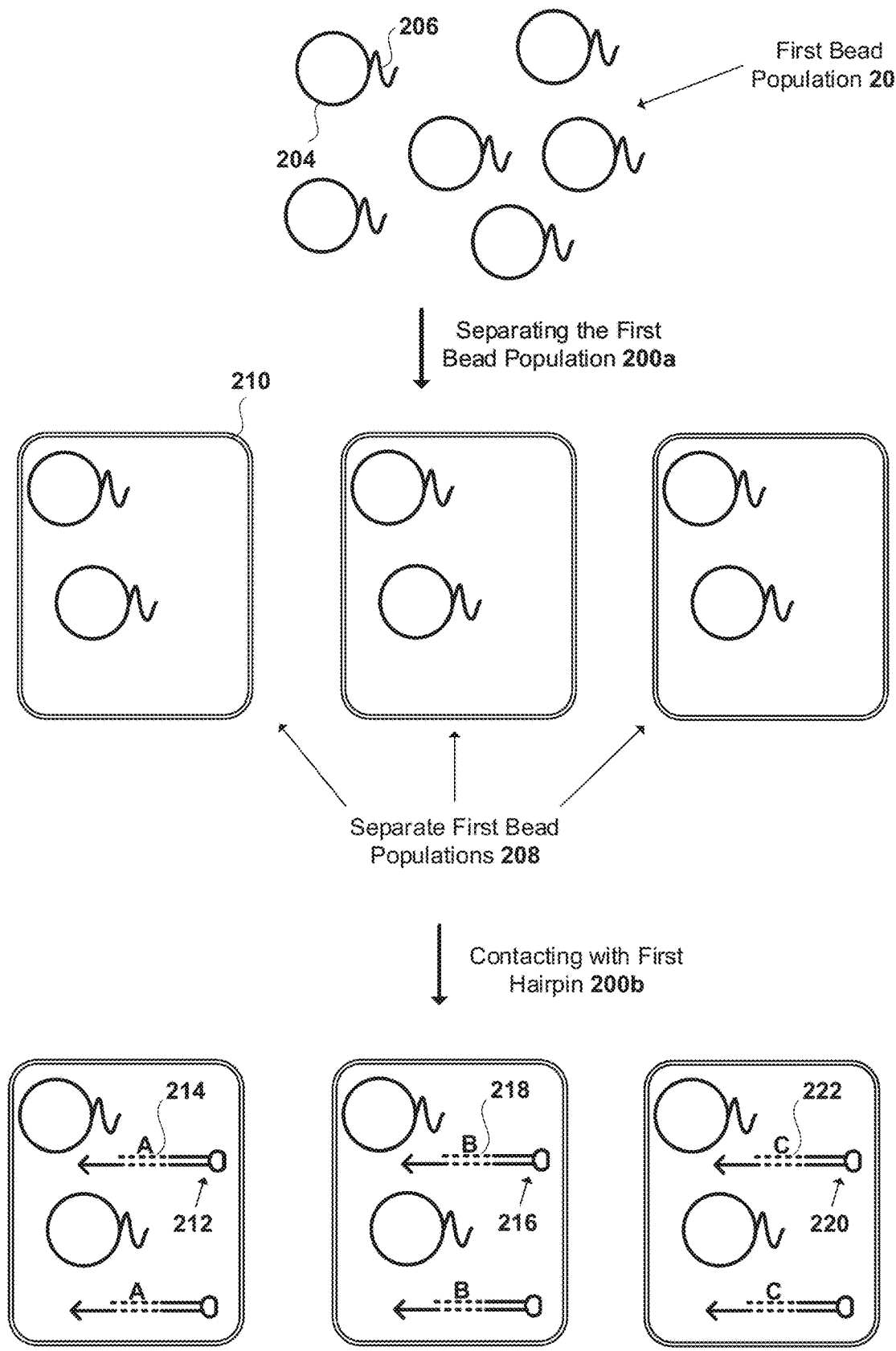
FIGS. 2A-2C are schematic illustrations of a non-limiting exemplary workflow for preparing a library of barcoded particles.
Figure 2B:
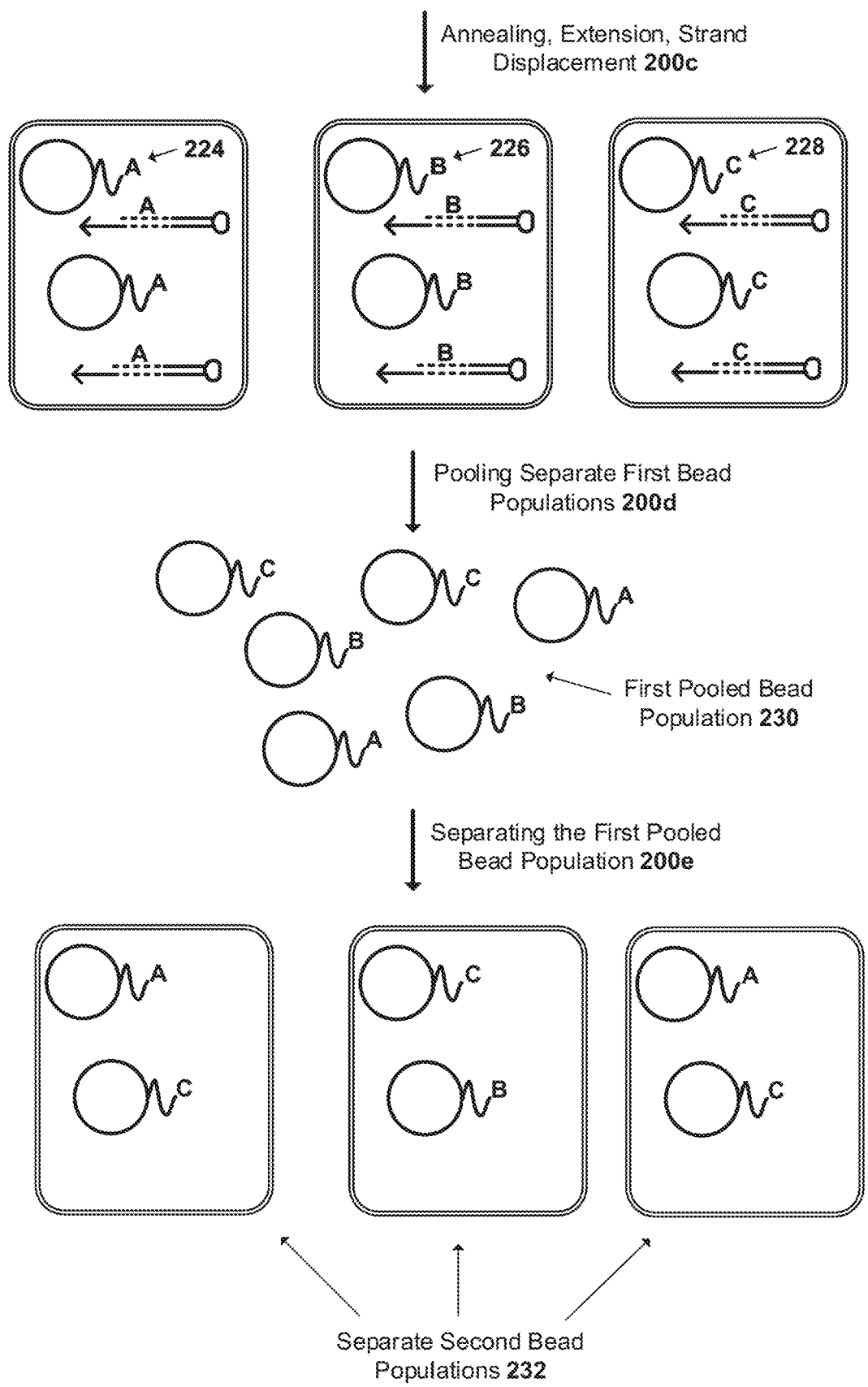
Figure 2C:
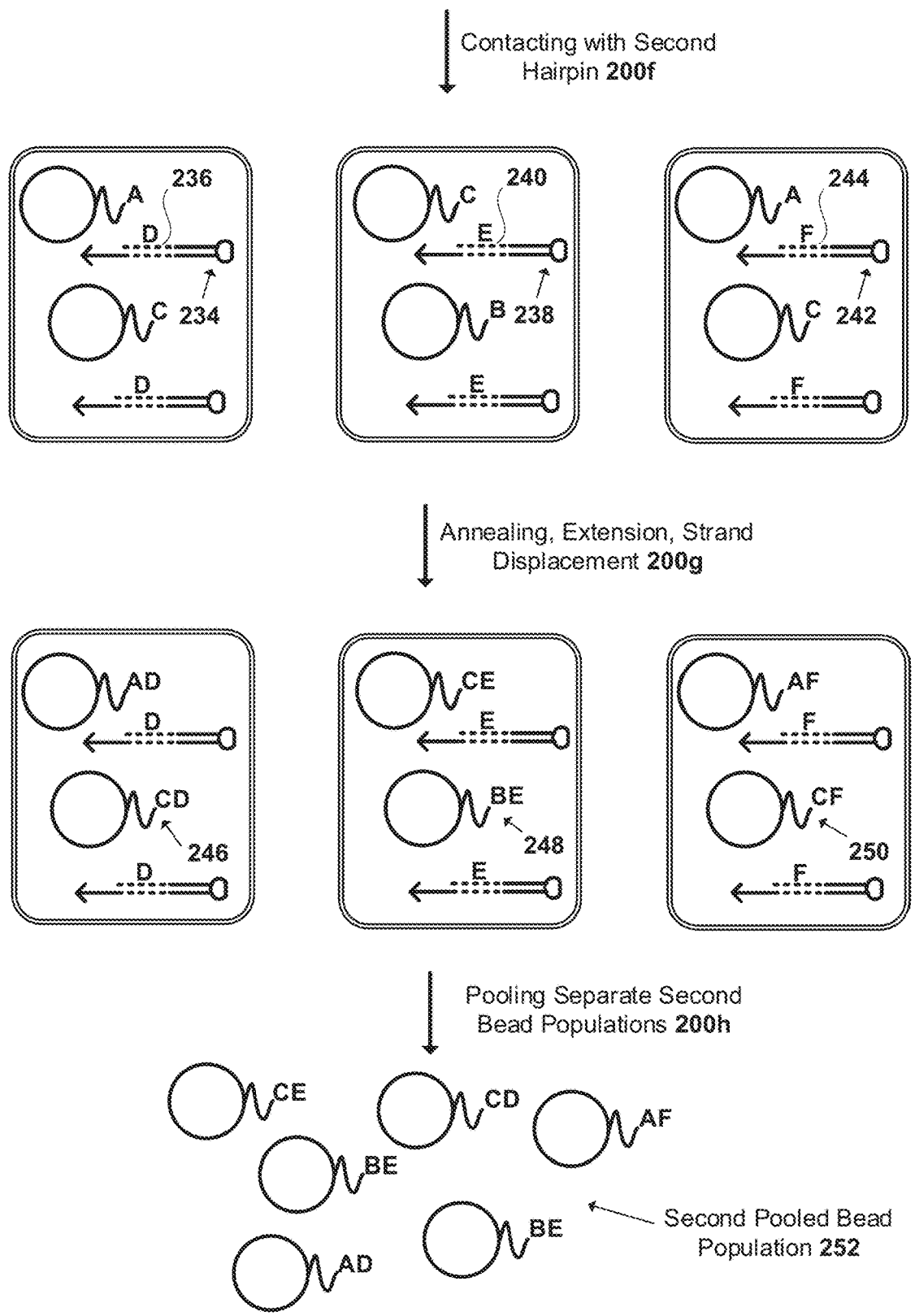

There are provided, in some embodiments, methods and compositions for producing a library of barcoded particles (e.g., beads). FIGS. 2A-2C are schematic illustrations of a non-limiting exemplary workflow for preparing a library of barcoded particles (e.g., beads). The workflow can comprise providing a first bead population 202. First bead population 202 can comprise a plurality of first beads 204 each comprising plurality of oligonucleotides 206. Oligonucleotides 206 can each comprise an input primer. The workflow can comprise separating first bead population 202 (step 200a) to generate a plurality of separate first bead populations 208. Separating first bead population 202 into a plurality of separate first bead populations 208 can comprise partitioning first bead population 202 to a plurality of partitions 210 (e.g., wells, microwells, tubes, vials, microcapsules, droplets, or any combination thereof). The workflow can comprise contacting each separate first bead populations 208 with a different first hairpin molecule (step 200b). For example, three separate first bead populations 208 can be exposed to either first hairpin molecule 212 (comprising a first barcode segment 214, "A"), first hairpin molecule 216 (comprising a first barcode segment 218, "B"), or first hairpin molecule 220 (comprising a first barcode segment 222, "C"). The input primer of oligonucleotides 206 can be complementary to the unpaired 3' toehold domain of the first hairpin molecules 212, 218, and 220. First hairpin molecules 212, 216, and 220 can comprise an identical first coupling segment. In some embodiments, one or more steps of the workflow (e.g., contacting and extending steps) are performed under condition(s) that result in annealing, nucleic acid polymerization, and strand displacement. In some embodiments, one or more steps of the workflow (e.g., contacting and extending steps) are performed in the presence of a polymerase having strand displacement activity (e.g., phi29 DNA polymerase, Bst DNA polymerase, Bsu DNA polymerase, large fragment, or any combination thereof) and deoxyribonucleotide triphosphates (dNTPs). The workflow can comprise PER-catalyzed extension of oligonucleotides 206 (annealing, extension, and strand displacement; step 200c) generating a first extended oligonucleotide 224 comprising first barcode segment 214 ("A"), a first extended oligonucleotide 226 comprising first barcode segment 218 ("B"), and a first extended oligonucleotide 228 comprising first barcode segment 222 ("C"). The workflow can comprise pooling the separate first bead populations 208 to generate a first pooled bead population 230 (step 200d). The workflow can comprise separating first pooled bead population 230 (step 200e) to generate a plurality of separate second bead populations 232.

The workflow can comprise contacting each separate second bead population 232 with a different second hairpin molecule (step 200f). For example, three separate second bead populations 232 can be exposed to either second hairpin molecule 234 (comprising a second barcode segment 236, "D"), second hairpin molecule 238 (comprising a second barcode segment 240, "E"), or second hairpin molecule 242 (comprising a second barcode segment 244, "F"). The first coupling segment of first hairpin molecules 212, 216, and 220 can be complementary to the unpaired 3' toehold domain of the second hairpin molecules 234, 238, and 242. Second hairpin molecules 234, 238, and 242 can comprise an identical second coupling segment. The workflow can comprise PER-catalyzed extension of the first extended oligonucleotides (annealing, extension, and strand displacement; step 200g) generating a second extended oligonucleotide 246 comprising second barcode segment 236 ("D"), a second extended oligonucleotide 248 comprising second barcode segment 240 ("E"), and a second extended oligonucleotide 250 comprising second barcode segment 244 ("F"). The workflow can comprise pooling the separate second bead populations 232 to generate a second pooled bead population 252 (step 200h). The second pooled bead population 252 can comprise a library of barcoded beads.

In some embodiments the workflow is performed isothermally. In some embodiments, the workflow does not comprise washing steps. The second pooled bead population 252 can undergo additional rounds of separating, PER-catalyzed extensions (e.g., employing a third hairpin molecule comprising an unpaired 3' toehold domain complementary to the second coupling segment), and pooling. In some embodiments, on each step, the sample is split amongst each of the k labeling reactions. It is then recombined, mixed and split again into k labeling reactions. After n extension rounds, the resulting sample can have up to 10 barcodes. By using 72 unique barcodes over 4 rounds, 26.8 million unique sequences can be obtained.

The workflow can further comprise the second pooled bead population 252 undergoing a capping reaction with a capping oligonucleotide as described herein, thereby incorporating the sequence of the capping oligonucleotide into the bead-associated oligonucleotide. The workflow can further comprise treatment of the second pooled bead population 252 with a single-strand specific exonuclease (e.g., exonuclease I). The workflow can further comprise a step denaturing the bead-associated oligonucleotides, generating a single-stranded bead-associated oligonucleotide. If the beads are split up There are provided, in some embodiments, methods of preparing a library of barcoded beads. In some embodiments, the method comprises: (a) providing a plurality of separate first bead populations, wherein each bead comprises a plurality of oligonucleotides each comprising an input primer; (b) contacting each separate first bead population with a first hairpin molecule, wherein the first hairpin molecule comprises: (i) an unpaired first 3' toehold domain complementary to the input primer, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; (c) extending the input primer hybridized to the first 3' toehold domain through the first paired stem domain of the first hairpin molecule, thereby displacing the 5' subdomain of the first hairpin molecule and forming a first extended oligonucleotide, wherein the first extended oligonucleotide of each separate first bead population comprises a different first barcode segment; (d) pooling the separate first bead populations to generate a first pooled bead population; (e) separating the first pooled bead population into a plurality of separate second bead populations; (f) contacting each separate second bead population with a second hairpin molecule, wherein the second hairpin molecule comprises: (i) an unpaired second 3' toehold domain complementary to the first coupling segment, (ii) a second paired stem domain formed by intramolecular nucleotide base pairing between a 3' subdomain of the second hairpin molecule and a 5' subdomain of the second hairpin molecule, wherein the second paired stem domain comprises a second coupling segment, a second barcode segment, and complements thereof, and (iii) a second hairpin loop domain; (g) extending the first coupling segment of the first extended oligonucleotide hybridized to the second 3' toehold domain through the second paired stem domain of the second hairpin molecule, thereby displacing the 5' subdomain of the second hairpin molecule and forming a second extended oligonucleotide, wherein the second extended oligonucleotide of each separate second bead population comprises a different second barcode segment; and (h) pooling the separate second bead populations to generate a second pooled bead population comprising a library of barcoded beads. The method can comprise: (i) separating the second pooled bead population into a plurality of separate third bead populations; (j) contacting each separate third bead population with a third hairpin molecule, wherein the third hairpin molecule comprises: (i) an unpaired third 3' toehold domain complementary to the second coupling segment, (ii) a third paired stem domain formed by intramolecular nucleotide base pairing between a 3' subdomain of the third hairpin molecule and a 5' subdomain of the third hairpin molecule, wherein the third paired stem domain comprises a third coupling segment, a third barcode segment, and complements thereof, and (iii) a third hairpin loop domain; (k) extending the second coupling segment of the second extended oligonucleotide hybridized to the third 3' toehold domain through the third paired stem domain of the third hairpin molecule, thereby displacing the 5' subdomain of the third hairpin molecule and forming a third extended oligonucleotide, wherein the third extended oligonucleotide of each separate third bead population comprises a different third barcode segment; and (l) pooling the separate third bead populations to generate a third pooled bead population. The method can comprise: (m) separating the third pooled bead population into a plurality of separate fourth bead populations; (n) contacting each separate fourth bead population with a fourth hairpin molecule, wherein the fourth hairpin molecule comprises: (i) an unpaired fourth 3' toehold domain complementary to the third coupling segment, (ii) a fourth paired stem domain formed by intramolecular nucleotide base pairing between a 3' subdomain of the fourth hairpin molecule and a 5' subdomain of the fourth hairpin molecule, wherein the fourth paired stem domain comprises a fourth coupling segment, a fourth barcode segment, and complements thereof, and (iii) a fourth hairpin loop domain; (o) extending the third coupling segment of the third extended oligonucleotide hybridized to the fourth 3' toehold domain through the fourth paired stem domain of the fourth hairpin molecule, thereby displacing the 5' subdomain of the fourth hairpin molecule and forming a fourth extended oligonucleotide, wherein the fourth extended oligonucleotide of each separate fourth bead population comprises a different fourth barcode segment; and (p) pooling the separate fourth bead populations to generate a fourth pooled bead population comprising a library of barcoded beads.

The method can further comprise repeating the following steps n times: separating the (n+1)th pooled bead population into a plurality of separate (n+2)th bead populations; contacting each separate (n+2)th bead population with a (n+2)th hairpin molecule, wherein the (n+2)th hairpin molecule comprises: (i) an unpaired (n+2)th 3' toehold domain complementary to the (n+1)th coupling segment, (ii) a (n+2)th paired stem domain formed by intramolecular nucleotide base pairing between a 3' subdomain of the (n+2)th hairpin molecule and a 5' subdomain of the (n+2)th hairpin molecule, wherein the (n+2)th paired stem domain comprises a (n+2)th coupling segment, a (n+2)th barcode segment, and complements thereof, and (iii) a (n+2)th hairpin loop domain; extending the (n+1)th coupling segment of the (n+1)th extended oligonucleotide hybridized to the (n+2)th 3' toehold domain through the (n+2)th paired stem domain of the (n+2)th hairpin molecule, thereby displacing the 5' subdomain of the (n+2)th hairpin molecule and forming a (n+2)th extended oligonucleotide, wherein the (n+2)th extended oligonucleotide of each separate (n+2) th bead population comprises a different (n+2)th barcode segment; and pooling the separate (n+2)th bead populations to generate a (n+2)th pooled bead population. In some embodiments, n is an integer between about 1 and about 8. The method can further comprise a capping reaction, comprising: contacting a capping oligonucleotide with the (n+2) th extended oligonucleotide, wherein the capping oligonucleotide is a single-stranded molecule comprising a 3' region capable of annealing to the 3' end of the (n+2)th extended oligonucleotide; and extending the (n+2)th extended oligonucleotide hybridized with the capping oligonucleotide, thereby generating a capped oligonucleotide, thereby generating a population of capped beads.

Steps (b), (c), (f) and/or (g) can be performed under conditions that result in annealing, nucleic acid polymerization, and strand displacement. In some embodiments, the contacting steps and extending steps are performed isothermally or performed at greater than about 37° C., 50° C., or 60° C. In some embodiments, the contacting steps and extending steps comprise thermocycling. Thermocycling can comprise periodically adjusting the temperature of the contacting steps and/or extending steps. Thermocycling can be performed at about 37° C. to at about 60° C. In some embodiments, varying the temperature of the reaction during the incubation period (between 37 and 60° C.) can help the primers exit any kinetic traps that might be impeding the efficient completion of the extension. The contacting steps and extending steps can be performed in the presence of a polymerase having strand displacement activity (e.g., phi29 DNA polymerase, Bst DNA polymerase, Bsu DNA polymerase, Klenow Fragment DNA polymerase, or any combination thereof) and deoxyribonucleotide triphosphates (dNTPs). In some embodiments, the beads are not washed between steps. Step (c) can comprise: displacing the first extended oligonucleotide from the first hairpin molecule through intramolecular nucleotide base pairing between the 3' subdomain of first hairpin molecule and the 5' subdomain of first hairpin molecule. Step (g) can comprise displacing the second extended oligonucleotide from the second hairpin molecule through intramolecular nucleotide base pairing between the 3' subdomain of the second hairpin molecule and the 5' subdomain of the second hairpin molecule. Separating the first pooled bead population into a plurality of separate second bead populations can comprise partitioning the first pooled bead population to a plurality of partitions (e.g., wells, microwells, tubes, vials, microcapsules, droplets, or any combination thereof).

Each separate first bead population can be contacted with a first hairpin molecule comprising a different first barcode segment. Each separate second bead population can be contacted with a second hairpin molecule comprising a different second barcode segment. Each separate third bead population can be contacted with a third hairpin molecule comprising a different third barcode segment. Each separate fourth bead population can be contacted with a fourth hairpin molecule comprising a different fourth barcode segment. The first barcode segment can be selected from a first set of barcode segments. The second barcode segment can be selected from a second set of barcode segments. The first set of barcode segments and the second set of barcode segments can be identical. The first set of barcode segments and the second set of barcode segments can be different. The third barcode segment can be selected from a third set of barcode segments. The fourth barcode segment can be selected from a fourth set of barcode segments. In some embodiments, the first set of barcode segments, the second set of barcode segments, the third set of barcode segments, and/or the fourth set of barcode segments can be identical. In some embodiments, the first set of barcode segments, the second set of barcode segments, the third set of barcode segments, and/or the fourth set of barcode segments can be different. The first set of barcode segments, the second set of barcode segments, the third set of barcode segments, and/or the fourth set of barcode segments can have identical lengths or different lengths. The oligonucleotide can comprise a barcode comprising the first barcode segment, the second barcode segment, the third barcode segment, and/or the fourth barcode segment.

In some embodiments, there are m separate first bead populations, there are n separate second bead populations, and the second pooled bead population is capable of comprising m*n unique barcodes. In some embodiments, there are o separate third bead populations, and the third pooled bead population is capable of comprising m*n*o unique barcodes. In some embodiments, there are p separate fourth bead populations, and the fourth pooled bead population is capable of comprising m*n*o*p unique barcodes. In some embodiments, the plurality of oligonucleotides of the same bead comprise the same barcode (e.g., bead barcode), and wherein oligonucleotides on different beads comprise different bead barcodes. In some embodiments, the plurality of oligonucleotides of the same bead comprise identical first barcode segments and identical second barcode segments. The plurality of oligonucleotides of the same bead can comprise identical first barcode segments, identical second barcode segments, identical third barcode segments, and identical fourth barcode segments. In some embodiments, two beads do not comprise the same combination of first barcode segments, second barcode segments, third barcode segments, and/or fourth barcode segments.

Each first hairpin molecule can comprise an identical first coupling segment. Each second hairpin molecule can comprise an identical second coupling segment. Each third hairpin molecule can comprise an identical third coupling segment. Each fourth hairpin molecule can comprise an identical fourth coupling segment. In some embodiments, the first coupling segment, second coupling segment, third coupling segment, and/or fourth coupling segment are different. The 5' subdomain of the first hairpin molecule can comprise the first coupling segment and the first barcode segment.

The first extended oligonucleotide can comprise the input primer, the first barcode segment, and the first coupling segment. The second extended oligonucleotide can comprise the input primer, the first barcode segment, the first coupling segment, the second barcode segment, and the second coupling segment.

In some embodiments, the method can comprise a capping reaction. In some embodiments, the capping reaction comprises: contacting a capping oligonucleotide with the first extended oligonucleotide, the second extended oligonucleotide, the third extended oligonucleotide, and/or the fourth extended oligonucleotide, wherein the capping oligonucleotide is a single-stranded molecule comprising a 3' region capable of annealing to the 3' end of the first extended oligonucleotide, the second extended oligonucleotide, the third extended oligonucleotide, or the fourth extended oligonucleotide; and extending the first extended oligonucleotide, the second extended oligonucleotide, the third extended oligonucleotide, and/or the fourth extended oligonucleotide hybridized with the capping oligonucleotide, thereby generating a capped oligonucleotide, thereby generating a population of capped beads. In some embodiments, the capping oligonucleotide comprises a polyA capping sequence. In some embodiments, the polyA capping sequence that has one or more ribo bases in the 3' end. In some embodiments, the one or more ribo bases in the 3' end prevent unproductive hybridization during the capping primer extension reaction. In some embodiments, the polyA capping sequence has three ribo bases in the 3' end.

In some embodiments, a single first hairpin molecule can catalyze the extension of two or more different oligonucleotides. In some embodiments, a single first hairpin molecule can catalyze the extension of ten or more different oligonucleotides. In some embodiments, a single first hairpin molecule can catalyze the extension about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, different oligonucleotides.

In some embodiments, the ratio of the oligonucleotide to the first hairpin molecule at step (b) can vary. In some embodiments, the ratio of the oligonucleotide to the first hairpin molecule at step (b) is at least 10:1. In some embodiments, the ratio of the oligonucleotide to the first hairpin molecule at step (b) is at least 100:1.The ratio of the oligonucleotide to the first hairpin molecule at step (b) may be 2:1 to 100:1. In some embodiments, ratio of the oligonucleotide to the first hairpin molecule at step (b) is 2:1, 3:1, 4:1, 5:1, 6:1, :1, 8:1, 9:1, 10:1, 11:1, 12:1, 13:1, 14:1, 15:1, 16:1, 17:1, 18:1, 19:1 or 20:1. In some embodiments, ratio of the oligonucleotide to the first hairpin molecule at step (b) is 30:1, 40:1, 50:1, 60:1, 70:1, 80:1, 90:1, 100:1, 500:1, or 1000:1.

In some embodiments, the generation of the library of barcoded beads requires at least 1, 2, 3, 4, 5, 6, 7, 8, 9, 10, 11, 12, 13, 14, 15, 16, 17, 18, 19, or 20 folds less input nucleic acid as compared to a ligation-based method of bead barcoding. In some embodiments, the generation of the library of barcoded beads requires at least ten-fold less input nucleic acid as compared to a ligation-based method of bead barcoding. In some embodiments, the generation of the library of barcoded beads requires at least hundred-fold less input nucleic acid as compared to a ligation-based method of bead barcoding.

In some embodiments, the generation of the library of barcoded beads requires at least 1, 2, 3, 4, 5, 6, 7, 8, 9, 10, 11, 12, 13, 14, 15, 16, 17, 18, 19, or 20 fold less input nucleic acid as compared to a non-PER extension-based method of bead barcoding. In some embodiments, the generation of the library of barcoded beads requires at least ten-fold less input nucleic acid as compared to a non-PER extension-based method of bead barcoding. In some embodiments, the generation of the library of barcoded beads requires at least hundred-fold less input nucleic acid as compared to a non-PER extension-based method of bead barcoding.

As described above, oligonucleotides incorporating a combination of barcode segments can function as a unique identifier of a bead. Additionally, said oligonucleotides may also include additional sequences, such as, for example, primer sequences, primer annealing site sequences, immobilization sequences, or other recognition or binding sequences useful for subsequent processing, e.g., a sequencing primer or primer binding site for use in sequencing of samples to which the barcode containing oligonucleotide is attached.

The length of a barcode segment may be any suitable length, depending on the application. In some embodiments, a barcode segment may be about 2 to about 500 nucleotides in length, about 2 to about 100 nucleotides in length, about 2 to about 50 nucleotides in length, about 2 to about 20 nucleotides in length, about 6 to about 20 nucleotides in length, or about 4 to 16 nucleotides in length. In some embodiments, a barcode segment is about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some embodiments, a barcode segment is greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some embodiments, a barcode segment is less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length. A bead barcode can comprise 1 or more barcode segments. A bead barcode can comprise about 2, 3, 4, 5, 6, 7, 8, 9, 10, 11, 12, 13, 14, 15, 16, 17, 18, 19, 20, 25, 30, 35, 40, 45, 50 barcode segments.

The beads provided herein may be attached to oligonucleotide sequences that are random, pseudo-random, or targeted N-mers. The length of an N-mer may vary. In some embodiments, an N-mer (e.g., a random N-mer, a pseudo-random N-mer, or a targeted N-mer) may be between about 2 and about 100 nucleotides in length, between about 2 and about 50 nucleotides in length, between about 2 and about 20 nucleotides in length, between about 5 and about 25 nucleotides in length, or between about 5 and about 15 nucleotides in length. In some embodiments, an N-mer (e.g., a random N-mer, a pseudo-random N-mer, or a targeted N-mer) may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some embodiments, an N-mer (e.g., a random N-mer, a pseudo-random N-mer, or targeted a N-mer) may be greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some embodiments, an N-mer (e.g., a random N-mer, a pseudo-random N-mer, or a targeted N-mer) may be less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length.

The barcode segments may be independently selected from a set of 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 different barcode segments. The barcode segments or the first and second barcode segments may each be selected from separate sets of barcode segments. Moreover, the barcode segments may individually and independently comprise from 2 to 20 nucleotides in length, preferably from about 4 to about 20 nucleotides in length, more preferably from about 4 to about 16 nucleotides in length or from about 4 to about 10 nucleotides in length. In some embodiments, the barcode segments may individually and independently comprise at least 2, 3, 4, 5, 6, 7, 8, 9, 10, 11, 12, 13, 14, 15, 16, 17, 18, 19, 20, or more nucleotides in length. In particular, the barcode segments may comprise 2-mers, 3-mers, 4-mers, 5-mers, 6-mers, 7-mers, 8-mers, 9-mers, 10-mers, 11-mers, 12-mers, 13-mers, 14-mers, 15-mers, 16-mers, 17-mers, 18-mers, 19-mers, 20-mers, or longer segments.

In some embodiments, barcodes (e.g., bead barcodes) comprise about 2, 3, 4, 5, 6, 7, 8, 9, 10, 11, 12, 13, 14, 15, 16, 17, 18, 19, 20, or more barcode segments. In some embodiments, barcodes will typically represent at least 2 different barcode segment combinations, at least 4 different barcode segment combinations, at least 6 different barcode segment combinations, at least 8 different barcode segment combinations, at least 10 different barcode segment combinations, at least 50 different barcode segment combinations, at least 100 different barcode segment combinations, at least 500 different barcode segment combinations, at least 1,000 different barcode segment combinations, at least about 2,000 different barcode segment combinations, at least about 4,000 different barcode segment combinations, at least about 5,000 different barcode segment combinations, at least about 10,000 different barcode segment combinations, at least 50,000 different barcode segment combinations, at least 100,000 barcode segment combinations, at least 500,000 segment combinations, at least 1,000,000 barcode segment combinations, or more. As a result, resulting barcode libraries may range in diversity of from at least about 100 different barcode segment combinations to at least about 1,000,000, 2,000,000, 5,000,000, 10,000,000 100,000,000 or more different barcode segment combinations as described elsewhere herein, being represented within the library.

In some embodiments described herein, individual beads comprise oligonucleotides attached thereto that have a common overall combination of barcode segments (a "bead barcode"). As described herein, where a bead includes oligonucleotides having a common bead barcode, it is generally meant that of the oligonucleotides coupled to a given bead, a significant percentage, e.g., greater than 70%, greater than 80%, greater than 90%, greater than 95% or even greater than 99% of the oligonucleotides of or greater than a given length, e.g., including the full expected length or lengths of final oligonucleotides and excluding unreacted anchor sequences or partial barcode sequences, include the same or identical barcode segments. This bead barcode (again, which may be comprised of two or more barcode segments separated by one or more bases) may be included among other common or variable sequences or domains within a single bead.

Beads may contain one or more attached barcodes and/or UMIs (e.g., N-mers). The barcode sequences attached to a single bead may be identical (e.g., a bead barcode) or different. In some embodiments, each bead may be attached to about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 identical barcodes (e.g., bead barcodes). In some embodiments, each bead may be attached to about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 different UMIs.

An individual barcode library may comprise one or more barcoded beads. In some embodiments, an individual barcode library may comprise about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 individual barcoded beads. In some embodiments, each library may comprise at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more individual barcoded beads. In some embodiments, each library may comprise less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 1000000000, 5000000000, 10000000000, 50000000000, or 100000000000 individual barcoded beads. The barcoded beads within the library may have the same sequences or different sequences.

In some embodiments, each bead may have a unique bead barcode. However, the number of beads with unique barcode sequences within a barcode library may be limited by combinatorial limits. In some embodiments, the percentage of multiple copies of the same bead barcode within a given library may be 1%, 2%, 3%, 4%, 5%, 6%, 7%, 8%, 9%, 10%, 15%, 20%, 25%, 30%, 40%, or 50%. In some embodiments, the percentage of multiple copies of the same bead barcode within a given library may be more than 1%, 2%, 3%, 4%, 5%, 6%, 7%, 8%, 9%, 10%, 15%, 20%, 25%, 30%, 40%, 50% or more. In some embodiments, the percentage of multiple copies of the same bead barcode within a given library may be less than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, or 50%.

In some embodiments, each bead may comprise one unique bead barcode but multiple different random N-mers (e.g., UMIs). In some embodiments, each bead may have one or more different random N-mers. Again, the number of beads with different random N-mers within a barcode library may be limited by combinatorial limits. For example, using four different nucleotides, if an N-mer sequence is 12 nucleotides in length, than the number of different constructs may be limited to $4^{12}=16777216$ different constructs. Since barcode libraries may comprise many more beads than 16777216, there may be some libraries with multiple copies of the same N-mer sequence. In some embodiments, the percentage of multiple copies of the same N-mer sequence within a given library may be 1%, 2%, 3%, 4%, 5%, 6%, 7%, 8%, 9%, 10%, 15%, 20%, 25%, 30%, 40%, or 50%. In some embodiments, the percentage of multiple copies of the same N-mer sequence within a given library may be more than 1%, 2%, 3%, 4%, 5%, 6%, 7%, 8%, 9%, 10%, 15%, 20%, 25%, 30%, 40%, 50% or more. In some embodiments, the percentage of multiple copies of the same N-mer sequence within a given library may be less than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, or 50%.

Compositions for Use in Nucleic Acid Barcoding

There are provided, in some embodiments, compositions for use in nucleic acid barcoding. In some embodiments, there are provided compositions comprising barcoded particles generated according to the methods provided herein. The methods, compositions, devices, and kits of this disclosure may be used with any suitable particle (e.g., bead). In some embodiments, a particle (e.g., bead) may be porous, non-porous, solid, semi-solid, semi-fluidic, or fluidic. In some embodiments, a particle (e.g., bead) may be dissolvable, disruptable, or degradable. In some embodiments, a particle (e.g., bead) may not be degradable. In some embodiments, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some embodiments, the beads are silica beads. In some embodiments, the beads are rigid. In some embodiments, the beads may be flexible.

Additionally, there are provided, in some embodiments, gel beads degradable upon application of a chemical stimulus that comprise releasably attached oligonucleotides. Included within this disclosure are bead compositions that include diverse sets of reagents, such as diverse libraries of beads attached to large numbers of oligonucleotides containing barcode sequences, and methods of making and using the same. Beads may serve as a support on which to synthesize oligonucleotide sequences. In some embodiments, a PER-catalyzed extension or other reaction may be used to synthesize an oligonucleotide on a bead via a primer attached to the bead. The PER input primer can then be extended by the methods provided herein, thereby generating a library of barcoded beads. In some embodiments, the composition comprises: a first hairpin molecule, comprising (i) a first 3' toehold domain, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; and a gel bead releasably attached to a plurality of oligonucleotides each comprising an input primer hybridized to the 3' toehold domain of a first hairpin molecule, wherein the input primer is complementary to the 3' toehold domain of the first hairpin molecule. There are provided, in some embodiments, compositions for use in nucleic acid barcoding. In some embodiments, the composition comprises: a first hairpin molecule, comprising (i) a first 3' toehold domain, (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, and (iii) a first hairpin loop domain; and a plurality of gel beads releasably attached to a plurality of oligonucleotides each comprising an input primer hybridized to the 3' toehold domain of a first hairpin molecule, wherein the input primer is complementary to the 3' toehold domain of the first hairpin molecule.

FIG. 5A is a schematic illustration showing a non-limiting exemplary embodiment of a hydrogel bead composition prepared with acrylamide, N,N-bis(acryloyl)cystamine, and acrydite-modified DNA. The oligonucleotides can be releasable upon application of a stimulus. The gel beads can be degradable upon application of a chemical stimulus. The gel bead can comprise chemically reducible cross-linkers (e.g., disulfide linkages). The chemical stimulus can comprise a reducing agent (e.g., dithiothreitol (DTT), tris(2-carboxyethyl)phosphine (TCEP)). In some embodiments, the gel bead does not comprise a photo-cleavable linker.

FIG. 5B is a schematic illustration showing a non-limiting exemplary embodiment of USER enzyme-mediated cleavage of a particle-associated oligonucleotide comprising deoxyuridine. The oligonucleotides can be attached to the gel bead by an acrydite moiety. The oligonucleotides can comprise single-stranded DNA. The oligonucleotides can comprise deoxyuridine. The stimulus can comprise USER (Uracil-Specific Excision Reagent) enzyme.

The plurality of gel beads can comprise at least 1,000 gel beads. In some embodiments, the number of gel beads can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. The plurality of gel beads can have substantially uniform cross-sectional dimensions. The plurality of gel beads can have a coefficient of variation in cross-sectional dimension of less than 30%. The gel bead can have a cross-sectional dimension between about 10 micrometers and about 100 micrometers. The oligonucleotides can comprise an immobilization sequence (e.g., P5). The 5' subdomain of the first hairpin molecule can comprise the first coupling segment and the first barcode segment. In some embodiments, at least two oligonucleotides are hybridized to first hairpin molecules comprising different first barcode segments, wherein said at least two oligonucleotides hybridized to first hairpin molecules comprising different first barcode segments are located in separate partitions (e.g., wells, microwells, tubes, vials, microcapsules, droplets). At least 100,000 oligonucleotides can be releasably attached to a gel bead and each of the at least 100,000 oligonucleotides can comprise an identical bead barcode sequence. The identical bead barcode sequence can be different across different gel beads. The oligonucleotides can comprise unique identifiers (e.g., UMI) that can be different across said oligonucleotides.

In some embodiments, the bead may contain molecular precursors (e.g., monomers or polymers), which may form a polymer network via polymerization of the precursors. In some embodiments, a precursor may be an already polymerized species capable of undergoing further polymerization via, for example, a chemical cross-linkage. In some embodiments, a precursor comprises one or more of an acrylamide or a methacrylamide monomer, oligomer, or polymer. In some embodiments, the bead may comprise prepolymers, which are oligomers capable of further polymerization. For example, polyurethane beads may be prepared using prepolymers. In some embodiments, the bead may contain individual polymers that may be further polymerized together. In some embodiments, beads may be generated via polymerization of different precursors, such that they comprise mixed polymers, co-polymers, and/or block co-polymers.

A particle (e.g., bead) may comprise natural and/or synthetic materials, including natural and synthetic polymers. Examples of natural polymers include proteins and sugars such as deoxyribonucleic acid, rubber, cellulose, starch (e.g. amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and combinations (e.g., co-polymers) thereof. Particles (e.g., beads) may also be formed from materials other than polymers, including lipids, micelles, ceramics, glass-ceramics, material composites, metals, other inorganic materials, and others.

In some embodiments, a chemical cross-linker may be a precursor used to cross-link monomers during polymerization of the monomers and/or may be used to functionalize a bead with a species. In some embodiments, polymers may be further polymerized with a cross-linker species or other type of monomer to generate a further polymeric network. Non-limiting examples of chemical cross-linkers (also referred to as a "crosslinker" or a "crosslinker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilance, N,N' diallyltartardiamide (DATD), N,N'-Bis(acryloyl)cystamine (BAC), or homologs thereof. In some embodiments, the crosslinker used in the present disclosure contains cystamine Crosslinking may be permanent or reversible, depending upon the particular crosslinker used. Reversible crosslinking may allow for the polymer to linearize or dissociate under appropriate conditions. In some embodiments, reversible cross-linking may also allow for reversible attachment of a material bound to the surface of a bead. In some embodiments, a cross-linker may form disulfide linkages. In some embodiments, the chemical cross-linker forming disulfide linkages may be cystamine or a modified cystamine. In some embodiments, disulfide linkages may be formed between molecular precursor units (e.g. monomers, oligomers, or linear polymers). In some embodiments, disulfide linkages may be may be formed between molecular precursor units (e.g. monomers, oligomers, or linear polymers) or precursors incorporated into a bead and oligonucleotides.

Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In at least one alternative example, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some embodiments, the bead may comprise covalent or ionic bonds between polymeric precursors (e.g. monomers, oligomers, linear polymers), oligonucleotides, primers, and other entities. In some embodiments, the covalent bonds comprise carbon-carbon bonds or thioether bonds.

In some embodiments, a bead may comprise an acrydite moiety, which in certain aspects may be used to attach one or more species (e.g., barcode sequence, primer, other oligonucleotide) to the bead. In some embodiments, an acrydite moiety can refer to an acrydite analogue generated from the reaction of acrydite with one or more species, such as, for example, the reaction of acrydite with other monomers and cross-linkers during a polymerization reaction. Acrydite moieties may be modified to form chemical bonds with a species to be attached, such as an oligonucleotide (e.g., barcode sequence, primer, other oligonucleotide). For example, acrydite moieties may be modified with thiol groups capable of forming a, disulfide bond or may be modified with groups already comprising a disulfide bond. The thiol or disulfide (via disulfide exchange) may be used as an anchor point for a species to be attached or another part of the acrydite moiety may be used for attachment. In some embodiments, attachment is reversible, such that when the disulfide bond is broken (e.g., in the presence of a reducing agent), the agent is released from the bead. In other embodiments, an acrydite moiety comprises a reactive hydroxyl group that may be used for attachment.

Functionalization of beads for attachment of other species, e.g., nucleic acids, may be achieved through a wide range of different approaches, including activation of chemical groups within a polymer, incorporation of active or activatable functional groups in the polymer structure, or attachment at the pre-polymer or monomer stage in bead production.

For example, in some examples, precursors (e.g., monomers, cross-linkers) that are polymerized to form a bead may comprise acrydite moieties, such that when a bead is generated, the bead also comprises acrydite moieties. In some embodiments, the acrydite moieties are attached to an oligonucleotide sequence, such as a primer (e.g., a primer for one or more of amplifying target nucleic acids and/or sequencing target nucleic acids barcode sequence, binding sequence, or the like)) that is desired to be incorporated into the bead. In some embodiments, the primer comprises a P5 sequence. For example, acrylamide precursors (e.g., cross-linkers, monomers) may comprise acrydite moieties such that when they are polymerized to form a bead, the bead also comprises acrydite moieties.

In some embodiments, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some embodiments, acrylic acid (a species comprising free COOH groups), acrylamide, and bis(acryloyl) cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange)) such that the species can be linked to the beads (e.g., via a generated disulfide bond). In some embodiments, though, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some embodiments, uncontrolled reactions can be prevented by inclusion of a thiol capping agent such as, for example, N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some embodiments, a low concentration (e.g., molecules of reducing agent:gel bead ratios of less than about 10000, 100000, 1000000, 10000000, 100000000, 1000000000, 10000000000, or 100000000000) of reducing agent may be used for reduction. Controlling the number of disulfide linkages that are reduced to free thiols may be useful in ensuring bead structural integrity during functionalization. In some embodiments, optically-active agents, such as fluorescent dyes may be may be coupled to beads via free thiol groups of the beads and used to quantify the number of free thiols present in a bead and/or track a bead.

In some embodiments, acrydite moieties linked to precursors, another species linked to a precursor, or a precursor itself comprise a labile bond, such as, for example, chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some embodiments, a thermally labile bond may include a nucleic acid hybridization-based attachment, e.g., where an oligonucleotide is hybridized to a complementary sequence that is attached to the bead, such that thermal melting of the hybrid releases the oligonucleotide, e.g., a barcode containing sequence, from the bead or microcapsule. Moreover, the addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some embodiments, another species comprising a labile bond may be linked to a gel bead after gel bead formation via, for example, an activated functional group of the gel bead as described above.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

A bead may be linked to a varied number of acrydite moieties. For example, a bead may comprise about 1, 10, 100, 1000, 10000, 100000, 1000000, 10000000, 100000000, 1000000000, or 10000000000 acrydite moieties linked to the beads. In other examples, a bead may comprise at least 1, 10, 100, 1000, 10000, 100000, 1000000, 10000000, 100000000, 1000000000, or 10000000000 acrydite moieties linked to the beads. For example, a bead may comprise about 1, 10, 100, 1000, 10000, 100000, 1000000, 10000000, 100000000, 1000000000, or 10000000000 oligonucleotides covalently linked to the beads, such as via an acrydite moiety. In other examples, a bead may comprise at least 1, 10, 100, 1000, 10000, 100000, 1000000, 10000000, 100000000, 1000000000, or 10000000000 oligonucleotides covalently linked to the beads, such as via an acrydite moiety.

Species that do not participate in polymerization may also be encapsulated in beads during bead generation (e.g., during polymerization of precursors). Such species may be entered into polymerization reaction mixtures such that generated beads comprise the species upon bead formation. In some embodiments, such species may be added to the gel beads after formation. Such species may include, for example, oligonucleotides, species necessary for a nucleic acid amplification reaction (e.g., PER input primers, primers, polymerases, dNTPs, co-factors (e.g., ionic co-factors)) including those described herein, species necessary for enzymatic reactions (e.g., enzymes, co-factors, substrates), or species necessary for a nucleic acid modification reaction such as polymerization, ligation, or digestion. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead.

Beads may be of uniform size or heterogeneous size. In some embodiments, the diameter of a bead may be about 1 μm, 5 μm, 10 μm, 20 μm, 30 μm, 40 μm, 45 μm, 50 μm, 60 μm, 65 μm, 70 μm, 75 μm, 80 μm, 90 μm, 100 μm, 250 μm, 500 μm, or 1 mm. In some embodiments, a bead may have a diameter of at least about 1 μm, 5 μm, 10 μm, 20 μm, 30 μm, 40 μm, 45 μm, 50 μm, 60 μm, 65 μm, 70 μm, 75 μm, 80 μm, 90 μm, 100 μm, 250 μm, 500 μm, 1 mm, or more. In some embodiments, a bead may have a diameter of less than about 1 μm, 5 μm, 10 μm, 20 μm, 30 μm, 40 μm, 45 μm, 50 μm, 60 μm, 65 μm, 70 μm, 75 μm, 80 μm, 90 μm, 100 μm, 250 μm, 500 μm, or 1 mm. In some embodiments, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain preferred aspects, the beads are provided as a population of beads having a relatively monodisperse size distribution. As will be appreciated, in some applications, where it is desirable to provide relatively consistent amounts of reagents within partitions, maintaining relatively consistent bead characteristics, such as size, contributes to that overall consistency. In particular, the beads described herein may have size distributions that have a coefficient of variation in their cross-sectional dimensions of less than 50%, less than 40%, less than 30%, less than 20%, and in some embodiments less than 15%, less than 10%, or even less than 5%. Beads may be of a regular shape or an irregular shape. Examples of bead shapes include spherical, non-spherical, oval, oblong, amorphous, circular, cylindrical, and homologs thereof.

Degradable Beads

In addition to, or as an alternative to the cleavable linkages between the beads and the associated oligonucleotides (e.g., oligonucleotides comprising deoxyuridine as described above) the beads may be degradable, disruptable, or dissolvable spontaneously or upon exposure to one or more stimuli (e.g., temperature changes, pH changes, exposure to particular chemical species or phase, exposure to light, reducing agent, etc.). In some embodiments, a bead may be dissolvable, such that material components of the beads are solubilized when exposed to a particular chemical species or an environmental change, such as, for example, temperature, or pH. For example, a gel bead may be degraded or dissolved at elevated temperature and/or in basic conditions. In some embodiments, a bead may be thermally degradable such that when the bead is exposed to an appropriate change in temperature (e.g., heat), the bead degrades. Degradation or dissolution of a bead bound to a species (e.g., a nucleic acid species) may result in release of the species from the bead.

A degradable bead may comprise one or more species with a labile bond such that when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some embodiments, a cross-linker used to generate a bead may comprise a labile bond. Upon exposure to the appropriate conditions, the labile bond is broken and the bead is degraded. For example, a polyacrylamide gel bead may comprise cystamine crosslinkers. Upon exposure of the bead to a reducing agent, the disulfide bonds of the cystamine are broken and the bead is degraded.

A degradable bead may be useful in more quickly releasing an attached species (e.g., an oligonucleotide, a barcode sequence) from the bead when the appropriate stimulus is applied to the bead. For example, for a species bound to an inner surface of a porous bead or in the case of an encapsulated species, the species may have greater mobility and accessibility to other species in solution upon degradation of the bead. In some embodiments, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species are released within the droplet when the appropriate stimulus is applied. The free species may interact with other species. For example, a polyacrylamide bead comprising cystamine and linked, via a disulfide bond, to a barcode sequence, may be combined with a reducing agent within a droplet of a water-in-oil emulsion. Within the droplet, the reducing agent breaks the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some embodiments, an increase in pore size due to osmotic swelling of a bead can permit the release of entrained species within the bead. In other embodiments, osmotic shrinking of a bead may cause a bead to better retain an entrained species due to pore size contraction.

In some embodiments, a stimulus may be used to trigger degrading of the bead, which may result in the release of contents from the bead. Generally, a stimulus may cause degradation of the bead structure, such as degradation of the covalent bonds or other types of physical interaction. These stimuli may be useful in inducing a bead to degrade and/or to release its contents. Examples of stimuli that may be used include chemical stimuli, thermal stimuli, light stimuli and any combination thereof. Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

FIG. 5A is a schematic illustration showing a non-limiting exemplary embodiment of a hydrogel bead composition prepared with acrylamide, N,N-bis(acryloyl)cystamine (BAC), and acrydite-modified DNA. In some embodiments provided herein, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include beta-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other embodiments, a change in pH of a solution, such as an increase in pH, may trigger degradation of a bead. In other embodiments, exposure to an aqueous solution, such as water, may trigger hydrolytic degradation, and thus degrading the bead.

A degradable bead may degrade instantaneously upon application of the appropriate stimuli. In other embodiments, degradation of the bead may occur over time. For example, a bead may degrade upon application of an appropriate stimulus instantaneously or within about 0, 0.01, 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15 or 20 minutes. In other examples, a bead may degrade upon application of a proper stimulus instantaneously or within at most about 0, 0.01, 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15 or 20 minutes.

Methods of Preparing Hydrogel Beads Described Herein

The beads described herein may be produced using a variety of methods. In some embodiments, beads may be formed from a liquid containing molecular precursors (e.g. linear polymers, monomers, cross-linkers). The liquid is then subjected to a polymerization reaction, and thereby hardens or gels into a bead (or gel bead). The liquid may also contain entities such as oligonucleotides that become incorporated into the bead during polymerization. This incorporation may be via covalent or non-covalent association with the bead. For example, in some embodiments, the oligonucleotides may be entrained within a bead during formation. Alternatively, they may be coupled to the bead or the bead framework either during formation or following formation. In some embodiments, the oligonucleotides are connected to an acrydite moiety that becomes cross-linked to the bead during the polymerization process. In some embodiments, the oligonucleotides are attached to the acrydite moiety by a disulfide linkage. As a result, a composition comprising a bead-acrydite-S-S-oligonucleotide linkage is formed. FIG. 5A is a schematic illustration showing a non-limiting exemplary embodiment of a hydrogel bead composition prepared with acrylamide, N,N-bis (acryloyl)cystamine, and acrydite-modified DNA.

In one exemplary process, functionalized beads may be generated by mixing a plurality of polymers and/or monomers with one or more oligonucleotides, such as, for example, one or more oligonucleotides that comprises a primer (e.g., a universal primer, a sequencing primer). The polymers and/or monomers may comprise acrylamide and may be crosslinked such that disulfide bonds form between the polymers and/or monomers, resulting in the formation of hardened beads. The oligonucleotides may be covalently linked to the plurality of polymers and/or monomers during the formation of the hardened beads (e.g., contemporaneously) or may be covalently linked to the plurality of polymers and/or monomers after the formation of the hardened beads (e.g., sequentially). In some embodiments, the oligonucleotides may be linked to the beads via an acrydite moiety.

In most embodiments, a population of beads is pre-functionalized with the identical oligonucleotide such as a universal primer or primer binding site. In some embodiments, the beads in a population of beads are pre-functionalized with multiple different oligonucleotides. These oligonucleotides may optionally include any of a variety of different functional sequences, e.g., for use in subsequent processing or application of the beads (e.g., a PER input primer). Functional sequences may include, e.g., a PER input primer, primer sequences, such as targeted primer sequences, universal primer sequences, e.g., primer sequences that are sufficiently short to be able to hybridize to and prime extension from large numbers of different locations on a sample nucleic acid, or random primer sequences, attachment or immobilization sequences, ligation sequences, hairpin sequences, tagging sequences, e.g., barcodes or sample index sequences, or any of a variety of other nucleotide sequences.

By way of example, in some embodiments, the oligonucleotide comprises an input primer to enable attachment of additional content(s) (e.g., barcodes, random N-mers, other functional sequences) to the bead according to the methods provided herein. In some embodiments, the oligonucleotide comprises a universal primer (e.g., P5) which may also be compatible with a sequencing device, and may later enable attachment of a desired strand to a flow cell within the sequencing device. For example, such attachment or immobilization sequences may provide a complementary sequence to oligonucleotides that are tethered to the surface of a flow cell in a sequencing device, to allow immobilization of the sequences to that surface for sequencing. Alternatively, such attachments sequences may additionally be provided within, or added to the oligonucleotide sequences attached to the beads. In some embodiments, the beads and their attached species may be provided to be compatible with subsequent analytical process, such as sequencing devices or systems. In some embodiments, more than one primer may be attached to a bead and more than one primer may contain a universal sequence, in order to, for example, allow for differential processing of the oligonucleotide as well as any additional sequences that are coupled to that sequence, in different sequential or parallel processing steps, e.g., a first primer for amplification of a target sequence, with a second primer for sequencing the amplified product. For example, in some embodiments, the oligonucleotides attached to the beads will comprise a first primer sequence for conducting a first amplification or replication process, e.g., extending the primer along a target nucleic acid sequence, in order to generate an amplified barcoded target sequence(s). By also including a sequencing primer within the oligonucleotides, the resulting amplified target sequences will include such primers, and be readily transferred to a sequencing system. For example, in some embodiments, e.g., where one wishes to sequence the amplified targets using, e.g., an Illumina sequencing system, an R1 primer or primer binding site may also be attached to the bead.

Polymerization may occur spontaneously in some embodiments. In some embodiments, polymerization may be initiated by an initiator and/or an accelerator, by electromagnetic radiation, by temperature changes (e.g., addition or removal of heat), by pH changes, by other methods, and combinations thereof. An initiator may refer to a species capable of initiating a polymerization reaction by activating (e.g., via the generation of free radicals) one or more precursors used in the polymerization reaction. An accelerator may refer to a species capable of accelerating the rate at which a polymerization reaction occurs. In some embodiments, an accelerator may speed up the activation of an initiator (e.g., via the generation of free radicals) used to then activate monomers (e.g., via the generation of free radicals) and, thus, initiate a polymerization reaction. In some embodiments, faster activation of an initiator can give rise to faster polymerization rates. In some embodiments, though, acceleration may also be achieved via non-chemical means such as thermal (e.g., addition and removal of heat) means, various types of radiative means (e.g., visible light, UV light, etc.), or any other suitable means. To create droplets containing molecular precursors, which may then polymerize to form hardened beads, an emulsion technique may be employed. For example, molecular precursors may be added to an aqueous solution. The aqueous solution may then be emulsified with an oil (e.g., by agitation, microfluidic droplet generator, or other method). The molecular precursors may then be polymerized in the emulsified droplets to form the beads.

An emulsion may be prepared, for example, by any suitable method, including methods known in the art, such as bulk shaking, bulk agitation, flow focusing, and microsieve. In some embodiments, an emulsion may be prepared using a microfluidic device. In some embodiments, water-in-oil emulsions may be used. In some embodiments, oil-in-water emulsions may be used. In some embodiments, polydisperse emulsions may be formed. In some embodiments, monodisperse emulsions may be formed. In some embodiments, monodisperse emulsions may be formed in a microfluidic flow focusing device.

In at least one example, a microfluidic device for making the beads may contain channel segments that intersect at a single cross intersection that combines two or more streams of immiscible fluids, such as an aqueous solution containing molecular precursors and an oil. Combining two immiscible fluids at a single cross intersection may cause fluidic droplets to form. The size of the fluidic droplets formed may depend upon the flow rate of the fluid streams entering the fluidic cross, the properties of the two fluids, and the size of the microfluidic channels. Initiating polymerization after formation of fluidic droplets exiting the fluidic cross may cause hardened beads to form from the fluidic droplets.

To manipulate when individual molecular precursors, oligomers, or polymers begin to polymerize to form a hardened bead, an initiator and/or accelerator may be added at different points in the bead formation process. An accelerator may be an agent which may initiate the polymerization process (e.g., in some embodiments, via activation of a polymerization initiator) and thus may reduce the time for a bead to harden. In some embodiments, a single accelerator or a plurality of accelerators may be used for polymerization. Careful tuning of acceleration can be important in achieving suitable polymerization reactions. For example, if acceleration is too fast, weight and excessive chain transfer events may cause poor gel structure and low loading of any desired species. If acceleration is too slow, high molecular weight polymers can generate trapped activation sites (e.g., free radicals) due to polymer entanglement and high viscosities. High viscosities can impede diffusion of species intended for bead loading, resulting in low to no loading of the species. Tuning of accelerator action can be achieved, for example, by selecting an appropriate accelerator, an appropriate combination of accelerators, or by selecting the appropriate accelerator(s) and any stimulus (e.g., heat, electromagnetic radiation (e.g., light, UV light), another chemical species, etc.) capable of modulating accelerator action. Tuning of initiator action may also be achieved in analogous fashion.

An accelerator may be water-soluble, oil-soluble, or may be both water-soluble and oil-soluble. For example, an accelerator may be tetramethylethylenediamine (TMEDA or TEMED), dimethylethylenediamine, N,N,N,'N'-tetramethylmethanediamine, N,N'-dimorpholinomethane, or N,N,N', N'-Tetrakis(2-Hydroxypropyl)ethylenediamine. For example, an initiator may be ammonium persulfate (APS), calcium ions, and/or water-soluble azo-based initiators. Azo-based initiators may be used in the absence of TEMED and APS and can function as thermal based initiators. A thermal based initiator can activate species (e.g., via the generation of free radicals) thermally and, thus, the rate of initiator action can be tuned by temperature and/or the concentration of the initiator. A polymerization accelerator or initiator may include functional groups including phosphonate, sulfonate, carboxylate, hydroxyl, albumin binding moieties, N-vinyl groups, and phospholipids. A polymerization accelerator or initiator may be a low molecular weight monomeric-compound. An accelerator or initiator may be a) added to the oil prior to droplet generation, b) added in the line after droplet generation, c) added to the outlet reservoir after droplet generation, or d) combinations thereof.

Polymerization may also be initiated by electromagnetic radiation. Certain types of monomers, oligomers, or polymers may contain light-sensitive properties. Thus, polymerization may be initiated by exposing such monomers, oligomers, or polymers to UV light, visible light, UV light combined with a sensitizer, visible light combined with a sensitizer, or combinations thereof. An example of a sensitizer may be riboflavin.

The time for a bead to completely polymerize or harden may vary depending on the size of the bead, whether an accelerator may be added, when an accelerator may be added, the type of initiator, when electromagnetic radiation may be applied, the temperature of solution, the polymer composition, the polymer concentration, and other relevant parameters. For example, polymerization may be complete after about 5, 6, 7, 8, 9, 10, 11, 12, 13, 14, 15, 16, 17, 18, 19, or 20 minutes. Polymerization may be complete after more than about 5, 6, 7, 8, 9, 10, 11, 12, 13, 14, 15, 16, 17, 18, 19, 20 minutes or more. Polymerization may be complete in less than about 5, 6, 7, 8, 9, 10, 11, 12, 13, 14, 15, 16, 17, 18, 19, or 20 minutes.

Beads may be recovered from emulsions (e.g. gel-water-oil) by continuous phase exchange. Excess aqueous fluid may be added to the emulsion (e.g. gel-water-oil) and the hardened beads may be subjected to sedimentation, wherein the beads may be aggregated and the supernatant containing excess oil may be removed. This process of adding excess aqueous fluid followed by sedimentation and removal of excess oil may be repeated until beads are suspended in a given purity of aqueous buffer, with respect to the continuous phase oil. The purity of aqueous buffer may be about 80%, 90%, 95%, 96%, 97%, 98%, or 99% (v/v). The purity of aqueous buffer may be more than about 80%, 90%, 95%, 96%, 97%, 98%, 99% or more (v/v). The purity of aqueous buffer may be less than about 80%, 90%, 95%, 96%, 97%, 98%, or 99% (v/v). The sedimentation step may be repeated about 2, 3, 4, or 5 times. The sedimentation step may be repeated more than about 2, 3, 4, 5 times or more. The sedimentation step may be repeated less than about 2, 3, 4, or 5 times. In some embodiments, sedimentation and removal of the supernatant may also remove un-reacted starting materials.

EXAMPLES

Some aspects of the embodiments discussed above are disclosed in further detail in the following examples, which are not in any way intended to limit the scope of the present disclosure.

Example 1

Hydrogel Bead (HB) Production

Using a microfluidic droplet generator device a monodisperse HB population in oil emulsion was generated. The HB were 40-100 um in diameter. A redox-cleavable gel was prepared that has acrydite-modified DNA primer crosslinked with it. As described below, the emulsion was incubated overnight for complete polymerization of the HB, and then the HB were transferred to an aqueous buffer for the next steps. A novel acrydite-modified DNA primer sequence was employed comprising a dU (deoxyuridine) base after a poly T spacer (/5Acryd/TTT TTT T/ideoxyU/C TAC ACG ACG CTC TTC CGA TCT; SEQ ID NO: 45), which enables a user to cleave the DNA with the USER enzyme instead of using a photocleavable reaction. This is significant because using photocleavable primers is a considerable hassle during manufacturing and usage of such beads, since they have to be protected from light all the time. Additionally, rather than using standard acrylamide/bis acrylamide gel, the bisacrylamide was replaced with N,N-bis(acryloyl)cystamine. This is significant because the bis(acryloyl)cistamine has a disulfide bond, and thus the resulting gel can be dissolved using a reducing agent such as DTT (Dithiothreitol), rendering the beads "redox-cleavable."

Some elements of the HB generation protocol, including elements of bead production, bead washing, denaturing washing steps, are performed as described in Zilionis et al. ("Single-cell barcoding and sequencing using droplet microfluidics." Nature protocols 12.1 (2017): 44.). For the microfluidics droplet production, a Droplet Genomics Droplet Generation Microfluidic Chip was employed.

Hydrogel Bead (HB) Production with Microfluidics

AMBAC solution 19:1 molarity (4×) mix was prepared comprising: 3.6 mL Acrylamide solution (AA; 40% wt/wt), Sigma-Aldrich, cat. no. A4058-100 mL; 260 mg N,N-bis(acryloyl)cistamine (Sigma-Aldrich, cat. no. A4929); and completed to 10 mL with water. This solution was sterile filtered and stored at 4° C. 1 ml of AMBAC-primer mix was prepared by combining the reagents as shown in Table 1.

The solution was mixed by vortexing. In some embodiments, sonication and/or heat is employed to ensure components dissolve.

TABLE 1

AMBAC-PRIMER MIX

| Component | 1 ml mix (µl) | 3 ml mix (µl) | Final |
|---|---|---|---|
| Nuclease-free water | 420 | 1260 | |
| 1× TBSET buffer | 100 | 300 | 0.1× |
| 4× AMBAC solution | 250 | 750 | 1× |
| Acrydite-modified DNA primer (250 µM) (SEQ ID NO: 45) | 200 | 600 | 50 µM |
| 10% (wt/vol) APS | 30 | 90 | 0.3% (wt/vol) |
| Total | 1,000 | 3000 | |

First, 7 mL of Biorad oil (Droplet Generation Oil for EvaGreen #1864005) was mixed with 30 uL TEMED (Sigma-Aldrich, cat. no. T7024-50L). Vortexing was used to mix. Second, a 10 mL syringe was filled with TEMED-oil mix. Third, the pump was primed with this solution. Fourth, 1 to 3 mL of acrylamide mix was prepared by combining the reagents above. Fifth, ~1.5 mL was transferred by 3 mL syringe. Sixth, droplet generation was performed using Droplet Genomics Droplet generating chip V2. In some embodiments, for 60um droplets, flow rates of 1 ml/hour for the oil and 1 ml/hour for the primer mix are used. In some embodiments, increasing oil flow rate makes smaller droplets and decreasing it makes bigger droplets. Seventh, the emulsion was incubated overnight at 65° C. The beads were analyzed the next day.

Alternative ratios of the concentrations of the Acrylamide to N,N'-Bis(acryloyl)cystamine are also contemplated herein. In some embodiments, the bead gel mix is prepared as depicted in Table 2. In some embodiments, the bead gel mix is prepared fresh. In some embodiments, at least about 3 mL is prepared so as to enable more accurate weighing of the components.

TABLE 2

BEAD MIX

| reagent | molar ratio volume (1 mL) | molar ratio volume (2 mL) | molar ratio ratio |
|---|---|---|---|
| BAC (powder) | 5.825 mg | 17.5 mg | 0.006 wt/vol |
| Acrylamide solution(40%) | 139.8 | 419.4 | 0.145 |
| TBSET | 100 | 300 | 0.1 |
| T7AADNA (500 uM) | 100 | 300 | 0.1 |
| APS (10%) | 30 | 90 | 0.03 |
| water | 630.2 | 1890.6 | — |
| total | 1000 | 2000 | |

Buffers and Solutions Used in Bead Washes

1 L STOP-25 buffer can comprise: nuclease-free water, (880 mL); 1 M Tris-HCl (pH 8.0) (10 mL); 0.5 M EDTA (50 mL); 10% (vol/vol) Tween-20 (10 mL); and 2 M KCl (50 mL).

2L STOP-10 buffer can comprise: nuclease-free water (1,820 mL); 1 M Tris-HCl (pH 8.0) (20 mL); 0.5 M EDTA (40 mL); 10% (vol/vol) Tween-20 (20 mL); and 2 M KCl (100 mL).

250 ml Denaturation solution can comprise: nuclease-free water (242 mL); 10 M NaOH (3.75 mL); and 30% (wt/wt) Brij-35 (4.2 mL). In some embodiments, denaturation solution is prepared fresh.

500 ml Neutralization buffer can comprise: nuclease-free water (385 mL); 1 M Tris-HCl (pH 8.0) (50 mL); 0.5 M EDTA (10 mL); 10% (vol/vol) Tween-20 (5 mL); and 1 M NaCl (50 mL).

500 ml TET-Tris-EDTA-Tween buffer can comprise: nuclease-free water (480 mL); 1M Tris-HCl (pH 8.0) (5 mL); 0.5 M EDTA (10 mL); and 10% (vol/vol) Tween-20 (5 mL).

1L Hydrogel bead wash (HBW) buffer can comprise: nuclease-free water (980 mL); 1 M Tris-HCl (pH 8.0) (10 mL); 0.5 M EDTA (0.2 mL); and 10% (vol/vol) Tween-20 (10 mL).

1L Tris-buffered saline-EDTA-Triton (TBSET) buffer can comprise: nuclease-free water (822 mL); 1 M Tris-HCl (pH 8.0) (10 mL); 1 M NaCl (137 mL); 2 M KCl (1.35 mL); 0.5 M EDTA (20 mL); and 10% (vol/vol) Triton X-100 (10 mL).

10 ml 20% PFO mix can comprise 1H,1H,2H,2H-Perfluoro-1-octanol (2 mL); and Biorad Droplet Generation Oil for EvaGreen #1864005 (8 mL).

50 ml 1% v/v Span-80 Hexane mix can comprise: Span-80 (Sigma-Aldrich, cat. no. 56760-250ML) (0.5 mL); and Hexane (Sigma-Aldrich, cat. no. 227064-1L) (44.5 mL).

Breaking the Emulsion and Transfer of Beads to Aqueous Buffer

First, the top (mineral oil) and bottom (carrier oil) phases were removed from the 2-ml collection tubes, leaving ~500 µl of polymerized HBs per tube. 500 µl of Tris-buffered saline-EDTA-Triton (TBSET) buffer was added on top of the creamy-looking emulsion. In some embodiments, 15 ml falcon tubes are used instead of 2 ml tubes.

Second, to release polymerized HBs from the emulsion, 1 ml of 20% (vol/vol) PFO was added per tube, it was vortexed well, and centrifuged at 5,000 g at room temperature for 30 s. HBs appeared as a milky (or semitransparent) phase. In some embodiments, beads are centrifuged at 3200G for 2 min. Good separation was observed.

Third, the bottom 20% (vol/vol) of the PFO phase was removed and the previous step was repeated until the milky phase was transformed into a solid, well-packed, translucent mass on top of the 20% (vol/vol) PFO phase. In some embodiments, good separation was obtained at this step using 3200 g for 2 min.

Fourth, the bottom of the PFO phase was removed and 1 ml of 1% (vol/vol) Span-80 in hexane was added per tube. This was mixed vigorously by vortexing and centrifuged at 5,000 g at room temperature for 30 s. At this point, the HBs appeared as a solid mass at the bottom of the tube. The top hexane layer was removed. In some embodiments, the centrifugation step comprises 5 min at 3200 g. Good separation was observed and the hexane phase was easily removed.

Fifth, the previous step was repeated.

Sixth, the 15-ml tubes were filled with TBSET buffer, the tubes were vortexed, and then centrifuged at 3,000 g at room temperature for 3 min. The HBs sedimented, whereas traces of hexane appeared as a milky layer on the top. The supernatant was carefully aspirated, keeping the tip of the serological pipette at the liquid-air interface. In some embodiments the centrifugation time of this step is extended 5 min at a time until sufficient separation is obtained.

Seventh, the previous step was repeated two more times.

Eighth, after the third TBSET wash, the beads were resuspended in ice cold TBSET and passed on a 70 um strainer to a 50 ml falcon tube. In some embodiments, the 50 ml falcon tube with beads can be centrifuged for 10 min at 3200 g as needed to remove the supernatant and leave the beads on the desired volute. The supernatant can be saved on another tube for further centrifuging if beads are observed.

Example 2

Split-Pool Barcoding with PER-Catalyzed Oligonucleotide Extensions

Proof of principle experiments were performed combinatorially barcoding hydrogel beads according to the methods provided herein using PER-catalyzed over 4 barcoding rounds with 10 barcoding sequences on each round, yielding $10^4=10000$ unique bead barcodes. As proof of principle of the methods disclosed herein, four rounds of hairpin molecule-catalyzed split-pool bead barcoding were conducted using a set of ten first hairpins (SEQ ID NOS: 1-10), a set of ten second hairpins (SEQ ID NOS: 11-20), a set of ten third hairpins (SEQ ID NOS: 21-30), and a set of ten fourth hairpins (SEQ ID NOS: 31-40).

Before starting, washes of the beads of Example 1 that are in TBSET were performed 3 times into HB wash buffer for 5 min at 1000 g each time. In some embodiments, hairpins in 2 uM stock solutions are aliquoted in 96 well PCR plates.

First, the PER mix described in Table 3 was prepared according to the volume of beads that were going to be barcoded.

TABLE 3

PER MIX

| | PER mix 500 ul | Final |
|---|---|---|
| 4 parts HB with DNA in HBW buffer | 200 | — |
| 1 part 100 mM magnesium | 50 | 10 mM |
| 1 part 10X thermopol buffer | 50 | 1X |
| 2 parts 1 mM dHTP (A, T, C without G) | 100 | 200 uM |
| 1 part 100 mM spermidine | 50 | 10 mM |
| 1 part bst 10X | 50 | 1x |
| 0.1 part Hairpin 2 uM (add later) | 5 ul to each 50 ul reaction | 200 nM |

Second, the beads that are going to be barcoded are split into a number of wells of a PCR plate based on the corresponding number of unique barcodes (e.g., unique hairpin molecules) for each round. For example, if a user has 72 unique barcodes (e.g., unique hairpin molecules) and is performing 4 rounds (to generate $72^4=26$ M unique combinations), the PER mix is split equally into 72 wells on a 96 well PCR plate.

Third, a single first hairpin was added to each well. Varying hairpin concentrations (from 200 nM to as low as 20 nM) were found to work. In some embodiments, a 200 nM hairpin concentration ensures the reaction goes to completion during incubation.

Fourth, reactions were incubated at 37° C. shaking at 800 rpm for at least 3 hours after adding the hairpins to ensure the reaction goes to completion. In some embodiments, the incubation period is between 3 to 4 hours.

Fifth, at the end of the incubation, the beads were pooled together, well mixed, and then split again as described above.

Sixth, the set of second hairpin molecules were added as above, incubated for at least 3 hours, and the samples were pooled. Steps 3-5 were repeated for the set of third hairpin molecules and the set of fourth hairpin molecules.

After barcoding, the pooled sample can be used without washing for the capping reaction below. In some embodiments, if the capping is not performed immediately afterwards, the beads can be mixed with an equal volume of STOP-25 buffer and stored at 4° C. In some such embodiments, prior to the capping reaction the beads are washed back into HBW buffer by 3 times spinning at 300 g for 5 minutes (or longer if the beads do not sediment sufficiently) followed by addition of 0.1 part of NEB thermopol buffer. In some embodiments, after barcoding, the beads are not centrifuged above 300 g to prevent clumping.

As described below, the beads were subsequently capped with a capping oligonucleotide using a DNA extension reaction, were enzymatically treated to remove incomplete barcodes, and finally washed in a denaturing buffer to remove the second strand and leave only single stranded DNA on the beads.

In some embodiments, the PER Mix is made according to Table 4. In some such embodiments, the reaction is divided to the desired number of reactions (which can depend on the number of hairpins per round, such as, for example, 10-96 reactions at a time per round). Each hairpin can be added at 2 uM concentration at 10% of the volume per reaction (e.g., 10 ul hairpin added to 90 ul bead reaction).

TABLE 4

PER MIX

| | Stock Concentration | Final Concentration | PER reaction Master Mix (1000 uL) |
|---|---|---|---|
| Hydrogel Beads (HB) with DNA in Wash Buffer | N/A (should be 40% of total reaction volume) | N/A | 400 |
| Magnesium Sulfate MgSO4 | 100 mM | 10 mM | 100 |
| 10X thermopol buffer | 10x | 1X | 100 |
| dHTP (dATP, dTTP, dCTP without dGTP) | 10 mM (total) | 2 mM (total) | 200 |
| Spermidine | 100 mM | 10 mM | 100 |
| Bst Polymerase | 10x | 1x | 100 |
| | | | 1000 |

Capping Reaction and Exonuclease Enzymatic Cleanup

The barcoded beads from PER split-pool reaction above were mixed without washing with an equal volume of the capping mix described in Table 5. The reaction was incubated for at least 3 hours shaking at 800 rpm at 37° C.

TABLE 5

CAPPING MIX

| | For 100 ul capping mix | Final in mix |
|---|---|---|
| Capping oligo at 50 um (SEQ ID NO: 46) | 40 | 20 uM |
| water | 36 | — |
| bst | 10 | 1x |
| 10X thermopol buffer | 10 | 1x |
| 10 mM dNTP | 4 | 400 uM |

A post-capping enzymatic cleanup was performed to chew away uncapped single stranded DNA left in the beads using the NEB exonuclease I. First, the beads were washed 3 times with water. Beads were mixed well and spun down at 300 g for 3 minutes. Second, to the volume of beads left, 0.1 part exonuclease I buffer and 0.05 part exonuclease was added. For example, 180 ul of beads are provided with 20u1 of buffer and 10 ul of exonuclease (20 U/ul) for a final concentration of exo of 1 U/ul. Third, the reaction is incubated at 25'C 800 rpm for at least two hours. Finally, the reaction was stopped by adding an equal volume of STOP-25 buffer and mixing well. In some embodiments, the sample can now be stored at 4° C. prior to the final post-barcoding denaturing washes.

Denaturing Washes

It was found that performing the following steps using 1.5 ml tubes instead of 15 ml or 50 ml tubes could also work, and that centrifugation times can be three times shorter with 1.5 ml tubes.

First, all tubes were filled with STOP-25 buffer and mixed well. In some embodiments, the HBs can be stored at 4° C. overnight at this point.

Second, the 50-ml tubes containing the HBs were centrifuged at 300 g at room temperature for 15 min.

Third, using a serological pipette, the supernatant was removed, leaving a total volume of approximately 5-10 ml per tube. When using 50-ml tubes, some HBs can be observed in the supernatant. The supernatant was not discarded, but was transferred to fresh 50-ml tubes, and the HBs were collected by repeating centrifugation at 300 g at room temperature for 15 min.

Fourth, the HBs were washed three times in STOP-10 buffer. For the washes, 15-ml tubes were filled with STOP-10 buffer, rotated for 15 min at room temperature, centrifuged for 3 min at 300 g at room temperature, and the supernatant was removed. Less than 3 ml total volume per tube was left after the last wash. In some embodiments, the HBs can be stored at 4° C. for up to 6 months at this point.

Fifth, 250 ml of fresh denaturation solution was prepared.

Sixth, the four hydrogel-bead-containing 15-ml tubes were filled with denaturation solution, rotated for 10 min at room temperature, centrifuged for 3 min at 300 g at room temperature, and the supernatant was discarded.

Seventh, the HBs were washed three times in denaturation solution. For the washes, 15-ml tubes were filled with denaturation solution, then inverted and flicked to resuspend all beads. After incubating for 1 min at room temperature, the beads were centrifuged for 3 min at 300 g at room temperature, and the supernatant was removed. This step was repeated for two washes using neutralization buffer. Finally, two final washes were performed in TBSET buffer for long term storage of the beads.

Denaturing Gel Analysis

A 20 ul aliquot of beads was taken at multiple time points of interest during the barcoding to assay the progress of the oligonucleotide extension. Bead samples were run on a 10% or 15% urea denaturing gel. Prior to running the gel, the beads were dissolved with a reducing agent (e.g., DTT) and the barcodes were released by cleaving the dU base with NEB USER enzyme as described below.

First, 0.1 part of DTT, 0.1 part USER and 0.1 part cutsmart buffer were added to each bead sample (e.g., 7 ul of beads received 1 ul 1M DTT, 1 ul USER, and 1 ul cutsmart).

Second, the samples were incubated for at least 20 min at 37° C.

Third, an equal volume of formamide loading dye was added to each sample and samples were incubated at 95° C. for 10 min.

The samples were run on a urea gel with TBE buffer at 200V for about 45 min for a 10% gel and about 1 h 20 min for a 15% gel. Gels were stained with SYBR gold for 10 min and imaged.

It was found that the redox-cleavable beads generated according to the methods provided herein could be dissolved at 50 mM DTT. In addition to dissolving the beads, it was also found that the addition of USER enzyme was able to release the oligonucleotides (e.g., DNA barcode) from the beads generated according to the methods provided herein. Both of these attributes are useful, in part, because dissolving the beads and cleaving the DNA this manner allows a user to run the sample on a standard polyacrylamide gel and assess whether the barcodes have successfully been extended, and how efficiently.

Figure 6:
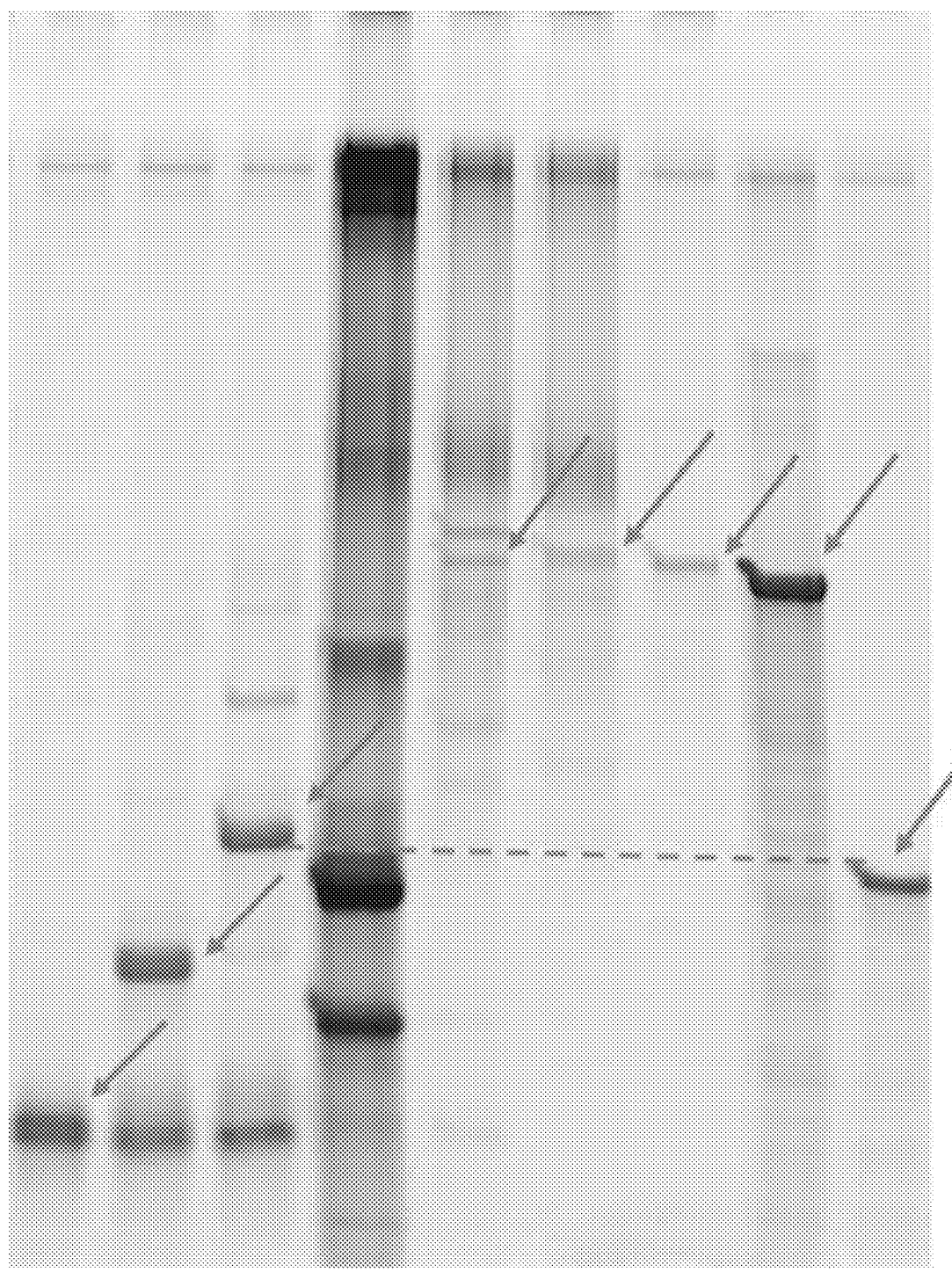
FIG. 6 depicts data related to the preparation of barcoded beads according the methods provided herein. The denaturing gel comprises: lane 1, second primer exchange reactions (PER) extension; lane 2, third PER extension; lane 3, fourth PER extension; lane 4, capping reaction; lane 5, water wash after capping; lane 6, enzymatic cleanup; lane 7, ssDNA after denaturing wash; lane 8, expected capped oligonucleotide (125 bp); and lane 9, expected barcoded oligonucleotide (74 bp).

FIG. 6 depicts a denaturing gel of beads at successive timepoints during the bead PER barcoding, capping, enzymatic cleanup and a denaturing wash leaving only complete single stranded DNA sequences on the beads. Relevant bands are noted by an arrow. The fourth PER extension is expected to yield a 74 bp barcoded oligo, which is compared against a 74 bp synthetic oligo (indicated with dashed line). Thus, as expected oligonucleotide (e.g., barcode) extension is occurring after each round of PER-catalyzed extension and the capping. These results demonstrate the production of combinatorially barcoded beads according to the methods provided herein. As further proof of principle, two bead PER barcoding, capping, and enzymatic cleanup reactions were also performed with different denaturing wash buffers.

Sanger Sequencing Analysis

Individual beads capped with the sequences described in above underwent PCR as follows. First, individual beads were isolated in a flat-bottom 96 well plate in droplets of about 3 ul. Second, 10 ul of USER enzyme in cutsmart buffer with 0.1M DTT was added to dissolve the beads and release the barcoding sequences for 20 min. Third, 5 ul of bst+0.5 ul 1 mM dNTP+in custsmart with 1 uM ACTPE2 primer (SEQ ID NO: 41) were added and incubated at room temperature for 10 min. Fourth, samples were heated at 95° C. for 3 min. Fifth, employing 4.8 ul of this sample, 5 ul Kapa HiFi HotStart ready mix 2X+0.1 u158-R1P5 primer (SEQ ID NO: 42) at 50 uM (for 0.1 uM final)+0.2 ul R2P7B1 primer (SEQ ID NO: 43) at 50 uM (for 0.1 uM final) were added. PCR conditions were as follows: 95° C. for 3 min, then 30 cycles of 98° C. for 10 s >62° C. for 20 s >72° C. for 25 s, then a final step at 72° C. for 5 min. Finally, PCR products were run on a 12% native gel, the expected product being 227 bp long.

Sanger sequencing trances for 11 beads that were individually picked, dissolved and PCR amplified demonstrated excellent agreement with the expected sequences. Thus, the bead barcoding reaction provided herein is efficient and results in unique barcodes for each bead. These results demonstrate the production of combinatorially barcoded beads according to the methods provided herein.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of combinatorially barcoding particle-associated oligonucleotides, comprising steps in the following order:
   (a) providing a particle comprising a plurality of oligonucleotides each comprising an input primer, wherein the input primer is releasably covalently attached to the particle;
   (b) contacting the particle with a solution comprising a first hairpin molecule and a polymerase having strand displacement activity, wherein the first hairpin molecule comprises:
      (i) an unpaired first 3' toehold domain complementary to the input primer,
      (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, wherein the first barcode segment is 5' of the first coupling segment and comprises at least 3 nucleotides,
      (iii) a first hairpin loop domain, and
      (iv) a polymerase stopper capable of terminating polymerization located (1) in the first hairpin loop domain, or (2) between the first paired stem domain and the first hairpin loop domain;
   (c) extending the input primer hybridized to the first 3' toehold domain through the first paired stem domain of the first hairpin molecule, thereby displacing the 5' subdomain of the first hairpin molecule and forming a first extended oligonucleotide comprising the input primer, the first barcode segment and the first coupling segment.

2. The method of claim 1, further comprising steps (d) and (e) in the following order:
   (d) contacting the particle with a second hairpin molecule, wherein the second hairpin molecule comprises:
      (i) an unpaired second 3' toehold domain complementary to the first coupling segment,
      (ii) a second paired stem domain formed by intramolecular nucleotide base pairing between a 3' subdomain of the second hairpin molecule and a 5' subdomain of the second hairpin molecule, wherein the second paired stem domain comprises a second coupling segment, a second barcode segment, and complements thereof, wherein the second barcode segment is 5' of the second coupling segment and comprises at least 3 nucleotides,
      (iii) a second hairpin loop domain, and
      (iv) a polymerase stopper capable of terminating polymerization located (1) in the second hairpin loop domain, or (2) between the second paired stem domain and the second hairpin loop domain; and
   (e) extending the first coupling segment of the first extended oligonucleotide hybridized to the second 3' toehold domain through the second paired stem domain of the second hairpin molecule, thereby displacing the 5' subdomain of the second hairpin molecule and forming a second extended oligonucleotide comprising the first coupling segment, the second barcode segment and the second coupling segment,
   wherein the first barcode segment is selected from a first set of barcode segments,
   wherein the second barcode segment is selected from a second set of barcode segments, the second barcode segment being different from the first barcode segment, and
   wherein the first and second barcode segments are each selected from separate sets of barcode segments.

3. The method of claim 2, further comprising:
   (f) contacting the particle with a third hairpin molecule, wherein the third hairpin molecule comprises:
      (i) an unpaired third 3' toehold domain complementary to the second coupling segment,
      (ii) a third paired stem domain formed by intramolecular nucleotide base pairing between a 3' subdomain of the third hairpin molecule and a 5' subdomain of the third hairpin molecule, wherein the third paired stem domain comprises a third coupling segment, a third barcode segment, and complements thereof, wherein the third barcode segment is 5' of the third coupling segment and comprises at least 3 nucleotides,
      (iii) a third hairpin loop domain, and
      (iv) a polymerase stopper capable of terminating polymerization located (1) in the third hairpin loop domain, or (2) between the third paired stem domain and the third hairpin loop domain; and
   (g) extending the second coupling segment of the second extended oligonucleotide hybridized to the third 3' toehold domain through the third paired stem domain of the third hairpin molecule, thereby displacing the 5' subdomain of the third hairpin molecule and forming a third extended oligonucleotide comprising the second coupling segment, the third barcode segment and the third coupling segment.

4. A method of combinatorially barcoding particle-associated oligonucleotides, comprising steps in the following order:
   (a) providing a particle comprising a plurality of oligonucleotides each comprising an input primer, wherein the input primer is releasably covalently attached to the particle;

(b) contacting the particle with a solution comprising a first hairpin molecule and a polymerase having strand displacement activity, wherein the first hairpin molecule comprises:
  (i) an unpaired first 3' toehold domain complementary to the input primer,
  (ii) a first paired stem domain formed by intramolecular nucleotide base pairing between a 3' subdomain of the first hairpin molecule and a 5' subdomain of the first hairpin molecule, wherein the first paired stem domain comprises a first coupling segment, a first barcode segment, and complements thereof, wherein the first barcode segment is 5' of the first coupling segment,
  (iii) a first hairpin loop domain, and
  (iv) a polymerase stopper capable of terminating polymerization located (1) in the first hairpin loop domain, or (2) between the first paired stem domain and the first hairpin loop domain; and
(c) extending the input primer hybridized to the first 3' toehold domain through the first paired stem domain of the first hairpin molecule, thereby displacing the 5' subdomain of the first hairpin molecule and forming a first extended oligonucleotide comprising the input primer, the first barcode segment and the first coupling segment;
(d) contacting the particle with a (n+1)th hairpin molecule, wherein the (n+1)th hairpin molecule comprises:
  (i) an unpaired (n+1)th 3' toehold domain complementary to the nth coupling segment,
  (ii) a (n+1)th paired stem domain formed by intramolecular nucleotide base pairing between a 3' subdomain of the (n+1)th hairpin molecule and a 5' subdomain of the (n+1)th hairpin molecule, wherein the (n+1)th paired stem domain comprises a (n+1)th coupling segment, a (n+1)th barcode segment, and complements thereof, wherein the (n+1)th barcode segment is 5' of the (n+1)th coupling segment,
  (iii) a (n+1)th hairpin loop domain, and
  (iv) a polymerase stopper capable of terminating polymerization located (1) in the (n+1)th hairpin loop domain, or (2) between the (n+1)th paired stem domain and the (n+1)th hairpin loop domain;
(e) extending the nth coupling segment of the nth extended oligonucleotide hybridized to the (n+1)th 3' toehold domain through the (n+1)th paired stem domain of the (n+1)th hairpin molecule, thereby displacing the 5' subdomain of the (n+1)th hairpin molecule and forming a (n+1)th extended oligonucleotide comprising the nth coupling segment, the (n+1)th barcode segment and the (n+1)th coupling segment;
(f) repeating steps (d) and (e) nth times, wherein n is a positive integer, and optionally n is an integer between 1 and 8;
(g) performing a capping reaction comprising:
  contacting a capping oligonucleotide with the (n+1)th extended oligonucleotide, wherein the capping oligonucleotide is a single-stranded molecule comprising a 3' region capable of annealing to the 3' end of the first extended oligonucleotide, the second extended oligonucleotide, or the third extended oligonucleotide; and
  extending the (n+1)th extended oligonucleotide hybridized with the capping oligonucleotide, thereby generating a capped oligonucleotide; and (h) contacting the particle with a single strand-specific exonuclease,
  wherein the capped oligonucleotide comprises the first barcode segment and a second barcode segment,
  wherein the first barcode segment is selected from a first set of barcode segments,
  wherein the second barcode segment is selected from a second set of barcode segments, the second barcode segment being different from the first barcode segment, and
  wherein the first and second barcode segments are each selected from separate sets of barcode segments.

5. The method of claim 4, wherein the particle comprises silica, glass, acrylamide, polyacrylamide, polypropylene, latex, nylon, plastic, ceramic, polystyrene, silicon, agarose, a cellulosic material, a metal, polydimethylsiloxane (PDMS), or any combination thereof.

6. The method of claim 4, wherein the particle comprises a bead, wherein the bead comprises a hydrogel bead, a magnetic bead, a glass bead, a cellulose bead, an epichlorohydrin-cross-linked-dextran bead, a polyacrylamide bead, an agarose bead, a polystyrene bead, or a gel-based bead.

7. The method of claim 3, wherein the first barcode segment, second barcode segment, and/or third barcode segment comprise a unique molecular identifier (UMI), a primer sequence, a primer annealing sequence, an attachment sequence, a sequencing primer sequence, or any combination thereof.

8. The method of claim 2, wherein the first barcode segment and/or second barcode segment are independently selected from a set of 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 different barcode segments.

9. The method of claim 4, wherein the first barcode segment and/or second barcode segment are independently selected from a set of 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 different barcode segments.

10. The method of claim 3, further comprising a capping reaction, comprising:
  contacting a capping oligonucleotide with the first extended oligonucleotide, the second extended oligonucleotide, and/or the third extended oligonucleotide, wherein the capping oligonucleotide is a single-stranded molecule comprising a 3' region capable of annealing to the 3' end of the first extended oligonucleotide, the second extended oligonucleotide, or the third extended oligonucleotide; and
  extending the first extended oligonucleotide, the second extended oligonucleotide, and/or the third extended oligonucleotide hybridized with the capping oligonucleotide, thereby generating a capped oligonucleotide.

11. The method of claim 10, further comprising: contacting the particle with a single strand-specific exonuclease.

12. The method of claim 2, wherein the particle comprises silica, glass, acrylamide, polyacrylamide, polypropylene, latex, nylon, plastic, ceramic, polystyrene, silicon, agarose, a cellulosic material, a metal, polydimethylsiloxane (PDMS), or any combination thereof.

13. The method of claim 2, wherein the first hairpin molecule and/or second hairpin molecule further comprises a 3' poly (dT) region, an inverted-dT at its 3' end, dideoxy (T) (ddT), or a nucleoside not capable of being 3' extended by a DNA polymerase.

14. The method of claim 4, wherein the capping oligonucleotide comprises a polyA capping sequence.

15. The method of claim 2, wherein the particle is a gel bead and the input primer is attached to the gel bead by an acrydite moiety.

16. The method of claim 2, wherein the particle is not washed between step (c) and step (d).

17. The method of claim 1, wherein the particle-associated oligonucleotides are presented by SEQ ID NO: 47.

18. The method of claim 10, wherein the capping oligonucleotide is represented by SEQ ID NO: 46.

\* \* \* \* \*